(12) United States Patent
Kurosawa et al.

(10) Patent No.: US 9,175,028 B2
(45) Date of Patent: Nov. 3, 2015

(54) GLYCOSIDE COMPOUND

(71) Applicant: AJINOMOTO CO., INC., Chuo-ku (JP)

(72) Inventors: Wataru Kurosawa, Kawasaki (JP); Takuya Toyoda, Kawasaki (JP); Risa Ubagai, Kawasaki (JP); Yoshihito Nogusa, Kawasaki (JP); Kana Ohyama, Kawasaki (JP); Yusuke Amino, Kawasaki (JP)

(73) Assignee: AJINOMOTO CO., INC., Chuo-ku (JP)

( * ) Notice: Subject to any disclaimer, the term of this patent is extended or adjusted under 35 U.S.C. 154(b) by 0 days.

(21) Appl. No.: 13/923,881

(22) Filed: Jun. 21, 2013

(65) Prior Publication Data

US 2013/0288992 A1 Oct. 31, 2013

Related U.S. Application Data

(63) Continuation of application No. PCT/JP2011/079933, filed on Dec. 22, 2011.

(30) Foreign Application Priority Data

Dec. 22, 2010 (JP) ................................. 2010-286207

(51) Int. Cl.
*C07H 15/207* (2006.01)
*C12P 19/46* (2006.01)
*A23L 1/30* (2006.01)
*C07H 15/203* (2006.01)

(52) U.S. Cl.
CPC ............... *C07H 15/207* (2013.01); *A23L 1/30* (2013.01); *C07H 15/203* (2013.01); *C12P 19/46* (2013.01)

(58) Field of Classification Search
CPC ...... C12P 19/46; C07H 15/203; C07H 15/207
USPC ................ 514/35; 536/18.2; 435/79
See application file for complete search history.

(56) References Cited

U.S. PATENT DOCUMENTS

| | | | |
|---|---|---|---|
| 5,700,784 A | 12/1997 | Shinojima et al. | |
| 6,306,376 B1 | 10/2001 | Philippe | |
| 2003/0153030 A1 | 8/2003 | Otto et al. | |
| 2004/0138148 A1 | 7/2004 | Fushimi et al. | |
| 2009/0111739 A1 | 4/2009 | Kajihara et al. | |
| 2011/0245166 A1 | 10/2011 | Kajihara et al. | |
| 2013/0345129 A1 | 12/2013 | Kajihara et al. | |

FOREIGN PATENT DOCUMENTS

| | | | |
|---|---|---|---|
| CN | 1849068 A | 10/2006 | |
| CN | 1852707 A | 10/2006 | |
| CN | 101398417 A | 4/2009 | |
| CN | 101643484 A | 2/2010 | |
| EP | 0 597 776 A1 | 5/1994 | |
| EP | 0597776 A1 * | 5/1994 | ........... C07H 15/203 |
| EP | 1 367 060 A1 | 12/2003 | |
| JP | 06-065051 A | 3/1994 | |
| JP | 07-173046 A | 7/1995 | |
| JP | 08-113528 A | 5/1996 | |
| JP | 08-268858 A | 10/1996 | |
| JP | 08-268868 A | 10/1996 | |
| JP | 08-268869 A | 10/1996 | |
| JP | 08-268870 A | 10/1996 | |

(Continued)

OTHER PUBLICATIONS

Morikawa et al, Chem. Pharm. Bull. 2004, 52(10), 1194-99.*
Morikawa et al, Chem. Pharm. Bull. 2004, 52(10), 1194-119.*
Yang et al, Rapid Communications in Mass Spectrometry, 2007, 21, 1833-40.*
Koto et al, Bull. Chem. Soc. Jpn., 1981, 54, 1895-96.*
Appendino et al, Organic Letters, 2002, 4(22), 3839-41.*
Hennen et al, J. Org. Chem. 1988, 53, 4939-45.*
International Search Report issued Mar. 19, 2012 in PCT/JP2011/079933.
English translation of International Preliminary Report on Patentability and Written Opinion issued Jul. 2, 2013 in PCT/JP2011/079933.
Extended European Search Report issued May 23, 2014 in Patent Application No. 11850476.0.

(Continued)

*Primary Examiner* — Ganapathy Krishnan
(74) *Attorney, Agent, or Firm* — Oblon, McClelland, Maier & Neustadt, L.L.P.

(57) ABSTRACT

Compounds of formula (I")

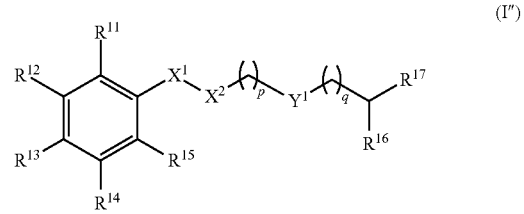

(I")

wherein:
$R^{11}$, $R^{12}$, $R^{13}$, $R^{14}$ and $R^{15}$ are hydrogen, hydroxyl, $C_{1-6}$ alkyl, $C_{1-6}$ alkoxy, $C_{1-6}$ alkyl-carbonyloxy, or a G-O— group, and at least one of $R^{11}$, $R^{12}$, $R^{13}$, $R^{14}$ and $R^{15}$ is a G-O— group, wherein G is a saccharide residue, $X^1$ is a single bond, or a methylene group, an ethylene group, a trimethylene group, a vinylene group or —CH=CH—CH$_2$—, $X^2$ is —CO—O— or —O—CO—, p and q are integer ofs 0 to 7, and p+q=0 to 8, $Y^1$ is methylene, ethylene or an alkenylene group having a carbon number of 2 to 15 and 1 to 3 double bonds, and $R^{16}$ and $R^{17}$ are hydrogen, methyl or ethyl, or $R^{16}$ and $R^{17}$ form a $C_{3-6}$ cycloalkyl group, are useful as GLP-1 secretion promoting agents.

26 Claims, 22 Drawing Sheets

(56) References Cited

FOREIGN PATENT DOCUMENTS

| JP | 08-268871 A | | 10/1996 | |
|---|---|---|---|---|
| JP | 11-071225 A | | 3/1999 | |
| JP | 3506466 B2 | | 3/2004 | |
| JP | 2007-326825 | * | 12/2007 | ............. A01N 43/40 |
| JP | 2007-326825 A | | 12/2007 | |
| JP | 4163631 B2 | | 10/2008 | |
| JP | 2009-067781 A | | 4/2009 | |
| JP | 2009-209060 | * | 9/2009 | ........... C07H 15/203 |
| JP | 2009-209060 A | | 9/2009 | |
| JP | 2009-234962 A | | 10/2009 | |
| JP | 2010-120896 A | | 6/2010 | |
| JP | 2010-120897 A | | 6/2010 | |
| JP | 2010-120898 A | | 6/2010 | |
| JP | 2010-120899 A | | 6/2010 | |
| JP | 2010-120900 A | | 6/2010 | |
| WO | WO 2009/093007 A2 | * | 7/2009 | ............. A61K 39/39 |
| WO | WO 2009/105936 | * | 9/2009 | ......... A61K 31/7034 |
| WO | WO 2009/105936 A1 | | 9/2009 | |
| WO | WO 2009/156324 A2 | | 12/2009 | |

OTHER PUBLICATIONS

Shinkiti Koto, et al., "a-glucosylation of phenols with tetra-O-benzyl-a-D-glucose", Bulletin of the Chemical Society of Japan, vol. 54, No. 6, 1981, pp. 1895-1896.

Li Yang, et al., "High-performance liquid chromatography-diode array detection/electrospray ionization mass spectrometry for the simultaneous analysis of cis-, trans- and dihydro-2-glucosyloxycinnamic acid derivatives from Dendrobium medicinal plants", Rapid Communications in Mass Spectrometry, vol. 21, No. 12, 2007, pp. 1833-1840 and Cover Page.

Xia Wu, et al., "Chemical constituents of Lavandula augustifolia", Huaxue Xuebao, vol. 65, No. 16, 2007, pp. 1649-1653 and Cover Page.

"Novel capsaicinoid-like substances, capsiate and dihydrocapsiate, from the fruits of a nonpungent cultivar, CH-19 sweet, of pepper", Journal of Agricultural and Food Chemistry, vol. 46, No. 5, XP000751945, May 1, 1998, pp. 1695-1697.

Fumiharu Higashiguchi, et al, "Purification and structure determination of glucosides of capsaicin and dihydrocapsaicin from various capsicum fruits", Journal of Agricultural and Food Chemistry, vol. 54, No. 16, XP055118581, Aug. 1, 2006, pp. 5948-5953.

Astrid J. Smeets, et al., "The acute effects of a lunch containing capsaicin on energy and substrate utilisation, hormones and satiety", European Journal of Nutrition, vol. 48, No. 4, XP019712654, Feb. 24, 2009, pp. 229-234.

Dong X in-rong, et al. "Synthesis of Capsaicinoids Glucoside", Natural Product Research Development, vol. 20, (2008), pp. 403-407.

* cited by examiner

Fig. 13
synthesis of the derivatives
Compound 16
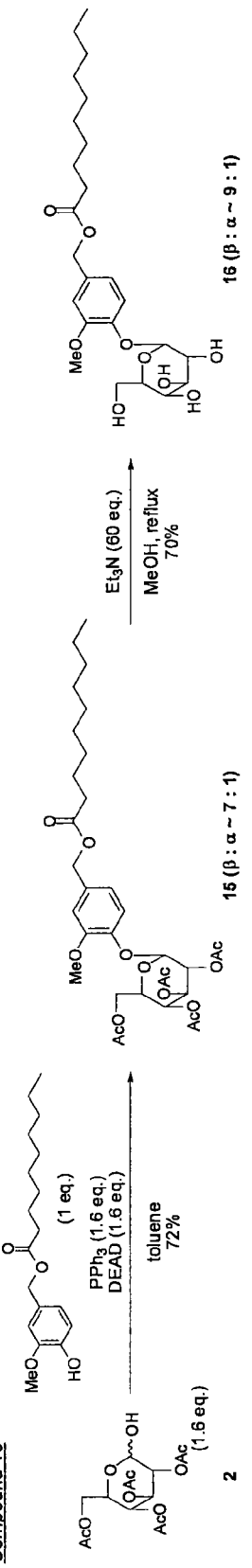
Compound 18
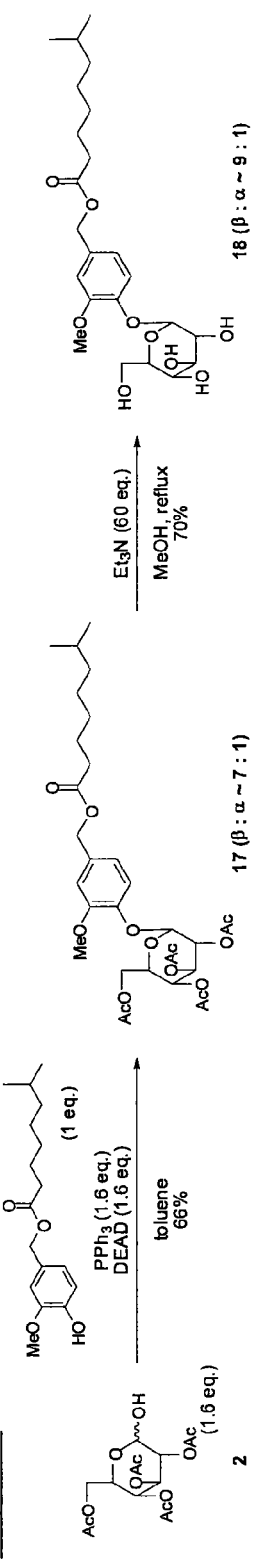
Compound 20
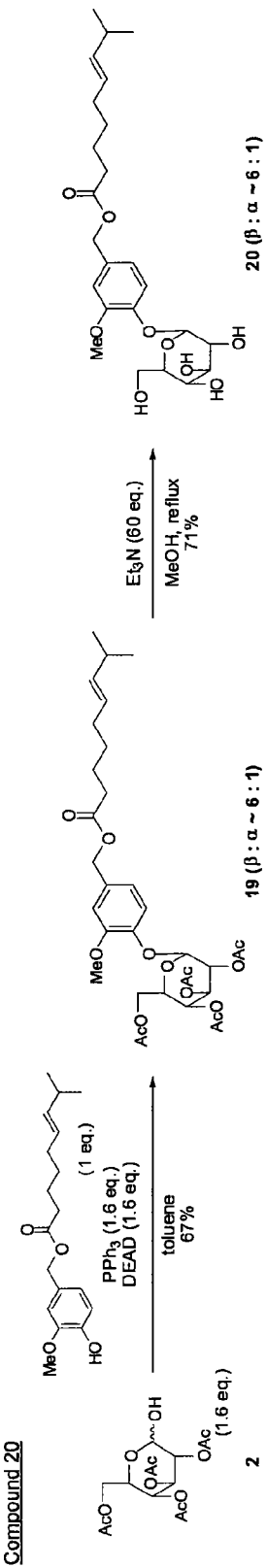

GLYCOSIDE COMPOUND

CROSS REFERENCES TO RELATED APPLICATIONS

This application is a continuation of International Patent Application No. PCT/JP2011/079933, filed on Dec. 22, 2011, and claims priority to Japanese Patent Application No. 2010-286207, filed on Dec. 22, 2010, both of which are incorporated herein by reference in their entireties.

BACKGROUND OF THE INVENTION

1. Field of the Invention

The present invention relates to a particular compound. Moreover, it relates to a production method of the compound, and a glucagon-like peptide-1 (GLP-1) secretion promoting agent, a pharmaceutical composition, a food composition and a cosmetic composition, each containing the compound.

2. Discussion of the Background

In recent years, many studies have been made around capsaicin.

JP-B-3506466 discloses capsaicin glycoside and the like. However, the capsaicin glycoside can reduce the pungent taste of capsaicin but cannot always eliminate the pungent taste completely when it is blended at a high concentration.

In addition, JP-A-2007-326825 discloses a composition for controlling harmful organisms, which contains (a) 4-phenoxyphenyl (RS)-2-(2-pyridyloxy)propyl=ethyl, and (b) capsaicinoid or capsinoid, or a glycoside thereof. However, the specific saccharide residue is not shown and the use thereof is extremely limited.

On the other hand, JP-B-4163631 discloses a fermentation composition of nonpungent chili pepper (*Capsicum annuum*) and use thereof. However, since such nonpungent chili peppers are generally in the form of oily liquid, the method for improving the purity is limited to extraction, column purification and the like.

Glucagon-like peptide-1 (GLP-1) is a peptide made from the same gene proglucagon sequence as that of glucagon. GLP-1 is one of the incretin factors secreted from the small intestine, and has actions of enhancement of glucose concentration-dependent insulin secretion, Langerhans' islets β cell proliferation, suppression of glucagon secretion, suppression of stomach excretory function, regulation of central appetite and the like. A substance having a GLP-1 secretion promoting action can be utilized as a prophylactic or therapeutic agent for diabetes (particularly type II diabetes) or an anorexigenic agent.

SUMMARY OF THE INVENTION

Accordingly, it is one object of the present invention to provide novel solid compounds, which are completely free of a pungent taste even at a high concentration use, shows excellent stability even in various use conditions, and shows a remarkable GLP-1 secretion enhancing effect.

It is another object of the present invention to provide novel methods of producing such a compound.

It is another object of the present invention to provide novel glucagon-like peptide-1 (GLP-1) secretion promoting agents which contain such a compound.

It is another object of the present invention to provide novel pharmaceutical compositions which contain a such a compound.

It is another object of the present invention to provide novel food composition which contain such a compound.

It is another object of the present invention to provide novel cosmetic compositions which contain such a compound.

These and other objects, which will become apparent during the following detailed description, have been achieved by the inventors' discovery of particular compounds, which are described below.

Accordingly, the present invention provides:

(1) A compound represented by the formula (I″):

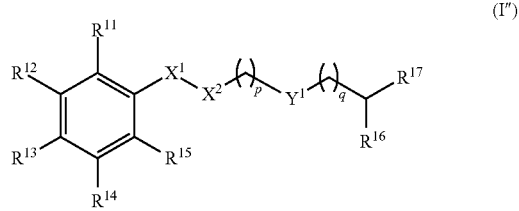

wherein $R^{11}$, $R^{12}$, $R^{13}$, $R^{14}$ and $R^{15}$ are each independently a hydrogen atom, a hydroxyl group, a $C_{1-6}$ alkyl group, a $C_{1-6}$ alkoxy group, a $C_{1-6}$ alkyl-carbonyloxy group, or a G-O— group, and at least one of $R^{11}$, $R^{12}$, $R^{13}$, $R^{14}$ and $R^{15}$ is a G-O— group, is wherein G is a saccharide residue, $X^1$ is a single bond, or a methylene group, an ethylene group, a trimethylene group, a vinylene group or —CH=CH—CH$_2$—, $X^2$ is —CO—O— or —O—CO—, p and q are each an integer of 0 to 7, which satisfy a relationship of p+q=0 to 8, $Y^1$ is a methylene group, an ethylene group or an alkenylene group having a carbon number of 2 to 15 and 1 to 3 double bonds, wherein the double bond may be any of cis and trans, and $R^{16}$ and $R^{17}$ are each independently a hydrogen atom, a methyl group or an ethyl group, or $R^{16}$ and $R^{17}$ form a $C_{3-6}$ cycloalkane together with the carbon atom bonded thereto.

(2) The compound described in (1), which is represented by the formula (I″-b):

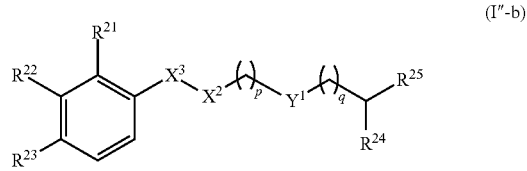

wherein $R^{21}$ is a hydrogen atom, $R^{22}$ is a methoxy group, and $R^{23}$ is a G-O— group, or $R^{21}$ is a G-O— group, $R^{22}$ is a methoxy group, and $R^{23}$ is a hydrogen atom, or $R^{21}$ is a hydrogen atom, $R^{22}$ is a G-O— group, and $R^{23}$ is a methoxy group, wherein G is a saccharide residue, $X^3$ is a methylene group, an ethylene group or —CH=CH—CH$_2$—, $X^2$ is —CO—O— or —O—CO—, p and q are each an integer of 0 to 7, which satisfy a relationship of p+q=0 to 8, $Y^2$ is a methylene group, an ethylene group or a vinylene group, and $R^{24}$ and $R^{25}$ are each independently a hydrogen atom or a methyl group, or $R^{24}$ and $R^{25}$ form a $C_{3-6}$ cycloalkane together with the carbon atom bonded thereto.

(3) The compound described in (1), which is represented by the formula (I'):

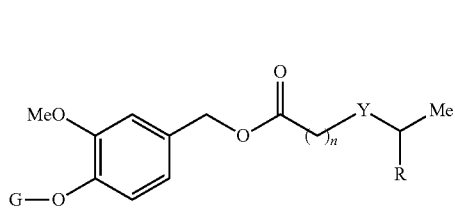

wherein Y is an ethylene group or a vinylene group,
R is a hydrogen atom or a methyl group,
G is a saccharide residue, and
n is an integer of 3 to 5.

(4) The compound described in (3), which is represented by the formula (I-1) or (I-2):

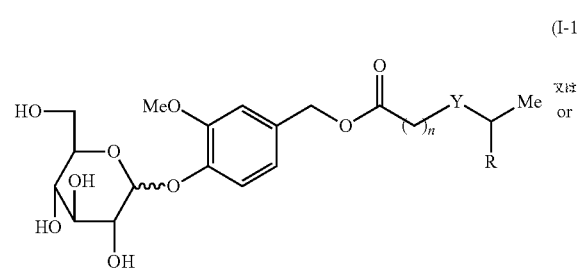

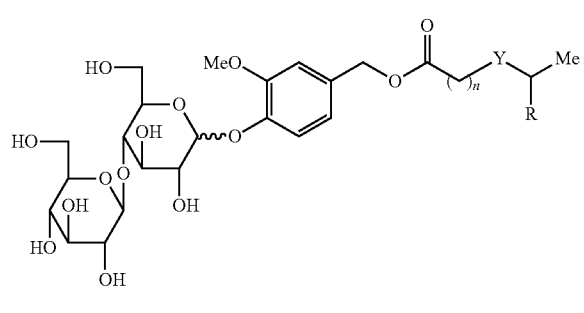

wherein Y is an ethylene group or a vinylene group,
R is a hydrogen atom or a methyl group, and
n is an integer of 3 to 5.

(5) The compound described in (4), which is represented by the formula (I-a):

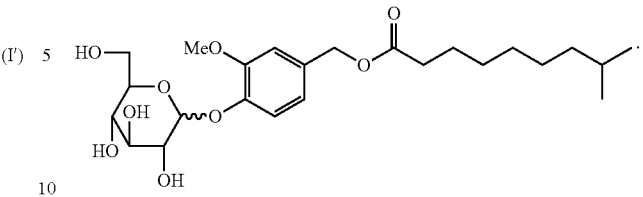

(6) The compound described in (4), which is represented by the formula (I-b):

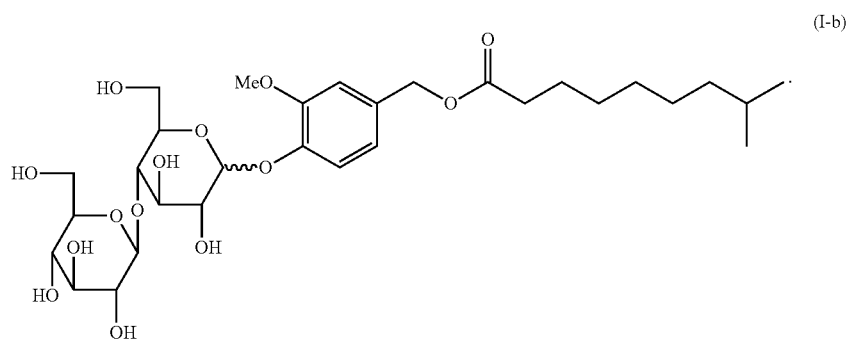

(7) The compound described in (4), which is represented by the formula (I-c):

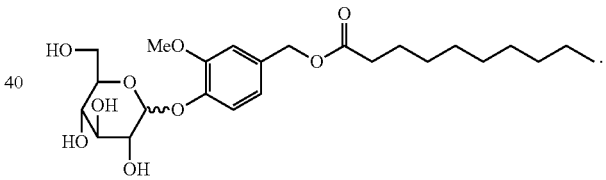

(8) The compound described in (4), which is represented by the formula (I-d):

(I-d)

(9) The compound described in (4), which is represented by the formula (I-e):

(I-e)

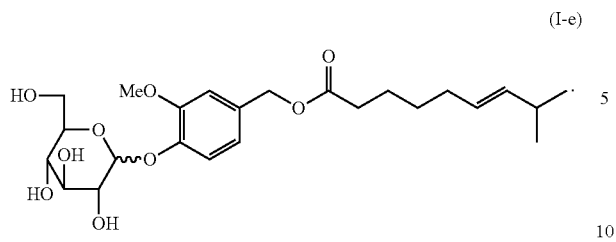

(10) A GLP-1 secretion promoting agent comprising the compound described in any one of (1)-(9).

(11) A pharmaceutical composition comprising the compound described in any one of (1)-(9).

(12) A food composition comprising the compound described in any one of (1)-(9).

(13) A cosmetic composition comprising the compound described in any one of (1)-(9).

(14) A method of producing the compound described in (1), comprising glycosidating a compound represented by the formula (XIV):

(XIV)

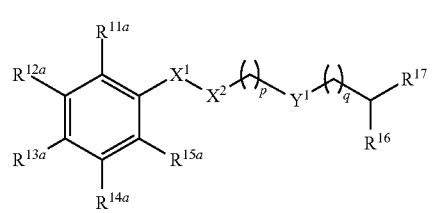

wherein $R^{11a}$, $R^{12a}$, $R^{13a}$, $R^{14a}$ and $R^{15a}$ are each independently a hydrogen atom, a hydroxyl group, a $C_{1-6}$ alkyl group, a $C_{1-6}$ alkoxy group or a $C_{1-6}$ alkyl-carbonyloxy group, and at least one of $R^{11a}$, $R^{12a}$, $R^{13a}$, $R^{14a}$ and $R^{15a}$ is a hydroxyl group, and other symbols are as defined in (1).

(15) A method of producing the compound described in (3), comprising glycosidating a compound represented by the formula (II):

(II)

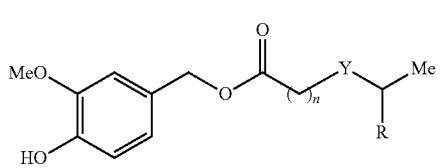

wherein Y is an ethylene group or a vinylene group,

R is a hydrogen atom or a methyl group, and n is an integer of 3 to 5.

(16) A method of producing a compound represented by the formula (I″-1):

(I″-1)

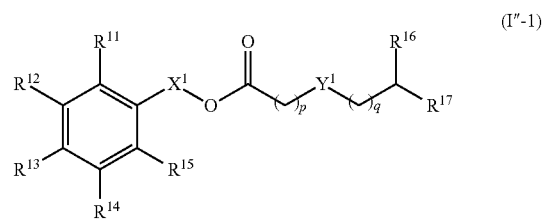

wherein each symbol is as defined in (1), comprising reacting a compound represented by the formula (XV):

(XV)

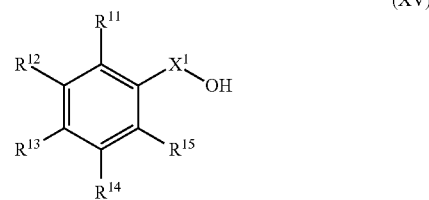

wherein each symbol is as defined in (1), with a compound represented by the formula (XVI):

(XVI)

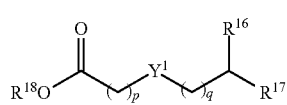

wherein $R^{18}$ is a hydrogen atom or a $C_{1-6}$ alkyl group, and other symbols are as defined in (1), or a salt thereof.

(17) A method of producing a compound represented by the formula (I″-2):

(I″-2)

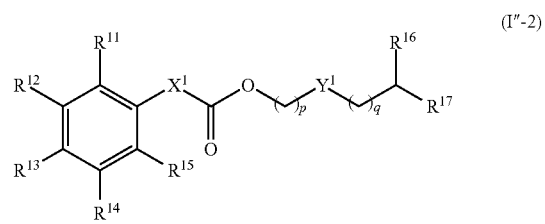

wherein each symbol is as defined in (1), comprising reacting a compound represented by the formula (XVII):

(XVII)

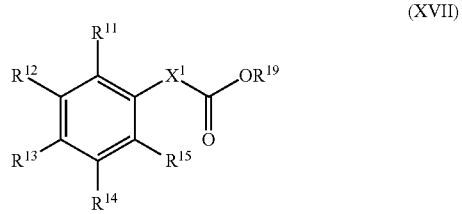

wherein $R^{19}$ is a hydrogen atom or a $C_{1-6}$ alkyl group, and other symbols are as defined in (1), or a salt thereof, with a compound represented by the formula (XVIII):

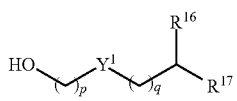

wherein each symbol is as defined in (1).

(18) A method of producing the compound described in (3), comprising reacting a compound represented by the formula (III):

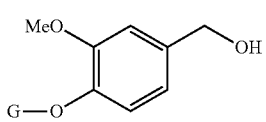

wherein G is a saccharide residue, with a compound represented by the formula (IV):

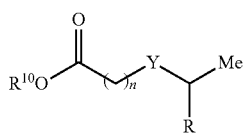

wherein $R^{10}$ is a hydrogen atom or a $C_{1-6}$ alkyl group,

Y is an ethylene group or a vinylene group,

R is a hydrogen atom or a methyl group, and n is an integer of 3 to 5, or a salt thereof.

(19) A method of producing the compound described in (4), comprising the following (step a) and (step b):

(step a) reacting a compound represented by the formula (II):

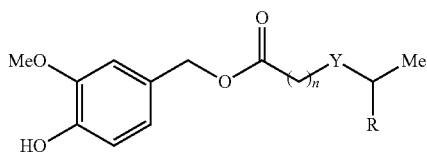

wherein Y is an ethylene group or a vinylene group,

R is a hydrogen atom or a methyl group, and n is an integer of 3 to 5, with a compound represented by the formula (V) or (VI):

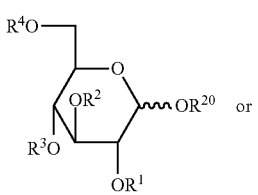

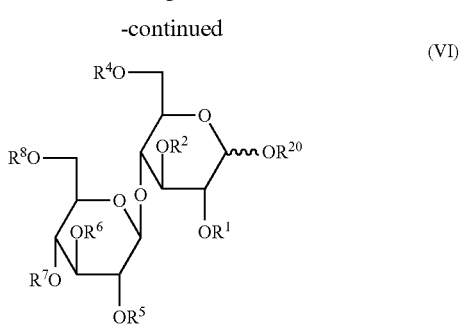

wherein $R^1$, $R^2$, $R^3$, $R^4$, $R^5$, $R^6$, $R^7$ and $R^8$ are each independently a hydroxyl-protecting group, and $R^{20}$ is a hydrogen atom or a hydroxyl-protecting group, to give a compound represented by the formula (VII) or (VIII):

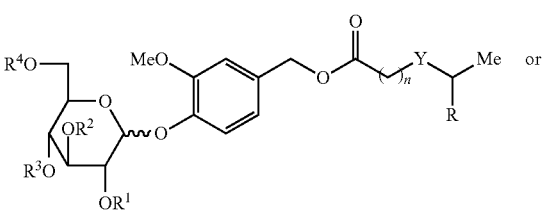

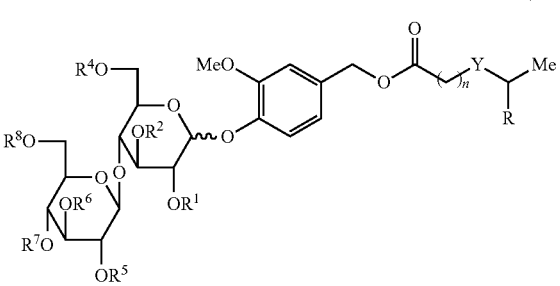

wherein $R^1$, $R^2$, $R^3$, $R^4$, $R^5$, $R^6$, $R^7$ and $R^8$ are each independently a hydroxyl-protecting group, Y is an ethylene group or a vinylene group, R is a hydrogen atom or a methyl group, and n is an integer of 3 to 5; and (step b) removing the hydroxyl-protecting groups of the compound represented by the formula (VII) or (VIII).

(20) The production method described in (19), wherein the removal of the protecting groups in (step b) is performed in the presence of lipase.

(21) A method of producing the compound described in (4), comprising reacting a compound represented by the formula (XII) or (XIII):

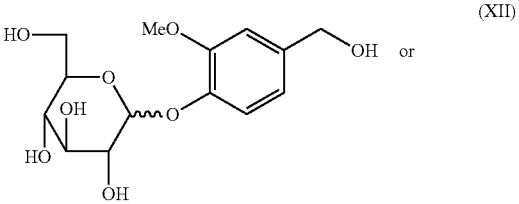

-continued

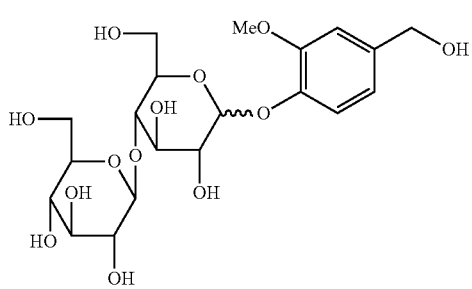
(XIII)

with a compound represented by the formula (IV):

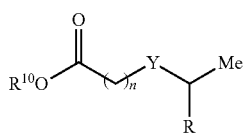
(IV)

wherein $R^{10}$ is a hydrogen atom or a $C_{1-6}$ alkyl group,
Y is an ethylene group or a vinylene group,
R is a hydrogen atom or a methyl group, and
n is an integer of 3 to 5, or a salt thereof.

(22) A method of producing the compound described in (4), comprising the following (step a), (step b) and (step c):

(step a) reacting a compound represented by the formula (IX):

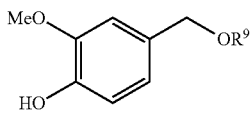
(IX)

wherein $R^9$ is a hydroxyl-protecting group, with a compound represented by the formula (V) or (VI):

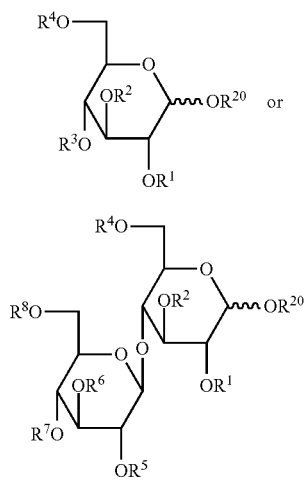
(V)

(VI)

wherein $R^1$, $R^2$, $R^3$, $R^4$, $R^5$, $R^6$, $R^7$ and $R^8$ are each independently a hydroxyl-protecting group, and
$R^{20}$ is a hydrogen atom or a hydroxyl-protecting group, to give a compound represented by the formula (X) or (XI):

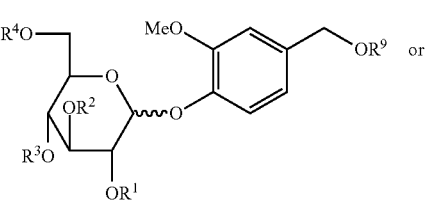
(X)

(XI)

wherein $R^1$, $R^2$, $R^3$, $R^4$, $R^5$, $R^6$, $R^7$, $R^8$, and $R^9$ are each independently a hydroxyl-protecting group;

(step b) removing the hydroxyl-protecting groups of the compound represented by the formula (X) or (XI), to give a compound represented by the formula (XII) or (XIII):

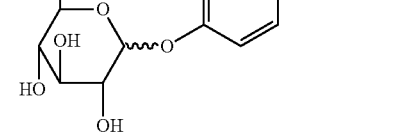
(XII)

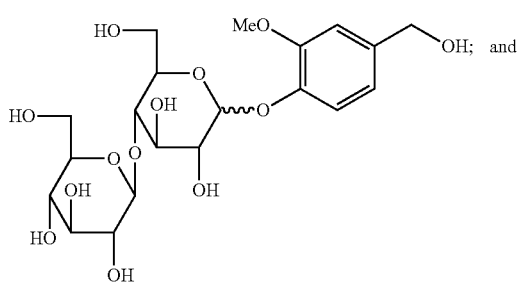
(XIII)

(step c) reacting the compound represented by the formula (XII) or (XIII) with a compound represented by the formula (IV):

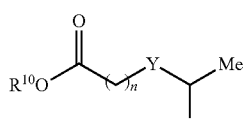
(IV)

wherein $R^{10}$ is a hydrogen atom or a $C_{1-6}$ alkyl group,
Y is an ethylene group or a vinylene group,
R is a hydrogen atom or a methyl group, and
n is an integer of 3 to 5, or a salt thereof.

(23) A method of promoting GLP-1 secretion in a mammal, comprising administering an effective amount of the compound described in any one of (1)-(9) to the mammal.

(24) Use of the compound described in any one of (1)-(9) for the manufacture of a GLP-1 secretion promoting agent.

(25) A compound represented by the formula (XV-1):

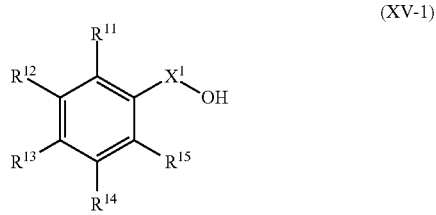

(XV-1)

wherein $R^{11}$, $R^{12}$, $R^{13}$, $R^{14}$ and $R^{15}$ are each independently a hydrogen atom, a hydroxyl group, a $C_{1-6}$ alkyl group, a $C_{1-6}$ alkoxy group, a $C_{1-6}$ alkyl-carbonyloxy group or a G-O— group, and at least one of $R^{11}$, $R^{12}$, $R^{13}$, $R^{14}$ and $R^{15}$ is a G-O— group, wherein G is a saccharide residue, including a saccharide residue having protecting group(s), and $X^1$ is a single bond, or a methylene group, an ethylene group, a trimethylene group, a vinylene group or —CH=CH—CH$_2$—, excluding the following compounds:

(1) a compound wherein $R^{13}$ is a G-O— group, G is a glucosyl group, $R^{11}$, $R^{12}$, $R^{14}$ and $R^{15}$ are each a hydrogen atom, and $X^1$ is a methylene group or an ethylene group, (2) a compound wherein $R^{13}$ is a G-O— group, G is a glucosyl group, $R^{12}$ is a hydroxyl group, $R^{11}$, $R^{14}$ and $R^{15}$ are each a hydrogen atom, and $X^1$ is a methylene group, (3) a compound wherein $R^{13}$ is a G-O— group, G is a glucosyl group, $R^{12}$ is a methoxy group, $R^{11}$, $R^{14}$ and $R^{15}$ are each a hydrogen atom, and $X^1$ is a methylene group or an ethylene group, (4) a compound wherein $R^{13}$ is a G-O— group, G is a glucosyl group, $R^{12}$ and $R^{14}$ are each a methoxy group, $R^{11}$ and $R^{15}$ are each a hydrogen atom, and $X^1$ is a methylene group or an ethylene group, (5) a compound wherein $R^{13}$ is a G-O— group, G is a maltosyl group, $R^{11}$, $R^{12}$, $R^{14}$ and $R^{15}$ are each a hydrogen atom, and $X^1$ is a methylene group, (6) a compound wherein $R^{11}$ is a G-O— group, G is a glucosyl group or a maltosyl group, $R^{12}$, $R^{13}$, $R^{14}$ and $R^{15}$ are each a hydrogen atom, and $X^1$ is a methylene group, and (7) a compound wherein $R^{11}$ is a G-O— group, G is a glucosyl group, $R^{12}$ is a hydroxyl group or a methoxy group, $R^{13}$, $R^{14}$ and $R^{15}$ are each a hydrogen atom, and $X^1$ is a methylene group.

(26) A compound represented by the formula (XVII-1), or a salt thereof:

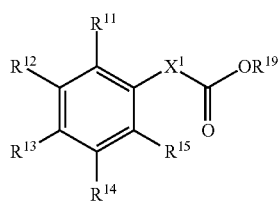

(XVII-1)

wherein $R^{11}$, $R^{12}$, $R^{13}$, $R^{14}$ and $R^{15}$ are each independently a hydrogen atom, a hydroxyl group, a $C_{1-6}$ alkyl group, a $C_{1-6}$ alkoxy group, a $C_{1-6}$ alkyl-carbonyloxy group or a G-O— group, and at least one of $R^{11}$, $R^{12}$, $R^3$, $R^{14}$ and $R^{15}$ is a G-O— group, wherein G is a saccharide residue, including a saccharide is residue having protecting group(s), $X^1$ is a single bond, or a methylene group, an ethylene group, a trimethylene group, a vinylene group or —CH=CH—CH$_2$—, and $R^{19}$ is a hydrogen atom or a $C_{1-6}$ alkyl group, excluding the following compounds:

(1) a compound wherein $R^{13}$ is a G-O— group, G is a glucosyl group or a mannosyl group, $R^{11}$, $R^{12}$, $R^{14}$ and $R^{15}$ are each a hydrogen atom, $X^1$ is a methylene group, and $R^{19}$ is a hydrogen atom, (2) a compound wherein $R^{13}$ is a G-O— group, G is a glucosyl group, $R^{11}$ is a hydroxyl group, $R^{12}$, $R^{14}$ and $R^{15}$ are each a hydrogen atom, $X^1$ is a methylene group, and $R^{19}$ is a hydrogen atom, (3) a compound wherein $R^{13}$ is a G-O— group, G is a glucosyl group, $R^{12}$ is a methoxy group, $R^{11}$, $R^{14}$ and $R^{15}$ are each a hydrogen atom, $X^1$ is a methylene group or an ethylene group, and $R^{19}$ is a hydrogen atom, and (4) a compound wherein $R^{13}$ is a G-O— group, G is a glucosyl group, $R^{11}$, $R^{12}$, $R^{14}$ and $R^{15}$ are each a hydrogen atom, $X^1$ is an ethylene group, and $R^{19}$ is a hydrogen atom.

(27) At least one compound selected from the group consisting of

O-[4-(β-D-glucopyranosyloxy)-3-methoxybenzyl]-8-methylnonanoic acid ester,

O-[4-(β-D-glucopyranosyl-(1→4)-β-D-glucopyranosyloxy)-3-methoxybenzyl]-8-methylnonanoic acid ester, O-[4-(β-D-glucopyranosyloxy)-3-methoxybenzyl]-decanoic acid ester, O-[4-(β-D-glucopyranosyloxy)-3-methoxybenzyl]-7-methyloctanoic acid ester, O-[4-(β-D-glucopyranosyloxy)-3-methoxybenzyl]-8-methyl-6-nonenoic acid ester, O-8-methylnonyl-2-[4-(β-D-glucopyranosyl-(1→4)-β-D-glucopyranosyloxy)-3-methoxyphenyl]acetic acid ester, O-[4-(β-D-glucopyranosyl-(1→4)-β-D-glucopyranosyloxy)-3-methoxyphenethyl]-8-methylnonanoic acid ester, O-[2-(β-D-glucopyranosyl-(1→4)-β-D-glucopyranosyloxy)-3-methoxybenzyl]-8-methylnonanoic acid ester, O-[4-(β-D-maltotriosyloxy)-3-methoxybenzyl]-8-methylnonanoic acid ester, O-[4-(β-D-maltotriosyloxy)-3-methoxybenzyl]-n-hexanoic acid ester, O-[4-(β-D-glucopyranosyloxy)-3-methoxybenzyl]-3-cyclohexylpropionic acid ester, O-8-methylnonyl-3-[4-(β-D-glucopyranosyloxy)-3-methoxyphenyl]propionic acid ester, O-[4-(β-D-glucopyranosyl-(1→4)-β-D-glucopyranosyloxy)-3-methoxybenzyl]-n-tridecanoic acid ester, O-8-methylnonyl-3-[4-(β-D-glucopyranosyl-(1→4)-β-D-glucopyranosyloxy)-3-methoxyphenyl]propionic acid ester, O-[3-(β-D-glucopyranosyl-(1→4)-β-D-glucopyranosyloxy)-4-methoxybenzyl]-8-methylnonanoic acid ester, O-[3-(β-D-glucopyranosyloxy)-4-methoxybenzyl]-8-methylnonanoic acid ester, O-[4-(β-D-glucopyranosyl-(1→4)-β-D-glucopyranosyloxy)-3-methoxybenzyl]-8-methyl-6-nonenoic acid ester, O-[4-(β-D-glucopyranosyl-(1→4)-β-D-glucopyranosyloxy)-3-methoxybenzyl]-7-methyloctanoic acid ester, O-[4-(β-D-glucopyranosyl-(1→4)-β-D-glucopyranosyloxy)-3-methoxybenzyl]-n-propionic acid ester, O-[4-(β-D-glucopyranosyl-(1→4)-β-D-glucopyranosyloxy)-3-methoxybenzyl]-n-hexanoic acid ester,
O-[4-(β-D-maltotriosyloxy)-3-methoxyphenethyl]-8-methylnonanoic acid ester,
O-[4-(β-D-maltotriosyloxy)-3-methoxyphenethyl]-n-hexanoic acid ester,
O-[4-(β-D-maltosyloxy)-3-methoxybenzyl]-n-hexanoic acid ester,
O-[4-(β-D-maltosyloxy)-3-methoxybenzyl]-8-methylnonanoic acid ester,
O-3-[4-(β-D-glucopyranosyl-(1→4)-β-D-glucopyranosyloxy)-3-methoxyphenyl]-2-propenyl-8-methylnonanoic acid ester,
O-[4-(α-L-rhamnosyloxy)-3-methoxybenzyl]-n-hexanoic acid ester, and
O-[4-(α-L-rhamnosyloxy)-3-methoxybenzyl]-8-methylnonanoic acid ester.

(28) At least one compound selected from the group consisting of
O-[4-(β-D-glucopyranosyloxy)-3-methoxybenzyl]-8-methylnonanoic acid ester,
O-[4-(β-D-glucopyranosyl-(1→4)-β-D-glucopyranosyloxy)-3-methoxybenzyl]-8-methylnonanoic acid ester,
O-[4-(β-D-glucopyranosyloxy)-3-methoxybenzyl]-decanoic acid ester,
O-[4-(β-D-glucopyranosyloxy)-3-methoxybenzyl]-7-methyloctanoic acid ester,
O-[4-(β-D-glucopyranosyloxy)-3-methoxybenzyl]-8-methyl-6-nonenoic acid ester,
O-8-methylnonyl-2-[4-(β-D-glucopyranosyl-(1→4)-β-D-glucopyranosyloxy)-3-methoxyphenyl]acetic acid ester,
O-[4-(β-D-glucopyranosyl-(1→4)-β-D-glucopyranosyloxy)-3-methoxyphenethyl]-8-methylnonanoic acid ester,
O-[2-(β-D-glucopyranosyl-(1→4)-β-D-glucopyranosyloxy)-3-methoxybenzyl]-8-methylnonanoic acid ester,
O-8-methylnonyl-3-[4-(β-D-glucopyranosyloxy)-3-methoxyphenyl]propionic acid ester,
O-8-methylnonyl-3-[4-(β-D-glucopyranosyl-(1→4)-β-D-glucopyranosyloxy)-3-methoxyphenyl]propionic acid ester,
O-[3-(β-D-glucopyranosyl-(1→4)-β-D-glucopyranosyloxy)-4-methoxybenzyl]-8-methylnonanoic acid ester,
O-[3-(β-D-glucopyranosyloxy)-4-methoxybenzyl]-8-methylnonanoic acid ester,
O-[4-(β-D-glucopyranosyl-(1→4)-β-D-glucopyranosyloxy)-3-methoxybenzyl]-8-methyl-6-nonenoic acid ester, and
O-[4-(β-D-glucopyranosyl-(1→4)-β-D-glucopyranosyloxy)-3-methoxybenzyl]-7-methyloctanoic acid ester.

(29) O-[4-(β-D-glucopyranosyloxy)-3-methoxybenzyl]-8-methylnonanoic acid ester.
(30) O-[4-(β-D-glucopyranosyl-(1→4)-β-D-glucopyranosyloxy)-3-methoxybenzyl]-8-methylnonanoic acid ester.
(31) O-[4-(β-D-glucopyranosyloxy)-3-methoxybenzyl]-decanoic acid ester.
(32) O-[4-(β-D-glucopyranosyloxy)-3-methoxybenzyl]-7-methyloctanoic acid ester.
(33) O-[4-(β-D-glucopyranosyloxy)-3-methoxybenzyl]-8-methyl-6-nonenoic acid ester.
(34) O-8-methylnonyl-2-[4-(β-D-glucopyranosyl-(1→4)-β-D-glucopyranosyloxy)-3-methoxyphenyl]acetic acid ester.
(35) O-[4-(β-D-glucopyranosyl-(1→4)-β-D-glucopyranosyloxy)-3-methoxyphenethyl]-8-methylnonanoic acid ester.
(36) O-[2-(β-D-glucopyranosyl-(1→4)-β-D-glucopyranosyloxy)-3-methoxybenzyl]-8-methylnonanoic acid ester.
(37) O-8-methylnonyl-3-[4-(β-D-glucopyranosyloxy)-3-methoxyphenyl]propionic acid ester.
(38) O-8-methylnonyl-3-[4-(β-D-glucopyranosyl-(1→4)-3-D-glucopyranosyloxy)-3-methoxyphenyl]propionic acid ester.
(39) O-[3-(β-D-glucopyranosyl-(1→4)-β-D-glucopyranosyloxy)-4-methoxybenzyl]-8-methylnonanoic acid ester.
(40) O-[3-(β-D-glucopyranosyloxy)-4-methoxybenzyl]-8-methylnonanoic acid ester.
(41) O-[4-(β-D-glucopyranosyl-(1→4)-β-D-glucopyranosyloxy)-3-methoxybenzyl]-8-methyl-6-nonenoic acid ester.
(42) O-[4-(β-D-glucopyranosyl-(1→4)-β-D-glucopyranosyloxy)-3-methoxybenzyl]-7-methyloctanoic acid ester.

The present invention has made it possible to provide a novel solid compound, which is completely free of a pungent taste even at a high concentration use, shows excellent stability even in various use conditions, and shows a remarkable GLP-1 secretion enhancing effect.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:
FIG. 13 shows the schemes of Examples 5 to 7.

DETAILED DESCRIPTION OF THE PREFERRED EMBODIMENTS

Figure 1:
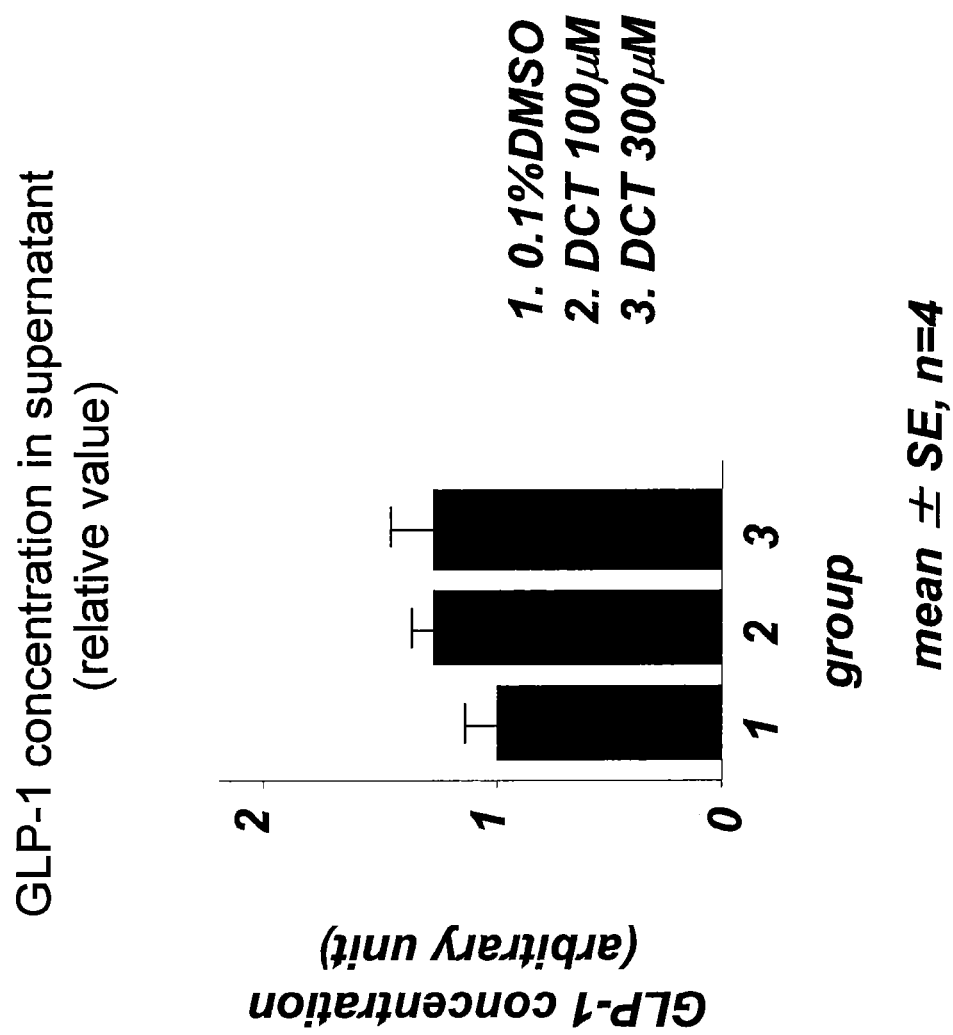
FIG. 1 is a graph showing the measurement results of the GLP-1 concentration in a supernatant in Experimental Example 1.

The present invention relates to compounds represented by the formula (I''). The present invention is explained in detail in the following.

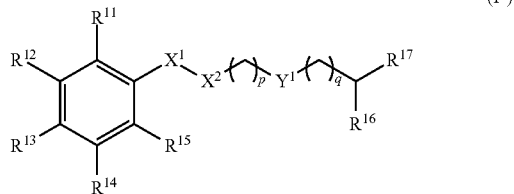

(I'')

wherein $R^{11}$, $R^{12}$, $R^{13}$, $R^{14}$ and $R^{15}$ are each independently a hydrogen atom, a hydroxyl group, a $C_{1-6}$ alkyl group, a $C_{1-6}$ alkoxy group, a $C_{1-6}$ alkyl-carbonyloxy group or a G-O— group, and at least one of $R^{11}$, $R^{12}$, $R^{13}$, $R^{14}$ and $R^{15}$ is a G-O— group, wherein G is a saccharide residue, $X^1$ is a single bond, or a methylene group, an ethylene group, a trimethylene group, a vinylene group or —CH=CH—CH$_2$—, $X^2$ is —CO—O— or —O—CO—, p and q are each an integer of 0 to 7, which satisfy a relationship of p+q=0 to 8, $Y^1$ is a methylene group, an ethylene group or an alkenylene group having a carbon number of 2 to 15 and 1 to 3 double bonds, wherein the double bond may be any of cis and trans, and $R^{16}$ and $R^{17}$ are each independently a hydrogen atom, a methyl group or an ethyl group, or $R^{16}$ and $R^{17}$ form a $C_{3-6}$ cycloalkane together with the carbon atom bonded thereto.

The saccharide residue means a part of a saccharide other than a hemiacetal hydroxyl group. Moreover, the saccharide residue includes a saccharide residue having protecting group(s), i.e., a saccharide derivative having protecting group(s) at hydroxyl group(s) other than a hemiacetal hydroxyl group. Examples of the saccharide residue include monosaccharide residues such as glucosyl group, galactosyl group, xylosyl group, mannosyl group, rhamnosyl group and the like, disaccharide residues such as cellobiosyl group, maltosyl group and the like, trisaccharide residues such as maltotriosyl group and the like, tetrasaccharide residues such as maltotetraosyl group and the like, and pentasaccharide residues such as maltopentaosyl group and the like. Preferably, G is a glucosyl group, a rhamnosyl group, a cellobiosyl group, a maltosyl group or a maltotriosyl group, more preferably a glucosyl group or a cellobiosyl group, more preferably a glucosyl group. In the glycoside of the present invention, the bond between saccharide residue and aglycone may be any of α-bond and β-bond, or a mixture of α-bond glycoside and β-bond glycoside. Preferably, it is β-bond glycoside. A mixture of α-bond glycoside and β-bond glycoside may have any ratio of the α form and the β form. For example, the α form β form ratio is preferably 100:1-1:100, more preferably 75:1-1:75, still more preferably 50:1-1:50.

Examples of the hydroxyl-protecting group include a $C_{1-6}$ alkyl-carbonyl group (e.g., acetyl group, propionyl group, pivaloyl group etc.), a $C_{7-12}$ aralkyl group (e.g., benzyl group etc.), a $C_{6-12}$ aryl-carbonyl group (e.g., benzoyl group etc.), a tri($C_{1-6}$ alkyl)silyl group (e.g., trimethylsilyl group, triethylsilyl group, triisopropylsilyl group, tert-butyldimethylsilyl group etc.), a tri($C_{7-12}$ aralkyl)silyl group, a di($C_{6-12}$ aryl)($C_{1-6}$ alkyl)silyl group (e.g., tert-butyldiphenylsilyl group etc.) and the like. In view of high usefulness at a low cost, a $C_{1-6}$ alkyl-carbonyl group (e.g., acetyl group, propionyl group, pivaloyl group etc.) and a $C_{7-12}$ aralkyl group (e.g., benzyl group) are preferable, an acetyl group and a benzyl group are more preferable, and an acetyl group is still more preferable.

The $C_{1-6}$ alkyl group means a straight chain or branched alkyl group having a carbon number of 1 to 6. For example, a methyl group, an ethyl group, a propyl group, a butyl group, a pentyl group, a hexyl group, an isopropyl group, an isobutyl group, a sec-butyl group, a tert-butyl group, an isopentyl group, a tert-pentyl group, a neopentyl group and the like can be mentioned. Preferred is a methyl group.

The $C_{1-6}$ alkoxy group means a straight chain or branched alkoxy group having a carbon number of 1 to 6. For example, a methoxy group, an ethoxy group, a propoxy group, a butoxy group, a pentyloxy group, a hexyloxy group, an isopropoxy group, an isobutoxy group, a sec-butoxy group, a tert-butoxy group, an isopentyloxy group, a tert-pentyloxy group, a neopentyloxy group and the like can be mentioned. Preferred is a methoxy group.

The $C_{1-6}$ alkyl-carbonyloxy group means an alkyl-carbonyloxy group wherein the alkyl moiety is a straight chain or branched alkyl group having a carbon number of 1 to 6. For example, an acetyloxy group, a propanoyloxy group, a butanoyloxy group, a 2-methylpropanoyloxy group, a pentanoyloxy group, a 3-methylbutanoyloxy group, a 2,2-dimethylpropanoyloxy group, a hexanoyloxy group and the like can be mentioned. Preferred is an acetyloxy group.

Examples of the alkenylene group having a carbon number of 2 to 15 and 1 to 3 double bonds include vinylene, —CH=CH—CH=CH—, —CH=CH—CH=CH—CH=CH—, and the like. Here, the double bond may be any of cis and trans. A trans double bond is preferable.

The $C_{3-6}$ cycloalkane means cycloalkane having a carbon number of 3 to 6. For example, cyclopropane, cyclobutane, cyclopentane and cyclohexane can be mentioned. Preferred is cyclohexane.

As a salt of the compound represented by the formula (XVI), (XVII), (XVII-1) or (IV), salts with alkali metals such as sodium, potassium and the like, and salts with alkaline earth metals such as calcium, magnesium and the like can be mentioned.

$R^{11}$, $R^{12}$ and $R^{13}$ are preferably in the following combinations.

$R^{11}$ is a hydrogen atom, $R^{12}$ is a methoxy group, and $R^{13}$ is a G-O— group, or $R^{11}$ is a G-O— group, $R^{12}$ is a methoxy group, and $R^{13}$ is a hydrogen atom, or $R^{11}$ is a hydrogen atom, $R^{12}$ is a G-O— group, and $R^{13}$ is a methoxy group, wherein G is a saccharide residue.

$R^{14}$ and $R^{15}$ are preferably hydrogen atoms.

$X^1$ is preferably a methylene group, an ethylene group or —CH=CH—CH$_2$—, more preferably a methylene group or an ethylene group.

p and q are each preferably an integer of 0 to 7, which satisfy a relationship of p+q=2 to 8.

$Y^1$ is preferably a methylene group, an ethylene group or a vinylene group, more preferably an ethylene group or a vinylene group.

$R^{16}$ and $R^{17}$ are each independently preferably a hydrogen atom or a methyl group, or $R^{16}$ and $R^{17}$ form a $C_{3-6}$ cycloalkane together with the carbon atom bonded thereto. $R^{16}$ and $R^{17}$ are each independently more preferably a hydrogen atom or a methyl group.

Preferable examples of the compound represented by the formula (I″) (hereinafter referred to as compound (I″)) include the following compounds.

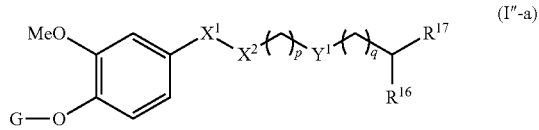

wherein each symbol is as defined above.

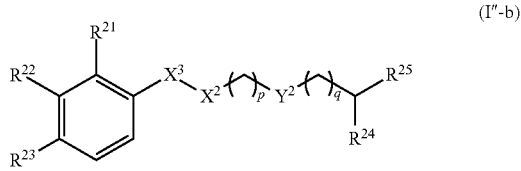

wherein
$R^{21}$ is a hydrogen atom, $R^{22}$ is a methoxy group, and $R^{23}$ is a G-O— group, or
$R^{21}$ is a G-O— group, $R^{22}$ is a methoxy group, and $R^{23}$ is a hydrogen atom, or
$R^{21}$ is a hydrogen atom, $R^{22}$ is a G-O— group, and $R^{23}$ is a methoxy group, wherein G is a saccharide residue,
$X^3$ is a methylene group, an ethylene group or —CH═CH—CH$_2$—,
$X^2$ is —CO—O— or —O—CO—,
p and q are each an integer of 0 to 7, which satisfy a relationship of p+q=0 to 8,
$Y^2$ is a methylene group, an ethylene group or a vinylene group,
$R^{24}$ and $R^{25}$ are each independently a hydrogen atom or a methyl group, or $R^{24}$ and $R^{25}$ form a $C_{3-6}$ cycloalkane together with the carbon atom bonded thereto.

A compound of the formula (I″), wherein $R^{11}$, $R^{12}$, $R^{13}$, $R^{14}$ and $R^{15}$ are each independently a hydrogen atom, a hydroxyl group, a $C_{1-6}$ alkyl group, a $C_{1-6}$ alkoxy group, a $C_{1-6}$ alkyl-carbonyloxy group or a G-O— group, and at least one of $R^{11}$, $R^{12}$, $R^{13}$, $R^{14}$ and $R^{15}$ is a G-O— group, wherein G is a saccharide residue,
$X^1$ is a single bond, or a methylene group, an ethylene group, a trimethylene group or a vinylene group,
$X^2$ is —CO—O— or —O—CO—,
p and q are each an integer of 0 to 7, which satisfy a relationship of p+q=2 to 8,
$Y^1$ is an ethylene group or an alkenylene group having a carbon number of 2 to 15 and 1 to 3 double bonds, wherein the double bond may be any of cis and trans, and
$R^{16}$ and $R^{17}$ are each independently a hydrogen atom, a methyl group or an ethyl group is also preferred.

More preferable examples of compound (I″) include the compounds 3, 4, 11, 12, 15, 16, 17, 18, 19, 20, 22, 22-1, 23, 23-2, 24, 24-2, 25, 26, 29, 29-2, 30, 30-2, 31, 31-2, 32, 32-2, 32-3, 33, 33-4, 34, 34-1, 35, 35-2, 36, 36-2, 38, 38-2, 39, 40, 40-3, 41, 42, 42-4, 44, 44-3, 45, 45-4 and 46 described in the below-mentioned Examples.

Still more preferable examples of compound (I″) include the compounds 4, 12, 16, 18, 20, 22, 23, 24, 24-2, 30, 32, 32-3, 33, 34, 35 and 36 described in the below-mentioned Examples.

Particularly preferable examples of compound (I″) include the compounds 4, 12, 16, 18 and 20 described in the below-mentioned Examples.

Preferable examples of the compound represented by the formula (I′) (hereinafter to be referred to as compound (I′)) include the following compounds.

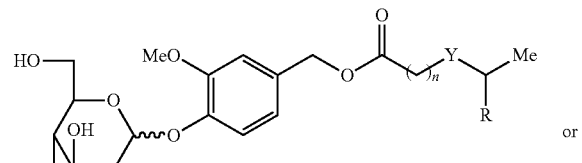

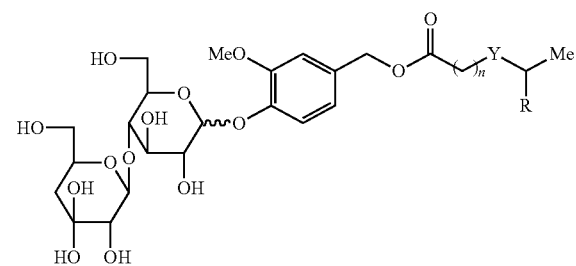

wherein Y is an ethylene group or a vinylene group,
R is a hydrogen atom or a methyl group, and
n is an integer of 3 to 5.

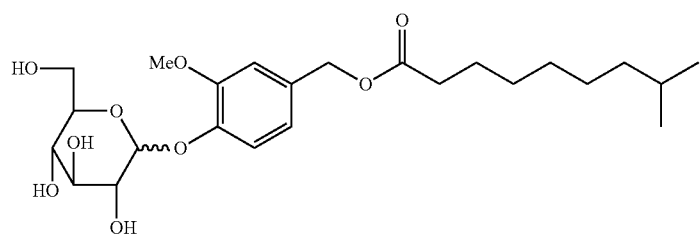

-continued

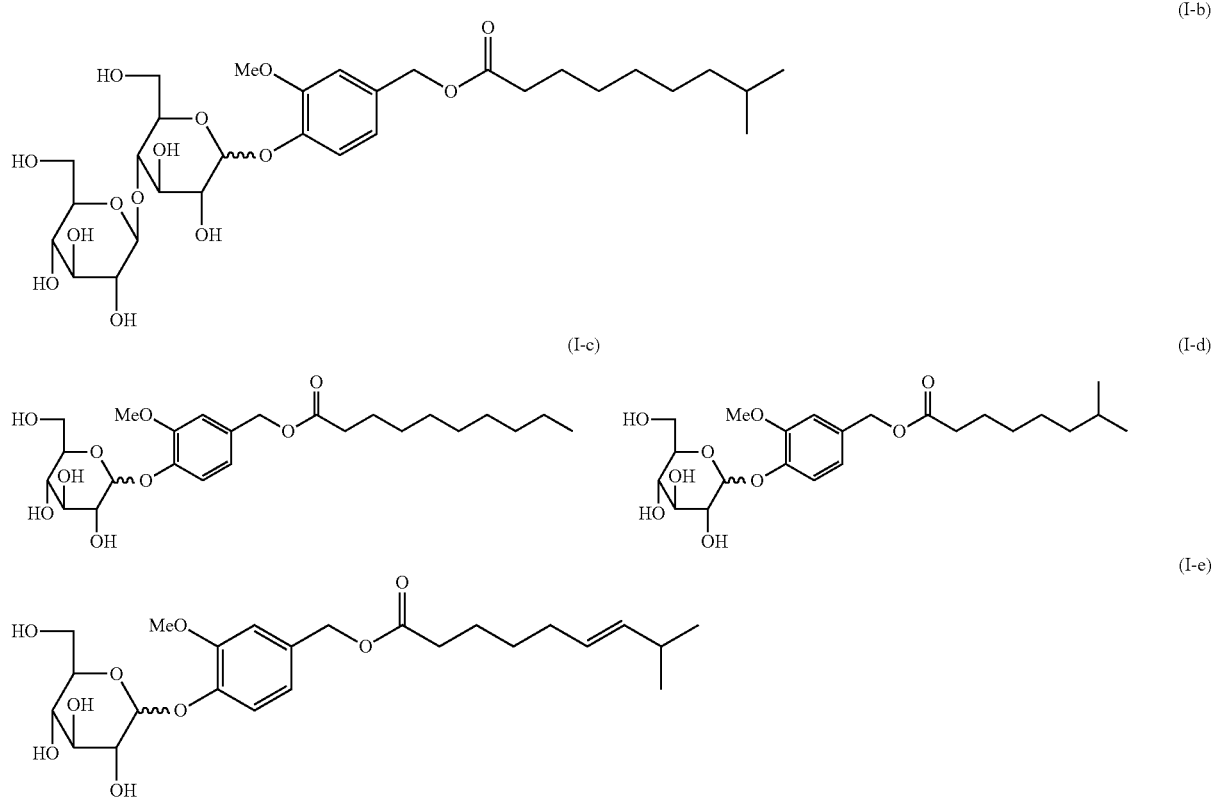

While the compound of the present invention is not particularly limited, it may be produced by a chemical synthesis method, or may be extracted from a particular plant. Since the safety is ensured from the food experience, a compound extracted from a plant is preferable, a compound extracted from a plant of Solanales order is more preferable, a compound extracted from a plant of the Solanaceae family is still more preferable, a compound extracted from a plant of Capsiceae tribe is further more preferable, and a compound extracted from a plant of the *Capsicum* genus is especially preferable.

While the plant of the *Capsicum* genus is not particularly limited, specific examples include chili pepper (*Capsicum annuum* L., *Capsicum chinense*), bell pepper and the like, and nonpungent *Capsicum annuum* L. "CH-19 Sweet", *Capsicum chinense* "Zavory Hot", "Aji dulce strain 2" and "Belize Sweet" are preferable, and nonpungent *Capsicum annuum* L. "CH-19 Sweet" is more preferable. The presence of the compound of the formula (I-a) in "CH-19 Sweet" has been confirmed by LC-MS, while the absence of the compound of the formula (I-a) in the commercially available products of capsinoid has already been confirmed.

While any part of the above-mentioned plant can be used, a seed or a fruit containing a seed is preferable. A raw natural material of the above-mentioned plant is disrupted, chopped or ground, and added with an extraction solvent or, in view of extraction efficiency, preferably subjected to extraction after a treatment of drying, pulverization and the like. For extraction, a natural material of the plant is immersed in an extraction solvent. To increase the extraction efficiency, stirring or homogenization in an extraction solvent may be performed. The extraction temperature may be room temperature or under heating, appropriately from about 1° C. to a temperature not more than the boiling point of the extraction solvent, 1° C. to 100° C. is preferable, and 20° C. to 90° C. is more preferable. While the extraction time varies depending on the kind of the extraction solvent and extraction temperature, it can be appropriately set, and can be 4 hours to 14 days. The number of extraction times is preferably 1 to 5.

As an extraction solvent, organic solvents, for example, lower alcohol such as methanol, ethanol, propanol, isopropanol and the like; polyvalent alcohol such as 1,3-butanediol, propanediol, dipropanediol, glycerol and the like; ethers such as diethyl ether, dipropyl ether and the like; esters such as ethyl acetate, butyl acetate and the like; ketones such as acetone, ethyl methyl ketone and the like; chloroform, dichloromethane, acetonitrile, hexane and the like can be used, and one or more kinds can be selected therefrom and used.

Of the above-mentioned extraction solvents, an organic solvent, or a mixed solvent of an organic solvent and water can be preferably used in the present invention. As the organic solvent, lower alcohol, 1,3-butanediol, glycerol, ethers, acetone, acetonitrile, esters and hexane can be preferably used, and one or more kinds can be selected therefrom and used. As lower alcohol, methanol and ethanol are preferable, as ethers, diethyl ether is preferable, and as esters, ethyl acetate is preferable.

When purification is performed thereafter as necessary, chromatography using a reversed-phase resin wherein carbon chains having a carbon number of 1 to 30 are bonded, a normal phase resin using silica gel as a carrier, a polystyrene synthetic adsorbent (DIAION HP20, HP21, SEPABEADS SP825, SP850, SP70, SP700), a polystyrene synthetic adsorbent (SEPABEADS SP207), and a methacrylic synthetic adsorbent (DIAION HP1MG, HP2MG) can be performed. As the elution solvent usable for the above chromatography, water, and organic solvents, for example, lower alcohols such as methanol, ethanol, propanol, isopropanol and the like; polyvalent alcohols such as 1,3-butanediol, propanediol, dipropanediol, glycerol and the like; ethers such as diethyl ether, dipropyl ether and the like; esters such as ethyl acetate, butyl acetate and the like; ketones such as acetone, ethyl methyl ketone and the like; chloroform, dichloromethane, acetonitrile, hexane and the like can be used, and one or more kinds can be selected therefrom and used. In addition, saline, phosphate buffer, phosphate buffered saline and the like can also be used.

A production method of the compound of the present invention by a particular chemical synthesis method is explained below.

Production Method 1.

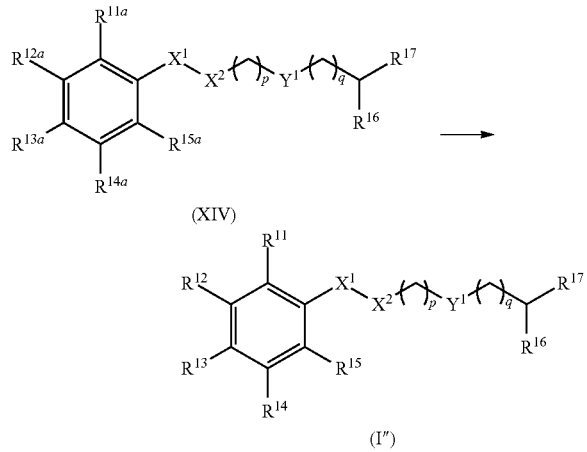

wherein $R^{11a}$, $R^{12a}$, $R^{13a}$, $R^{14a}$ and $R^{15a}$ are each independently a hydrogen atom, a hydroxyl group, a $C_{1-6}$ alkyl group, a $C_{1-6}$ alkoxy group or $C_{1-6}$ alkyl-carbonyloxy group, and at least one of $R^{11a}$, $R^{12a}$, $R^{13a}$, $R^{14a}$ and $R^{15a}$ is a hydroxyl group, $R^{11}$, $R^{12}$, $R^{13}$, $R^{14}$ and $R^{15}$ are each independently a hydrogen atom, a hydroxyl group, a $C_{1-6}$ alkyl group, a $C_{1-6}$ alkoxy group, a $C_{1-6}$ alkyl-carbonyloxy group or a G-O— group, and at least one of $R^{11}$, $R^{12}$, $R^{13}$, $R^{14}$ and $R^{15}$ is a G-O— group, wherein G is a saccharide residue, and other symbols are as defined above.

Compound (I″) can be produced by glycosidating compound (XIV). Glycosidation can be performed by a method using an enzyme such as glycosyl transferase (e.g., glucosyl transferase), or a method by chemical synthesis. For example, it can be performed by a method similar to production method 6, steps 1 and 2, described below.

As compound (XIV) which is a starting compound, capsinoids such as capsiate, dihydrocapsiate, nordihydrocapsiate, vanillyl decanoate and the like, compounds produced by the methods described in WO2007/111276 and WO2008/001912, which are incorporated herein by reference in their entireties, and the like can be used.

Production Method 2.

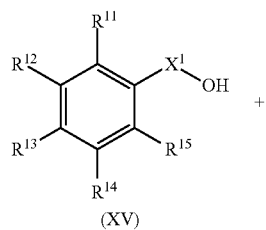

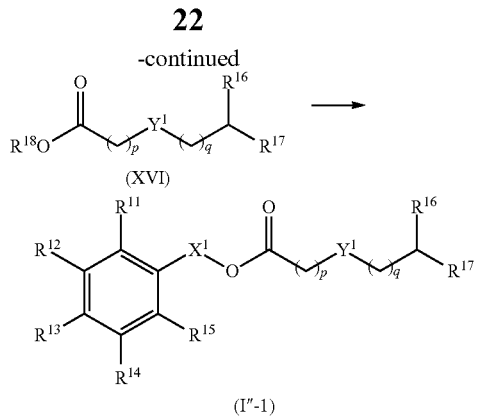

wherein $R^{18}$ is a hydrogen atom or a $C_{1-6}$ alkyl group, and other symbols are as defined above.

Of the compounds represented by the formula (I″), compound (I″-1) wherein $X^2$ is —O—CO— can be produced by esterification of compound (XV) and compound (XVI) or a salt thereof. Esterification can be performed by a known method. For example, it can be performed by a method similar to production method 7, step 5, described below.

Compound (XV) as a starting compound can be produced by, for example, a method similar to production method 7, steps 3 and 4, described below.

Production Method 3.

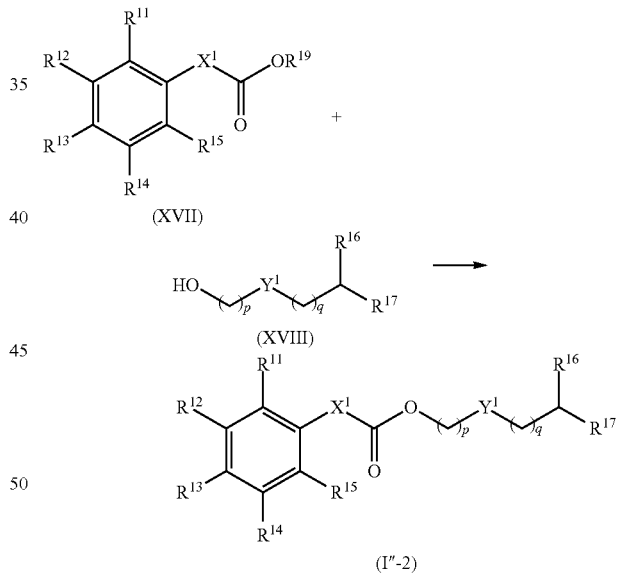

wherein $R^{19}$ is a hydrogen atom or a $C_{1-6}$ alkyl group, and other symbols are as defined above.

Of the compounds represented by the formula (I″), compound (I″-2) wherein $X^2$ is —CO—O— can be produced by esterification of compound (XVII) or a salt thereof and compound (XVIII). Esterification can be performed by a known method. For example, it can be performed by a method similar to production method 7, step 5, described below.

Compound (XVII) as a starting compound can be produced by, for example, a method similar to production method 7, steps 3 and 4, described below.

Production Method 4.

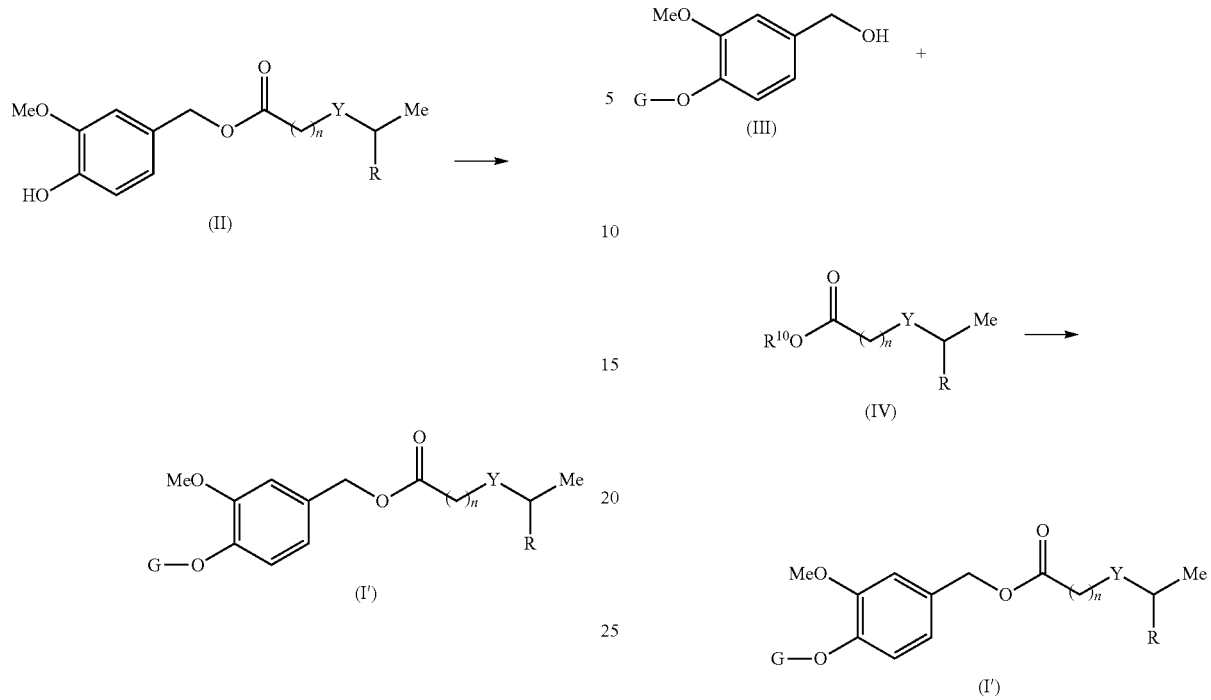

wherein each symbol is as defined above.

Compound (I') can be produced by glycosidating compound (II). Glycosidation can be performed by a method using an enzyme such as glycosyl transferase (e.g., glucosyl transferase), or a method by chemical synthesis. For example, it can be performed by a method similar to production method 6, steps 1 and 2, described below.

As compound (II) which is a starting compound, capsinoids such as capsiate, dihydrocapsiate, nordihydrocapsiate, vanillyl decanoate and the like, compounds produced by the methods described in WO2007/111276 and WO2008/001912, which are incorporated herein by reference in their entireties, and the like can be used.

Production Method 5.

wherein each symbol is as defined above.

Compound (I') can be produced by reacting compound (III) with compound (IV) or a salt thereof. This reaction can be performed by, for example, a method similar to production method 7, step 5, described below.

Compound (III) as a starting compound can be produced by, for example, a method similar to production method 7, steps 3 and 4, described below.

Of the compounds represented by the formula (I'), a compound represented by the formula (I-1) or (I-2) can be produced by production method 6 explained below.

Production method 6.

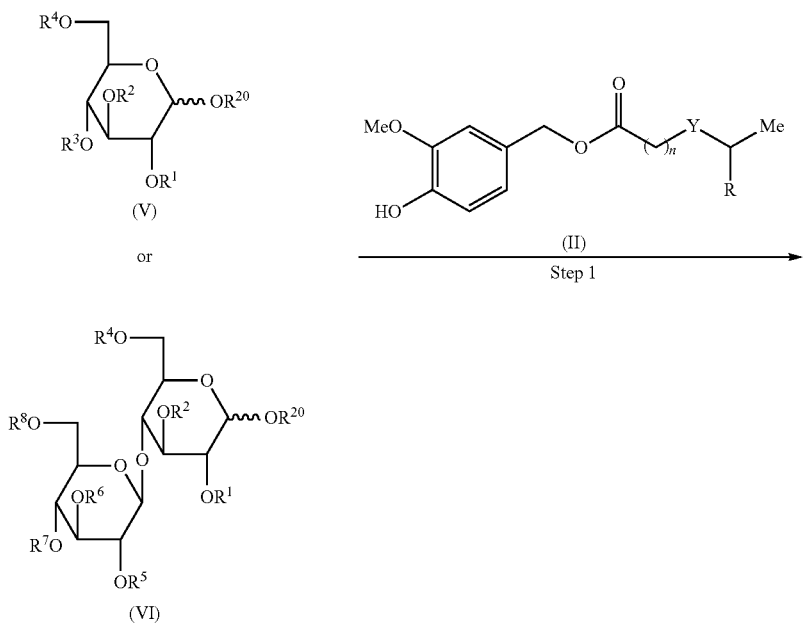

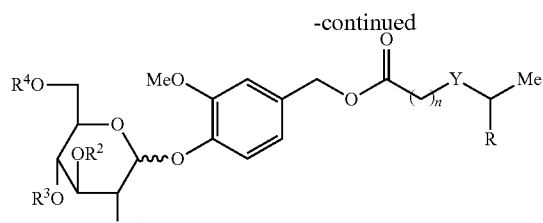

(VII)

or

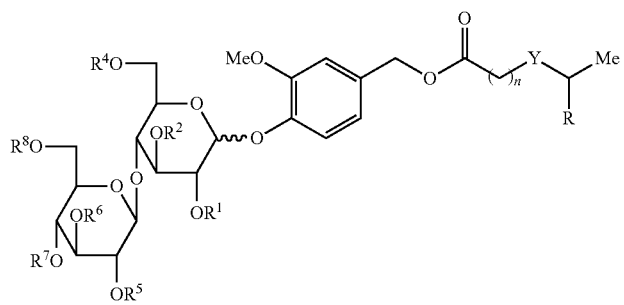

(VIII)

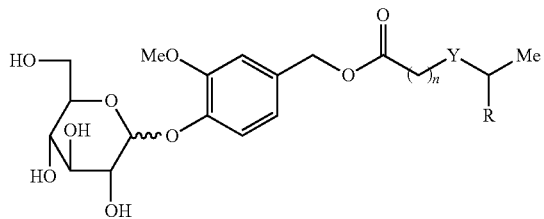

(I-1)

or

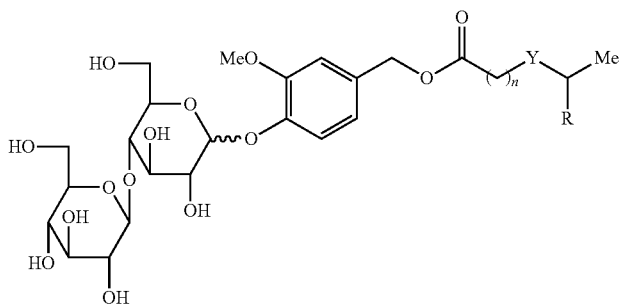

(I-2)

wherein $R^{20}$ is a hydrogen atom or a hydroxyl-protecting group, and other symbols are as defined above.

Step 1

Compound (VII) or (VIII) can be produced by reacting compound (II) with compound (V) or (VI).

When $R^{20}$ is a hydrogen atom, compound (VII) or (VIII) can be produced by subjecting compound (II) and compound (V) or (VI) to a dehydration condensation reaction.

The conditions of dehydration condensation reaction are not particularly limited as long as the reaction proceeds, and it can be preferably performed by Mitsunobu reaction.

The dehydration condensation reaction can be performed by reacting compound (II) with compound (V) or (VI) in the presence of azodicarboxylate and phosphine.

Examples of azodicarboxylate include diethyl azodicarboxylate, dimethyl azodicarboxylate, diisopropyl azodicarboxylate, di-tert-butyl azodicarboxylate, dibenzyl azodicarboxylate, bis(2,2,2-trichloroethyl) azodicarboxylate, 1,1'-(azodicarbonyl)dipiperidine, 1,1'-azobis(N,N-dimethylformamide) and the like.

Examples of phosphine include triphenylphosphine, tributylphosphine, tri-tert-butylphosphine, trihexylphosphine, trioctylphosphine, tricyclohexylphosphine, phenoxydiphenylphosphine, isopropyldiphenylphosphine, diphenyl-2-pyridylphosphine, 4-(dimethylamino)phenyldiphenylphosphine, diethylphenylphosphine, dicyclohexylphenylphosphine and the like.

The amount of compound (V) or (VI) to be used is 0.5 to 3 mol, preferably 1 to 2 mol, per 1 mol of compound (II). The amount of azodicarboxylate to be used is 0.5 to 3 mol, preferably 1 to 2 mol, per 1 mol of compound (II). The amount of phosphine to be used is 0.5 to 3 mol, preferably 1 to 2 mol, per 1 mol of compound (II).

This reaction is preferably performed in a solvent. The solvent is not particularly limited as long as the reaction proceeds and, for example, aromatic hydrocarbons such as toluene, xylene, benzene and the like; ethers such as tetrahydrofuran, tert-butyl methyl ether, diethyl ether and the like; halogenated hydrocarbons such as dichloromethane, 1,2-dichloroethane, chloroform and the like; or a mixture thereof and the like can be mentioned.

While the reaction temperature is not particularly limited as long as the reaction proceeds, the lower limit is preferably not less than 10° C., more preferably not less than 20° C., still more preferably not less than 30° C., further more preferably not less than 40° C. On the other hand, the upper limit is preferably not more than 80° C., more preferably not more than 70° C. While the reaction time is not particularly limited as long as the reaction proceeds, the lower limit is preferably not less than 10 minutes, more preferably not less than 30 minutes, still more preferably not less than 1 hour, further more preferably not less than 2 hours. On the other hand, the upper limit is preferably not more than 72 hours, more preferably not more than 48 hours, still more preferably not more than 24 hours, further more preferably not more than 20 hours.

When $R^{20}$ is a hydroxyl-protecting group, compound (VII) or (VIII) can be produced by reacting compound (II) with compound (V) or (VI) in the presence of a Lewis acid.

Examples of the Lewis acid include $BF_3$, $BF_3.OEt_2$, $BCl_3$, $TiCl_4$, $TiBr_4$, $SnCl_4$, $SbCl_5$, $SbF_5$, $FeCl_3$, $ZnCl_2$, $ZnBr_2$, $AlCl_3$, $AlBr_3$ and the like. Preferably, $BF_3$ or $BF_3.OEt_2$ is used.

The amount of compound (V) or (VI) to be used is 0.5 to 3 mol, preferably 1 to 2 mol, per 1 mol of compound (II). The amount of the Lewis acid to be used is 0.01 to 10 mol, preferably 0.05 to 5 mol, per 1 mol of compound (II).

This reaction is preferably performed in a solvent. While the solvent is not particularly limited as long as the reaction proceeds, for example, halogenated hydrocarbons such as dichloromethane, 1,2-dichloroethane, chloroform and the like; aromatic hydrocarbons such as toluene, xylene, benzene and the like; aliphatic hydrocarbons such as hexane, heptane and the like; or a mixture thereof and the like can be mentioned.

The reaction temperature is −100° C. to 140° C., preferably −80° C. to 80° C. The reaction time is 1 hour to 48 hours, preferably 2 hours to 24 hours.

Step 2

Compound (I-1) or (I-2) can be produced by removing the hydroxyl-protecting groups of compound (VII) or (VIII).

The protecting group can be removed by a method known per se. For example, when the protecting group is a $C_{1-6}$ alkyl-carbonyl group, deprotection can be performed by hydrolysis in the presence of a base. Examples of the base include organic amines such as triethylamine, diisopropylethylamine and the like.

The amount of the base to be used is 5 to 200 mol, preferably 40 to 140 mol, per 1 mol of compound (VII) or (VIII).

This reaction is preferably performed in a solvent. While the solvent is not particularly limited as long as the reaction proceeds, for example, alcohols such as methanol, ethanol, isopropanol and the like; water; or a mixture thereof and the like can be mentioned.

The reaction temperature is 10° C. to 90° C., preferably 50° C. to 70° C. The reaction time is 5 hours to 48 hours, preferably 20 hours to 30 hours.

When the protecting group is a $C_{1-6}$ alkyl-carbonyl group, the $C_{1-6}$ alkyl-carbonyl group can be selectively removed without decomposition of an ester bond of aglycone by deprotection in an alcohol solvent such as methanol, ethanol, isopropanol and the like, in the presence of an enzyme such as lipase and the like. As the lipase, esterases such as deacetylase and the like can be used.

The amount of lipase to be used is 0.001 to 1 g, preferably 0.01 to 0.5 g, per 1 g of compound (VII) or (VIII).

The reaction temperature is 10° C. to 80° C., preferably 25° C. to 70° C. The reaction time is 1 hour to 96 hours, preferably 10 hours to 48 hours.

Compound (V) or (VI) as a starting compound can be produced by reacting commercially available 1,2,3,4,6-penta-O-acetyl-β-D-glucopyranose or α-D-cellobiose octaacetate with ammonium acetate in N,N-dimethylformamide or reacting with benzylamine and the like in tetrahydrofuran.

Of the compounds represented by the formula (I'), a compound represented by the formula (I-1) or (I-2) can be produced by production method 7 explained below.

Production method 7.

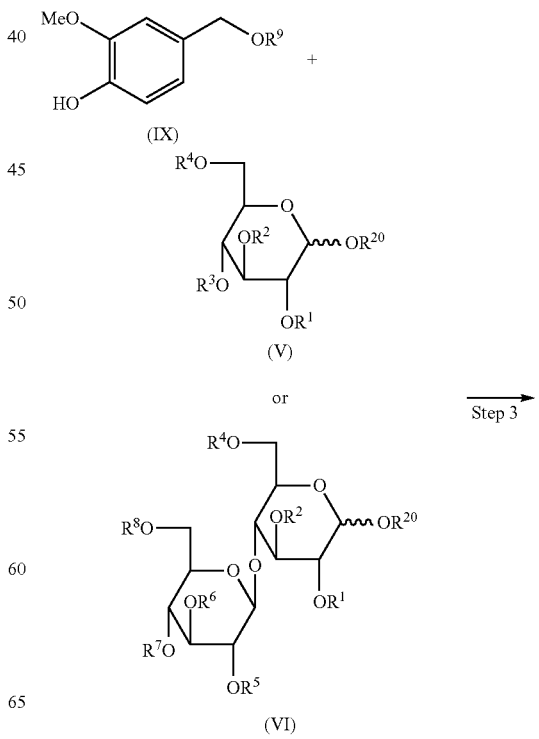

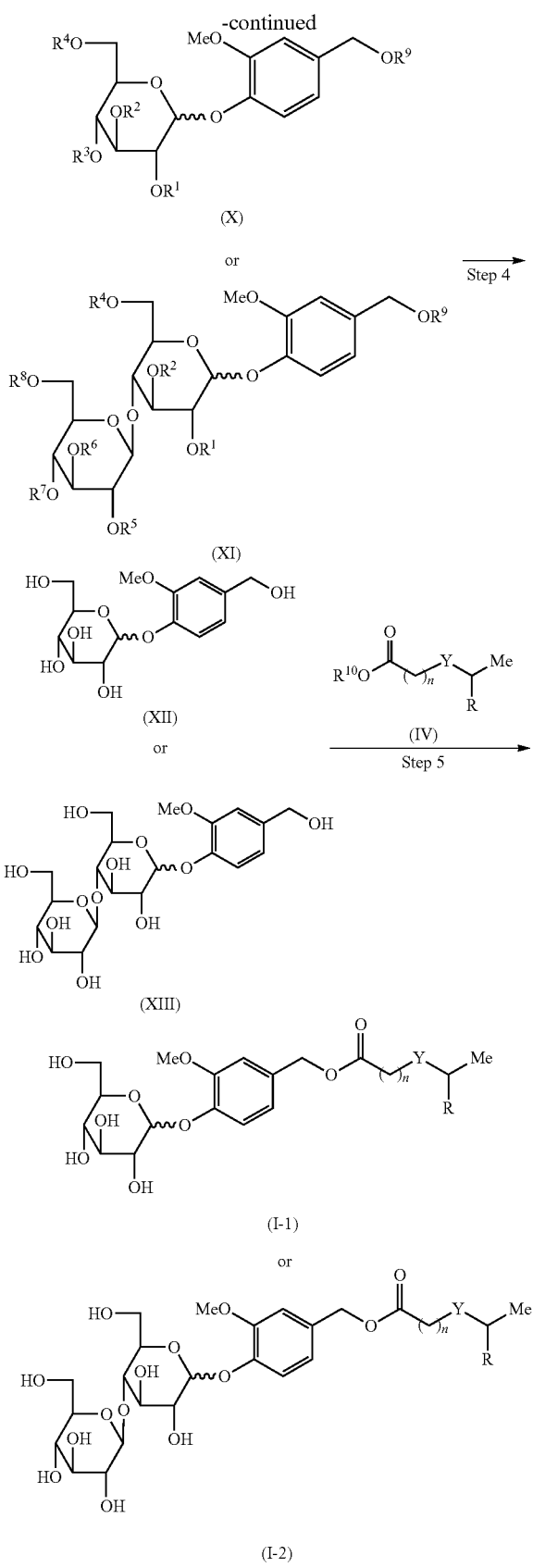

wherein $R^{20}$ is a hydrogen atom or a hydroxyl-protecting group, and other symbols are as defined above.

Step 3

Compound (X) or (XI) can be produced by reacting compound (IX) with compound (V) or (VI).

This reaction can be performed by a method similar to production method 6, step 1.

Step 4

Compound (XII) or (XIII) can be obtained by removing the hydroxyl-protecting groups of compound (X) or (XI).

The protecting group can be removed by a method known per se. For example, when the protecting group is a $C_{1-6}$ alkyl-carbonyl group, deprotection can be performed by hydrolysis in the presence of a base. Examples of the base include metal alkoxides such as sodium methoxide, sodium ethoxide, potassium tert-butoxide and the like; alkali metal hydroxides such as sodium hydroxide, potassium hydroxide and the like; and the like.

The amount of the base to be used is 0.01 to 10 mol, preferably 0.05 to 1 mol, per 1 mol of compound (X) or (XI).

This reaction is preferably performed in a solvent. While the solvent is not particularly limited as long as the reaction proceeds, for example, alcohols such as methanol, ethanol, isopropanol and the like; water; or a mixture thereof and the like can be mentioned.

The reaction temperature is 10° C. to 80° C., preferably 20° C. to 30° C. The reaction time is 30 minutes to 15 hours, preferably 1 hour to 5 hours.

After completion of the reaction, the reaction mixture is neutralized with strong acidic cation exchange resin, the resin is filtered off, and the filtrate is concentrated to give compound (XII) or (XIII).

Step 5

Compound (I-1) or (I-2) can be produced by reacting compound (XII) or (XIII) with compound (IV) or a salt thereof.

This reaction is preferably performed in the presence of esterase, particularly lipase. As lipase, immobilized enzymes such as Novozym 435 (Novozymes A/S), Lipozyme RM IM (Novozymes A/S), lipase PS Amano (Amano Enzyme Inc.) and the like can be used.

When compound (IV) wherein $R^{10}$ is a hydrogen atom is used, a dehydrating agent such as magnesium sulfate and the like is preferably added to the reaction mixture.

The amount of compound (IV) or a salt thereof to be used is 0.5 to 50 mol, preferably 1.0 to 15 mol, per 1 mol of compound (XII) or (XIII). The amount of lipase to be used is 0.001 to 1 g, preferably 0.01 to 0.5 g, per 1 g of compound (XII) or (XIII). The amount of the dehydrating agent to be used is 0.1 to 10 g, preferably 0.5 to 5 g, per 1 g of compound (XII) or (XIII).

While this reaction is preferably performed without solvent, a solvent can also be used. While the solvent is not particularly limited as long as the reaction proceeds, for example, ketones such as acetone, ethyl methyl ketone and the like; esters such as ethyl acetate, isopropyl acetate and the like; ethers such as 1,4-dioxane, tetrahydrofuran, diethyl ether and the like; aromatic hydrocarbons such as benzene, toluene and the like; aliphatic hydrocarbons such as hexane, heptane and the like; or a mixture thereof and the like can be mentioned.

The reaction temperature is 10° C. to 80° C., preferably 25° C. to 70° C. The reaction time is 1 hour to 96 hours, preferably 10 hours to 48 hours.

Compound (IX) as a starting compound wherein $R^9$ is a $C_{1-6}$ alkyl-carbonyl group can be produced by reacting vanillyl alcohol with $C_{1-6}$ alkyl-carboxylic acid ester (e.g., ethyl acetate) in the presence of lipase. This reaction can be performed by a method similar to production method 7, step 5.

The compounds of the present invention have an excellent GLP-1 secretion promoting action and can be used as a GLP-1 secretion promoting agent. A GLP-1 secretion promoting agent can be used as a prophylactic or therapeutic agent for diabetes (particularly type II diabetes), or an anorexigenic agent. When the compound of the present invention is taken before ingestion of a meal, GLP-1 secretion is enhanced, which in turn provides an action of suppressing the appetite itself. In the present invention, the "anorexigenic agent" means a medicament having an action of suppressing the appetite itself, by administering before ingestion of a meal.

The compounds of the present invention have a fat accumulation suppressive action, a sympathetic nerve activating action, and a blood circulation promoting action. In addition, since the compounds of the present invention have a suppressive action on the increase of GPT value, which is a hepatopathy marker, they can also be used as an improving agent for fatty liver caused by an excessive intake of fat.

Since the compounds of the present invention have the above-mentioned effects, they can be used as a pharmaceutical composition, a food composition, or a cosmetic composition. The compounds of the present invention can be contained as a mixture of one or more kinds thereof in the above-mentioned composition.

Since the compounds of the present invention have an excellent GLP-1 secretion promoting action, a food ingestion suppressive action and a GPT value increase-suppressive action, they can be used as a pharmaceutical product for mammals such as human, bovine, horse, dog, mouse, rat and the like. The compounds of the present invention can be administered as is or as a pharmaceutical composition containing the same mixed with a pharmaceutically acceptable carrier according to a method known per se. While oral administration is generally preferable, parenteral administration can also be employed (e.g., routes such as intravenous, subcutaneous, intramuscular, suppository, enema, ointment, patch, sublingual, eye drop, inhalation administrations and the like). While the dose used for the above-mentioned objects is determined according to the desired treatment effect, administration method, duration of treatment, age, body weight and the like, a daily dose of 0.01 mg to 20 g, preferably about 0.1 mg to 10 g for oral administration is generally administered to an adult in one to several portions per day. In addition, the content of the compound of the present invention in the above-mentioned pharmaceutical composition is about 0.01 mass % to 100 mass % of the whole composition.

Examples of the pharmaceutically acceptable carrier for the pharmaceutical composition of the present invention include various organic or inorganic carrier substances conventionally used as preparation materials. For example, excipient, lubricant, binder, disintegrant, water-soluble polymer and basic inorganic salt in solid preparation; solvent, solubilizing agents, suspending agent, isotonicity agent, buffering agent and soothing agent in liquid preparation, and the like can be mentioned. When necessary, general additives such as preservative, antioxidant, colorant, sweetening agent, souring agent, effervescing agent, flavor and the like can also be used.

The dosage form of such pharmaceutical compositions may be tablet, powder, pill, granule, capsule, suppository, solution, sugar-coated agent, depot, syrup, suspension, emulsion, troche, sublingual agent, adhesive preparation, oral disintegrant (tablet), inhalant, enema, ointment, tape and eye drop, and these can be produced using conventional formulation auxiliaries and according to a conventional method.

The pharmaceutical compositions of the present invention can be produced according to a method conventionally used in the technical field of pharmaceutical formulation, for example, the method described in the Japanese Pharmacopoeia and the like. Specific production methods of the preparation are explained in detail in the following.

For example, when the compound of the present invention is prepared as an oral preparation, excipient and, where necessary, binder, disintegrant, lubricant, colorant, flavoring agent and the like are further added and the mixture is processed to give, for example, tablet, powder, pill, granule, capsule, suppository, solution, sugar-coated agent, depot, syrup and the like according to a conventional method. Examples of the excipient include lactose, cornstarch, sucrose, glucose, sorbitol, crystalline cellulose and the like. Examples of the binder include polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone and the like. Examples of the disintegrant include starch, agar, gelatin powder, crystalline cellulose, calcium carbonate, sodium hydrogen carbonate, calcium citrate, dextran, pectin and the like. Examples of the lubricant include magnesium stearate, talc, polyethylene glycol, silica, hydrogenated vegetable oil and the like. As the colorant, one allowed to add to a pharmaceutical product is used, and as the flavoring agent, cocoa powder, menthol, aromatic acid, peppermint oil, borneol, powdered cinnamon bark and the like are used. Where necessary, these tablets and granules are applied with a coating as appropriate such as sugar coating, gelatin coating, and the like.

When an injection is to be prepared, pH adjuster, buffering agent, stabilizer, preservative and the like are added where necessary and the mixture is processed to give subcutaneous, intramuscular or intravenous injection according to a conventional method.

A food composition containing the compound of the present invention is preferably used as a food for suppression of ingestion, an appetite suppressant or a food for diet products. Furthermore, it is preferably used as a food for specified health uses.

The "food" of the present invention means general foods, which include food for specified health uses and food with nutrient function claims defined by Food with Health Claims of Consumer Affairs Agency, Government of Japan, in addition to general foods including so-called health food, and further encompass dietary supplements.

The form of the food composition of the present invention is not particularly limited, and the composition may take any form as long as it can be orally ingested.

Examples thereof include powder, granule, tablet, hard capsules, soft capsule, liquid (drinks, jelly drinks and the like), candy, chocolate and the like, all of which can be produced according to a method known per se in the technical field.

The content of the compound of the present invention in the food composition is appropriately determined to afford an appropriate dose within the indicated range.

For the food composition of the present invention, other food additives can be used as necessary. Examples of such food additive include those generally used as components of health foods such as fruit juice, dextrin, cyclic oligosaccharide, saccharides (monosaccharides such as fructose, glucose and the like, and polysaccharides), acidulant, flavor, powdered green tea and the like, which are used for controlling and improving taste, emulsifier, collagen, whole milk powder, polysaccharide thickener, agar and the like, which are used for improving texture, and further, vitamins, eggshell calcium, calcium pantothenate, the other minerals, royal jelly, propolis, honey, dietary fiber, *Agaricus*, chitin, chitosan, flavonoids, carotenoids, lutein, traditional Japanese herbal medicine, chondroitin, various amino acids, and the like.

A cosmetic composition having a blood circulation enhancing effect, which is also applicable to the sensitive skin, can be produced by adding the compound of the present invention.

The dosage form thereof is not particularly limited, and can take any dosage form such as solution state, paste state, gel state, solid state, powder state and the like. A solid form and a powder form are preferable, since the stability of the compound of the present invention can be further improved.

The cosmetic composition of the present invention can be used as cosmetics for skin and hair, bathwater additives or toiletry products. Examples thereof include oil, lotion, cream, emulsion, gel, shampoo, hair rinse, hair conditioner, enamel, foundation, lipstick, face powder, pack, ointment, granule, capsule, perfume, powder, cologne, toothpaste, soap, aerosol, cleansing foam and the like.

The cosmetic composition of the present invention can be used for pharmaceutical agents or quasi-drugs for the prevention or improvement of various dermatic diseases, such as hair-growth medicine, an agent for antiaging and improving skin, skin essence, an agent for preventing and improving skin roughness due to chapped skin/crack and the like.

Since the amount of the compound of the present invention to be added to a cosmetic composition only needs to be of the level capable of exerting a desired blood circulation improvement effect according to the use form, the lower limit of the amount to be added is preferably not less than 0.0001 mass %, more preferably not less than 0.001 mass %, still more preferably not less than 0.01 mass %, further more preferably not less than 0.03 mass %, and especially preferably not less than 0.1 mass %. On the other hand, since the upper limit of the amount to be added only needs to be of the level sufficient to exert a desired blood circulation improving effect, it is preferably not more than 10 mass %, more preferably not more than 8 mass %, still more preferably not more than 6 mass %, further more preferably not more than 4 mass %, especially preferably not more than 2 mass %, and particularly preferably not more than 1 mass %.

The cosmetic composition of the present invention may concurrently contain conventionally-employed blood circulation enhancers where appropriate. Examples of such blood circulation enhancers include powdered *capsicum, capsicum* tincture, *capsicum* essence, capsaicin, homocapsaicin, homodihydrocapsaicin, vanillyl nonanamide, ginger extract, *capsicum* extract, nicotinic acid, sophorae radix extract, *Astragalus* root extract, *zingiber siccatum* extract, safflower extract, Japanese pepper extract, *Salvia miltiorrhiza* extract, panacis japonici rhizoma extract, ginseng extract, γ-aminobutyric acid (GABA) and the like.

Furthermore, the cosmetic composition of the present invention may contain various components generally used as cosmetic or skin external preparations as long as the effect of the present invention is not inhibited. Examples of such components include oily base, surfactant, polymeric substance, solvent, powder substance, antioxidant, anti-inflammatory agent, UV absorber, skin-lightening agent, cellular stimulant, moisturizing agent, metal chelating agent, dyes, flavor, transdermal absorption enhancer and the like.

Examples of the oily base include hydrocarbons such as squalane, liquid paraffin, light liquid isoparaffin, heavy liquid isoparaffin, microcrystalline wax, solid paraffin and the like, silicones such as dimethicone, phenyldimethicone, cyclomethicone, amodimethicone, polyether-modified silicones and the like, esters such as jojoba oil, carnauba wax, rhus succedanea fruit wax, beeswax, whale wax, octyldodecyl oleate, isopropyl myristate, neopentylglycol diisostearate, diisostearyl malate and the like, fatty acids such as stearic acid, lauric acid, myristic acid, palmitic acid, isostearic acid, isopalmitic acid, behenic acid, oleic acid and the like, acylamino acids such as acyl glutamate, acylglycine, acylalanine, acylsarcosine and the like, higher alcohols such as behenyl alcohol, cetyl alcohol, oleyl alcohol, octadecyl alcohol and the like, triglycerides such as castor oil, coconut oil, hydrogenated coconut oil, camellia Japonica oil, wheatgerm oil, glycelyl triisostearate, glycelyl isooctanoate, olive oil etc., and the like.

Examples of the surfactant include nonionic surfactants such as sorbitan sesquioleate, sorbitan monooleate, sorbitan trioleate, sorbitan sesquistearate, sorbitan monostearate, sorbitan polyoxyethylene monooleate, sorbitan polyoxyethylene monostearate, polyoxyethylene stearate, polyoxyethylene oleate, polyoxyethylene glycerol fatty acid ester, polyoxyethylene alkyl ether, polyoxyethylene hydrogenated castor oil and the like, anionic surfactants such as sodium lauryl stearate, polyoxyethylene alkyl sulfate, sulfosuccinate salt, acylglutamate salt, acylsarcosinate salt, acylglycinate salt, acylalaninate salt and the like, cationic surfactants such as quaternary alkylammonium salt and the like, amphoteric surfactants such as alkylbetaine and the like, emulsifiers, solubilizers and the like.

Examples of the solvent include lower alcohols such as ethanol and the like, polyvalent alcohols such as 1,2-pentanediol, 1,2-hexylene glycol, isoprene glycol and the like, ethers and the other organic solvents, water and the like.

Examples of the polymeric substance include polyamino acids such as polyaspartic acid, ε-polylysine, γ-polyglutamic acid and the like and derivatives thereof, natural polymeric compounds such as collagen, elastin and the like, semisynthetic is polymer compounds such as partially deacetylated chitin and the like, synthetic polymer compounds such as carboxymethylcellulose etc., and the like.

Examples of the powder substance include organic powders such as crystalline cellulose, crosslinking methylpolysiloxane, polyethylene powder, acrylic resin powder and the like, optionally surface-treated powders such as talc, mica, sericite, magnesium carbonate, calcium carbonate, titanium dioxide, iron oxide, iron blue, ultramarine blue, titanium mica, titanium sericite, silica and the like, pearlescent pigments such as hybrid fine powder, titanium dioxide-coated mica and the like, polymer powders such as photochromic pigment, nylon powder and the like, organic powders such as N-ε-lauroyllysine etc., and the like.

Examples of the dye include legal tar dye first category, legal tar dye second category, legal tar dye third category, hair dye, natural dye, mineral dye and the like.

Examples of the flavor include animal flavor such as musk and the like, plant flavors such as jasmine oil and the like, synthetic flavors such as α-amylcinnamaldehyde and the like, blended flavors and the like.

Examples of the transdermal absorption enhancer include urea, 2-pyrrolidone, 1-hexanol, 1-octanol, 1-decanol, 1-menthol, sodium lauryl sulfate, isopropyl myristate, n-hexyl acetate, oleic acid and the like.

Other features of the invention will become apparent in the course of the following descriptions of exemplary embodiments which are given for illustration of the invention and are not intended to be limiting thereof.

EXAMPLES

The schemes of Examples 1 to 29 and Comparative Examples 1 to 3 are shown in FIGS. 12 to 22.

Example 1

2,3,4,6-tetra-O-acetyl-D-glucopyranose (2)

1,2,3,4,6-penta-O-acetyl-β-D-glucopyranose (1) (50.0 g, 128 mmol) was dissolved in N,N-dimethylformamide (120 ml) at room temperature and cooled in an ice bath. To this solution was added ammonium acetate (20.0 g, 260 mmol), the ice bath was removed, and the mixture was stirred at room temperature for 21.5 hours. Since the remainder of the starting material was confirmed by thin layer chromatography (TLC), the reaction mixture was cooled in an ice bath, and ammonium acetate (5.0 g, 65 mmol) was added. Then, the ice bath was removed, the reaction mixture was stirred at room temperature for 3 hours, and the disappearance of the starting material was confirmed by TLC. The reaction container was cooled in an ice bath, water (600 ml) was added slowly, and the ice bath was removed. The mixture was extracted 5 times with diethyl ether (400 ml) at room temperature. The combined organic layer was washed with 15% brine (100 ml), dried over magnesium sulfate, and filtered, and the filtrate was concentrated under reduced pressure. The residue was purified by silica gel column chromatography (gradient; ethyl acetate:n-hexane=40:60→68:32) to give 2,3,4,6-tetra-O-acetyl-D-glucopyranose (2) (38.5 g, 111 mmol, yield 86%) as a colorless transparent oil. As a result of $^1$H-NMR analysis, it was a mixture of α form:β form at a ratio of about 3:2.

$^1$H-NMR (400 MHz, CDCl$_3$) δ: 2.02 (s, 3H), 2.04 (s, 3H), 2.09 (s, 3H), 2.10 (s, 3H), 3.76 (ddd, ½H, J=2.4 Hz, 4.9 Hz, 10.1 Hz), 3.78-3.95 (brs, 1H), 4.01-4.10 (m, ½H), 4.10-4.31 (m, 2H), 4.71-4.79 (m, ½H), 4.86-4.93 (m, 1H), 5.08 (dd, 1H, J=10.1 Hz, 10.1 Hz), 5.25 (dd, ½H, J=10.1 Hz, 10.1 Hz), 5.43-5.49 (m, ½H), 5.54 (dd, ½H, J=10.1 Hz, 10.1 Hz). ESIMS (m/z): 371.1 ([M+Na]$^+$).

O-[4-(2,3,4,6-tetra-O-acetyl-β-D-glucopyranosyloxy)-3-methoxybenzyl]-8-methylnonanoic acid ester (3)

Under an argon atmosphere, 2,3,4,6-tetra-O-acetyl-D-glucopyranose (2) (21.6 g, 62.0 mmol) was dissolved in toluene (160 ml), triphenylphosphine (16.2 g, 61.8 mmol) and dihydrocapsiate (12.0 g, 38.9 mmol) were added at room temperature. Then, the reaction mixture was cooled in an ice bath, and diethyl azodicarboxylate 2.2 M toluene solution (28 ml, 61.6 mmol) was added dropwise. After stirring for 20 minutes, the ice bath was removed and the mixture was warmed to room temperature, and further stirred for 16 hours. The reaction solution was concentrated under reduced pressure, the insoluble material was filtered off, and the filtrate was concentrated under reduced pressure. The residue was purified by silica gel column chromatography (gradient; ethyl acetate:n-hexane=15:85→46:54) to give a mixture of β form O-[4-(2,3,4,6-tetra-O-acetyl-β-D-glucopyranosyloxy)-3-methoxybenzyl]-8-methylnonanoic acid ester (3) and α form (as a result of $^1$H-NMR analysis, β form:α form ratio was about 7:1; 18.9 g, 29.6 mmol, yield 76%) as a pale-yellow oil.

$^1$H-NMR (400 MHz, CDCl$_3$) δ: 0.86 (d, 6H, J=6.6 Hz), 1.10-1.19 (m, 2H), 1.23-1.37 (m, 6H), 1.44-1.58 (m, 1H), 1.64 (tt, 2H, J=7.5 Hz, 7.5 Hz), 2.04 (s, 3H), 2.05 (s, 3H), 2.08 (s, 3H), 2.08 (s, 3H), 2.35 (t, 2H, J=7.5 Hz), 3.77 (ddd, 1H, J=2.5 Hz, 5.0 Hz, 10.0 Hz), 3.83 (s, 3H), 4.17 (dd, 1H, J=2.5 Hz, 12.2 Hz), 4.29 (dd, 1H, J=5.0 Hz, 12.2 Hz), 4.94-4.98 (m, 1H), 5.05 (s, 2H), 5.12-5.22 (m, 1H), 5.26-5.31 (m, 2H), 6.85-6.92 (m, 2H), 7.10 (d, 1H, J=8.1 Hz). ESIMS (m/z): 661.2 ([M+Na]$^+$), 677.2 ([M+K]$^+$).

O-[4-(β-D-glucopyranosyloxy)-3-methoxybenzyl]-8-methylnonanoic acid ester (4)

A mixture of β form O-[4-(2,3,4,6-tetra-O-acetyl-β-D-glucopyranosyloxy)-3-methoxybenzyl]-8-methylnonanoic acid ester (3) and α form (βform:α form ratio was about 7:1; 18.9 g, 29.6 mmol) was dissolved in methanol (250 ml) at room temperature, and the reaction mixture was cooled in an ice bath. Triethylamine (250 ml, 1.79 mol) was added, the ice bath was removed and the mixture was heated under reflux for 17 hours. The reaction mixture was cooled to room temperature, the solvent was concentrated under reduced pressure, and the residue was purified by silica gel column chromatography (gradient; methanol:ethyl acetate=2:98→11:89) to give a mixture of β form O-[4-(β-D-glucopyranosyloxy)-3-methoxybenzyl]-8-methylnonanoic acid ester (4) and α form (as a result of $^1$H-NMR analysis, β form:α form ratio was about 8:1; 7.24 g, 15.4 mmol, yield 52%) as a pale-yellow solid.

$^1$H-NMR (400 MHz, methanol-d$_4$) δ: 0.90 (d, 6H, J=6.7 Hz), 1.14-1.23 (m, 2H), 1.26-1.39 (m, 6H), 1.46-1.58 (m, 1H), 1.63 (tt, 2H, J=7.5 Hz, 7.5 Hz), 2.36 (t, 2H, J=7.5 Hz), 3.40-3.55 (m, 4H), 3.68-3.74 (m, 1H), 3.85-3.92 (m, 1H), 3.88 (s, 3H), 4.92 (d, 1H, J=7.5 Hz), 5.07 (s, 2H), 6.93 (dd, 1H, J=2.0 Hz, 8.3 Hz), 7.03 (d, 1H, J=2.0 Hz), 7.16 (d, 1H, J=8.3 Hz). ESIMS (m/z): 493.1 ([M+Na]$^+$), 509.0 ([M+K]$^+$).

This solid was subjected to a sensory evaluation of a pungent taste by the same method as in patent document 1 (JP-B-3506466) at concentration >10$^{-3}$ mol to find "−", namely, no pungent taste was found at all.

Example 2

4-acetoxymethyl-2-methoxyphenol (6)

Vanillyl alcohol (5) (10.3 g, 66.8 mmol) was dissolved in ethyl acetate (160 ml) at room temperature, Novozym 435 (2.00 g) was added, and the mixture was stirred at 65° C. for 69 hours. Then, the reaction mixture was cooled to room temperature, the enzyme was filtered off, and the filtrate was concentrated under reduced pressure. The residue was purified by silica gel column chromatography (gradient; ethyl acetate:n-hexane=19:81→40:60) to give 4-acetoxymethyl-2-methoxyphenol (6) (11.8 g, 59.8 mmol, yield 89%) as a colorless solid.

$^1$H-NMR (400 MHz, CDCl$_3$) δ: 2.10 (s, 3H), 3.91 (s, 3H), 5.04 (s, 2H), 5.79 (brs, 1H), 6.88-6.94 (m, 3H).

4-(2,3,4,6-tetra-O-acetyl-β-D-glucopyranosyloxy)-3-methoxybenzyl acetate (7)

Under an argon atmosphere, 2,3,4,6-tetra-O-acetyl-D-glucopyranose (2) (576 mg, 1.65 mmol) was dissolved in toluene (5 ml) at room temperature, and triphenylphosphine (423 mg, 1.61 mmol) and 4-acetoxymethyl-2-methoxyphenol (6) (204 mg, 1.04 mmol) were added. Then, the reaction mixture was cooled in an ice bath, diethyl azodicarboxylate 2.2 M toluene solution (0.75 ml, 1.65 mmol) was added dropwise, the ice bath was removed and the mixture was warmed to room temperature and stirred for 3 hours. The reaction solution was concentrated under reduced pressure, the insoluble material was filtered off, and the filtrate was concentrated under reduced pressure. The residue was purified by silica gel column chromatography (gradient; ethyl acetate:n-hexane=20:80→61:39) to give 4-(2,3,4,6-tetra-O-acetyl-β-D-glucopyranosyloxy)-3-methoxybenzyl acetate (7) (335 mg, 0.637 mmol, yield 61%) as a colorless oil.

$^1$H-NMR (400 MHz, CDCl$_3$) δ: 2.05 (s, 3H), 2.05 (s, 3H), 2.09 (s, 3H), 2.09 (s, 3H), 2.11 (s, 3H), 3.77 (ddd, 1H, J=2.5 Hz, 5.1 Hz, 9.9 Hz), 3.84 (s, 3H), 4.17 (dd, 1H, J=2.5 Hz, 12.2 Hz), 4.29 (dd, 1H, J=5.1 Hz, 12.2 Hz), 4.94-4.98 (m, 1H), 5.05 (s, 2H), 5.14-5.20 (m, 1H), 5.26-5.33 (m, 2H), 6.89 (dd, 1H, J=2.0 Hz, 8.0 Hz), 6.92 (d, 1H, J=2.0 Hz), 7.10 (d, 1H, J=8.0 Hz). ESIMS (m/z): 549.0 ([M+Na]$^+$), 565.0 ([M+K]$^+$).

4-(β-D-glucopyranosyloxy)-3-methoxybenzyl alcohol (8)

4-(2,3,4,6-tetra-O-acetyl-β-D-glucopyranosyloxy)-3-methoxybenzyl acetate (7) (333 mg, 0.632 mmol) was suspended in methanol (2 ml), and sodium methoxide 5 M methanol solution (20 μl, 0.10 mmol) was added while cooling in an ice bath. The ice bath was removed and the mixture was warmed to room temperature and stirred for 2 hours. Sodium methoxide 0.5 M methanol solution (0.12 ml, 0.06 mmol) was further added and the mixture was stirred for 1 hour. The reaction solution was neutralized with a strong acidic cation exchange resin (Amberlite IR120B H AG). The resin was filtered off, and the filtrate was concentrated under reduced pressure to give 4-(β-D-glucopyranosyloxy)-3-methoxybenzyl alcohol (8) (147 mg, 0.465 mmol, yield 74%) as a colorless solid.

$^1$H-NMR (400 MHz, methanol-d$_4$) δ: 3.40-3.55 (m, 4H), 3.67-3.75 (m, 1H), 3.85-3.92 (m, 1H), 3.89 (s, 3H), 4.56 (s, 2H), 4.89 (d, 1H, J=7.9 Hz), 6.90 (dd, 1H, J=1.9 Hz, 8.1 Hz), 7.04 (d, 1H, J=1.9 Hz), 7.15 (d, 1H, J=8.1 Hz). ESIMS (m/z): 339.2 ([M+Na]$^+$).

O-[4-(β-D-glucopyranosyloxy)-3-methoxybenzyl]-8-methylnonanoic acid ester (4)

4-(β-D-glucopyranosyloxy)-3-methoxybenzyl alcohol (8) (142 mg, 0.447 mmol) was dissolved in acetone (5 ml) at room temperature, 8-methylnonanoic acid (94.5 mg, 0.548 mmol), Novozym 435 (30.9 mg) and magnesium sulfate (143 mg) were added, and the mixture was heated to 50° C. and stirred for 26 hours. Since acetone evaporated during the reaction, supplemental acetone was added appropriately. Then, the reaction mixture was cooled to room temperature, the solid was filtered off, and the filtrate was concentrated under reduced pressure. The residue was purified by silica gel column chromatography (gradient; methanol:ethyl acetate:n-hexane=0:41:59→0:100:0→11:89:0) to give a mixture of β form O-[4-(β-D-glucopyranosyloxy)-3-methoxybenzyl]-8-methylnonanoic acid ester (4) and α form (as a result of $^1$H-NMR analysis, β form:α form ratio was about 7:1; 117 mg, 0.249 mmol, yield 56%) as a pale-yellow solid.

Example 3

D-cellobiose 2,2',3,3',4',6,6'-heptaacetate (10)

α-D-cellobiose octaacetate (9) (2.01 g, 2.96 mmol) was dissolved in N,N-dimethylformamide (8 ml) at room temperature, the reaction mixture was cooled in an ice bath, and ammonium acetate (473.5 mg, 6.14 mmol) was added. The ice bath was removed and the mixture was warmed to room temperature and stirred for 17 hours. The reaction mixture was heated to 60° C. and stirred for 3.5 hours. The reaction mixture was cooled in an ice bath, water (45 ml) was slowly added, the ice bath was removed and the mixture was extracted 4 times with ethyl acetate (40 ml) at room temperature. The combined organic layer was washed with water (40 ml), and then with 15% brine (40 ml). The organic layer was dried over magnesium sulfate, the solid was filtered off, and the filtrate was concentrated under reduced pressure. The residue was purified by silica gel column chromatography (gradient; ethyl acetate:n-hexane=62:38→83:17) to give D-cellobiose 2,2',3,3',4',6,6'-heptaacetate (10) (1.33 g, 2.09 mmol, yield 71%) as a colorless solid.

$^1$H-NMR (400 MHz, CDCl$_3$) δ: 1.98 (s, 3H), 2.01 (s, 3H), 2.03 (s, 3H), 2.03 (s, 3H), 2.07 (s, 3H), 2.08 (s, 3H), 2.13 (s, 3H), 3.67 (ddd, 1H, J=2.3, 4.3 Hz, 9.8 Hz), 3.72-3.81 (m, 1H), 3.80 (dd, 1H, J=9.4 Hz, 9.8 Hz), 4.04 (dd, 1H, J=2.3 Hz, 12.4 Hz), 4.11 (dd, 1H, J=4.3 Hz, 11.9 Hz), 4.17 (ddd, 1H, J=1.7 Hz, 4.3 Hz, 9.8 Hz), 4.37 (dd, 1H, J=4.3 Hz, 12.4 Hz), 4.48-4.57 (m, 2H), 4.82 (dd, 1H, J=3.7 Hz, 10.2 Hz), 4.89-4.96 (m, 1H), 5.04-5.25 (m, 2H), 5.36 (d, 1H, J=3.7 Hz) 5.50 (dd, 1H, J=9.4 Hz, 10.2 Hz). ESIMS (m/z): 659.0 ([M+Na]$^+$), 675.1 ([M+K]$^+$).

O-[4-(2,3,4,6-tetra-O-acetyl-β-D-glucopyranosyl-(1→4)-2,3,6-tri-O-acetyl-β-D-glucopyranosyloxy)-3-methoxybenzyl]-8-methylnonanoic acid ester (11)

Under an argon atmosphere, D-cellobiose 2,2',3,3',4',6,6'-heptaacetate (10) (1.47 g, 2.31 mmol) was dissolved in tetrahydrofuran (7.5 ml) and toluene (7.5 ml) at room temperature, and triphenylphosphine (978 mg, 3.73 mmol) and dihydrocapsiate (1.15 g, 3.73 mmol) were added. Then, the reaction mixture was cooled in an ice bath, diethyl azodicarboxylate 2.2 M toluene solution (1.7 ml, 3.74 mmol) was added dropwise, and the mixture was warmed to room temperature and stirred for 6 hours. The reaction solution was concentrated under reduced pressure, the insoluble material was filtered off, and the filtrate was concentrated under reduced pressure. The residue was purified by silica gel column chromatography (gradient; ethyl acetate:n-hexane=41:59→62:38) to give a mixture of β form O-[4-(2,3,4,6-tetra-O-acetyl-β-D-glucopyranosyl-(1→4)-2,3,6-tri-O-acetyl-β-D-glucopyranosyloxy)-3-methoxybenzyl]-8-methylnonanoic acid ester (11) and α form (as a result of $^1$H-NMR analysis, β form:α form ratio was about 5:1; 1.39 g, 1.50 mmol, yield 65%) as a colorless solid.

$^1$H-NMR (400 MHz, CDCl$_3$) δ: 0.86 (d, 6H, J=6.7 Hz), 1.11-1.19 (m, 2H), 1.22-1.37 (m, 6H), 1.44-1.59 (m, 1H), 1.60-1.69 (m, 2H), 1.99 (s, 3H), 2.02 (s, 3H), 2.04 (s, 3H), 2.06 (s, 3H), 2.07 (s, 3H), 2.10 (s, 3H), 2.12 (s, 3H), 2.35 (t, 2H, J=7.5 Hz), 3.63-3.72 (m, 2H), 3.77-3.91 (m, 1H), 3.82 (s, 3H), 4.07 (dd, 1H, J=2.4 Hz, 12.4 Hz), 4.11-4.35 (m, 2H), 4.38 (dd, 1H, J=4.4 Hz, 12.4 Hz), 4.46-4.58 (m, 1H), 4.54 (d, 1H, J=7.9 Hz), 4.91 (d, 1H, J=9.1 Hz), 4.94 (dd, 1H, J=7.9 Hz, 9.4 Hz), 5.05 (s, 2H), 5.05-5.29 (m, 3H), 6.87 (dd, 1H, J=2.0 Hz, 8.1 Hz), 6.89 (d, 1H, J=2.0 Hz), 7.06 (d, 1H, J=8.1 Hz). ESIMS (m/z): 949.5 ([M+Na]$^+$), 965.5 ([M+K]$^+$).

O-[4-(β-D-glucopyranosyl-(1→4)-β-D-glucopyranosyloxy)-3-methoxybenzyl]-8-methylnonanoic acid ester (12)

A mixture of β form O-[4-(2,3,4,6-tetra-O-acetyl-β-D-glucopyranosyl-(1→4)-2,3,6-tri-O-acetyl-β-D-glucopyranosyloxy)-3-methoxybenzyl]-8-methylnonanoic acid ester (11) and α form (β form:α form ratio was about 5:1; 225 mg, 0.243 mmol) was dissolved in methanol (2 ml) at room temperature, and the reaction mixture was cooled in an ice bath. Triethylamine (2 ml, 14.3 mmol) was added, the ice bath was removed and the mixture was heated under reflux for 18 hours. Then, to the reaction mixture were added methanol (2 ml) and triethylamine (2 ml, 14.3 mmol), and the mixture was further heated under reflux for 7 hours. The reaction mixture was cooled to room temperature, and concentrated under reduced pressure, and the residue was purified by ODS column chromatography (gradient; water:methanol=57:43→32:68). Since purification was insufficient, the obtained sample was further purified by silica gel column chromatography (gradient; methanol:ethyl acetate=12:88→21:79) to give a mixture of β form O-[4-(β-D-glucopyranosyl-(1→4)-β-D-glucopyranosyloxy)-3-methoxybenzyl]-8-methylnonanoic acid ester (12) and α form (as a result of $^1$H-NMR analysis, β form:α form ratio was about 4:1; 52.3 mg, 0.0827 mmol, yield 34%) as a colorless solid.

$^1$H-NMR (400 MHz, methanol-$d_4$) δ: 0.89 (d, 6H, J=6.7 Hz), 1.14-1.23 (m, 2H), 1.25-1.39 (m, 6H), 1.46-1.57 (m, 1H), 1.58-1.68 (m, 2H), 2.36 (t, 2H, J=7.5 Hz), 3.22-3.44 (m, 4H), 3.53-3.76 (m, 5H), 3.85-3.98 (m, 3H), 3.88 (s, 3H), 4.47 (d, 1H, J=7.9 Hz), 4.96 (d, 1H, J=7.3 Hz), 5.07 (s, 2H), 6.93 (dd, 1H, J=1.9 Hz, 8.3 Hz), 7.03 (d, 1H, J=1.9 Hz), 7.14 (d, 1H, J=8.3 Hz). ESIMS (m/z): 655.2 ([M+Na]$^+$), 670.9 ([M+K]$^+$).

Example 4

4-(2,3,4,6-tetra-O-acetyl-β-D-glucopyranosyl-(1→4)-2,3,6-tri-O-acetyl-β-D-glucopyranosyloxy)-3-methoxybenzyl acetate (13)

Under an argon atmosphere, D-cellobiose 2,2',3,3',4',6,6'-heptaacetate (10) (500 mg, 0.785 mmol) was dissolved in tetrahydrofuran (1.5 ml) and toluene (1.5 ml) at room temperature, and triphenylphosphine (333 mg, 1.27 mmol) and 4-acetoxymethyl-2-methoxyphenol (6) (244 mg, 1.24 mmol) were added. The reaction mixture was cooled in an ice bath, diethyl azodicarboxylate 2.2 M toluene solution (0.58 ml, 1.28 mmol) was added dropwise, the ice bath was removed and the mixture was warmed to room temperature and stirred for 4 hours. The reaction solution was concentrated under reduced pressure, the insoluble material was filtered off, and the filtrate was concentrated under reduced pressure. The residue was purified by silica gel column chromatography (gradient; ethyl acetate:n-hexane=53:47→74:26) to give 4-(2,3,4,6-tetra-O-acetyl-β-D-glucopyranosyl-(1→4)-2,3,6-tri-O-acetyl-β-D-glucopyranosyloxy)-3-methoxybenzyl acetate (13) (360 mg, 0.442 mmol, yield 56%) as a colorless oil.

$^1$H-NMR (400 MHz, CDCl$_3$) δ: 1.99 (s, 3H), 2.02 (s, 3H), 2.04 (s, 3H), 2.05 (s, 3H), 2.07 (s, 3H), 2.10 (s, 3H), 2.10 (s, 3H), 2.11 (s, 3H), 3.64-3.72 (m, 2H), 3.81-3.92 (m, 1H), 3.82 (s, 3H), 4.07 (dd, 1H, J=2.2 Hz, 12.4 Hz), 4.14 (dd, 1H, J=5.4 Hz, 11.9 Hz), 4.39 (dd, 1H, J=4.5 Hz, 12.4 Hz), 4.53 (dd, 1H, J=2.1 Hz, 11.9 Hz), 4.54 (d, 1H, J=8.0 Hz), 4.91 (d, 1H, J=7.6 Hz), 4.94 (dd, 1H, J=8.0 Hz, 9.2 Hz), 5.02-5.09 (m, 4H), 5.04 (s, 2H), 6.87 (dd, 1H, J=1.9 Hz, 8.1 Hz), 6.90 (d, 1H, J=1.9 Hz), 7.06 (d, 1H, J=8.1 Hz). ESIMS (m/z): 837.2 ([M+Na]$^+$), 853.2 ([M+K]$^+$).

4-(2,3,4,6-tetra-O-acetyl-β-D-glucopyranosyl-(1→4)-2,3,6-tri-O-acetyl-β-D-glucopyranosyloxy)-3-methoxybenzyl alcohol (14)

4-(2,3,4,6-Tetra-O-acetyl-β-D-glucopyranosyl-(1→4)-2,3,6-tri-O-acetyl-β-D-glucopyranosyloxy)-3-methoxybenzyl acetate (13) (355 mg, 0.436 mmol) was dissolved in methanol (1 ml) at room temperature, and the reaction mixture was cooled in an ice bath. Sodium methoxide 0.5 M methanol solution (260 μl, 0.13 mmol) was added, the ice bath was removed and the mixture was warmed to room temperature and stirred for 1.5 hours. The reaction solution was neutralized with a strong acidic cation exchange resin (Amberlite IR120B H AG), the resin was filtered off, and the filtrate was concentrated under reduced pressure to give a mixture of β form 4-(2,3,4,6-tetra-O-acetyl-β-D-glucopyranosyl-(1→4)-2,3,6-tri-O-acetyl-β-D-glucopyranosyloxy)-3-methoxybenzyl alcohol (14) and α form (as a result of $^1$H-NMR analysis, β form:α form ratio was about 7:1; 207 mg, 0.435 mmol, yield >99%) as a colorless solid.

$^1$H-NMR (400 MHz, methanol-$d_4$) δ: 3.23-3.45 (m, 5H), 3.52-3.75 (m, 5H), 3.85-3.95 (m, 2H), 3.88 (s, 3H), 4.46 (d, 1H, J=7.9 Hz), 4.56 (s, 2H), 4.94 (d, 1H, J=7.5 Hz), 6.90 (dd, 1H, J=1.8 Hz, 8.3 Hz), 7.04 (d, 1H, J=1.8 Hz), 7.13 (d, 1H, J=8.3 Hz). ESIMS (m/z): 501.1 ([M+Na]$^+$), 542.9 ([M+K]$^+$).

O-[4-(β-D-glucopyranosyl-(1→4)-β-D-glucopyranosyloxy)-3-methoxybenzyl]-8-methylnonanoic acid ester (12)

A mixture of β form 4-(2,3,4,6-tetra-O-acetyl-β-D-glucopyranosyl-(1→4)-2,3,6-tri-O-acetyl-β-D-glucopyranosyloxy)-3-methoxybenzyl alcohol (14) and α form (β form:α form ratio was about 7:1; 216 mg, 0.452 mmol) and 8-methylnonanoic acid methyl ester (866 mg, 4.65 mmol) were mixed at room temperature, and Novozym 435 (46.8 mg) was added. The reaction mixture was stirred at 50° C. for 40 hours, and the mixture was heated and further stirred for 8 hr with heating under reflux. Then, acetone (5 ml) was added, and the mixture was further heated under reflux for 16 hours. Then, the reaction mixture was cooled to room temperature, methanol (20 ml) was added, the enzyme was filtered off, and the filtrate was concentrated under reduced pressure. The residue was purified by ODS column chromatography (gradient; water:methanol=58:42→33:67) to give a mixture of β form O-[4-(β-D-glucopyranosyl-(1→4)-β-D-glucopyranosyloxy)-3-methoxybenzyl]-8-methylnonanoic acid ester (12) and α form (as a result of $^1$H-NMR analysis, β form:α form ratio was about 9:1; 75.1 mg, 0.119 mmol, yield 26%) as a colorless solid.

Example 5

O-[4-(2,3,4,6-tetra-O-acetyl-β-D-glucopyranosyloxy)-3-methoxybenzyl]-decanoic acid ester (15)

Under an argon atmosphere, 2,3,4,6-tetra-O-acetyl-D-glucopyranose (2) (5.72 g, 16.4 mmol) was dissolved in toluene (35 ml), and triphenylphosphine (4.28 g, 16.3 mmol) and vanillyl decanoate (3.16 g, 10.2 mmol) were added at room temperature. Then, the reaction mixture was cooled in an ice bath, and diethyl azodicarboxylate 2.2 M toluene solution (7.5 ml, 16.5 mmol) was added dropwise. After stirring for 5 minutes, the ice bath was removed and the mixture was warmed to room temperature and stirred for 22 hours. The reaction solution was concentrated under reduced pressure, the insoluble material was filtered off, and the filtrate was concentrated under reduced pressure. The residue was purified by silica gel column chromatography (gradient; ethyl acetate:n-hexane=15:85→46:54) to give a mixture of β form O-[4-(2,3,4,6-tetra-O-acetyl-β-D-glucopyranosyloxy)-3-methoxybenzyl]-decanoic acid ester (15) and α form (as a result of $^1$H-NMR analysis, β form:α form ratio was about 7:1; 4.71 g, 7.37 mmol, yield 72%) as a pale-yellow oil.

¹H-NMR (400 MHz, CDCl₃) δ: 0.88 (t, 3H, J=6.9 Hz), 1.20-1.34 (m, 12H), 1.59-1.65 (m, 2H), 2.04 (s, 3H), 2.04 (s, 3H), 2.08 (s, 3H), 2.08 (s, 3H), 2.34 (t, 2H, J=7.5 Hz), 3.76 (ddd, 1H, J=2.4 Hz, 5.0 Hz, 10.0 Hz), 3.82 (s, 3H), 4.16 (dd, 1H, J=2.4 Hz, 12.2 Hz), 4.28 (dd, 1H, J=5.0 Hz, 12.2 Hz), 4.93-4.98 (m, 1H), 5.05 (s, 2H), 5.13-5.19 (m, 1H), 5.25-5.31 (m, 2H), 6.86 (dd, 1H, J=1.9 Hz, 8.1 Hz), 6.89 (d, 1H, J=1.9 Hz), 7.09 (d, 1H, J=8.1 Hz). ESIMS (m/z): 661.0 ([M+Na]⁺), 677.3 ([M+K]⁺).

O-[4-(β-D-glucopyranosyloxy)-3-methoxybenzyl]-decanoic acid ester (16)

A mixture of β form O-[4-(2,3,4,6-tetra-O-acetyl-β-D-glucopyranosyloxy)-3-methoxybenzyl]-decanoic acid ester (15) and α form (β form:α form ratio was about 7:1; 3.90 g, 6.11 mmol) was dissolved in methanol (51 ml) at room temperature, and the mixture was cooled in an ice bath. Triethylamine (51.2 ml, 367 mmol) was added, the ice bath was removed and the mixture was heated under reflux for 22 hours. The reaction mixture was cooled to room temperature, the solvent was concentrated under reduced pressure, and the residue was purified by silica gel column chromatography (gradient; methanol:ethyl acetate=2:98→11:89) to give a mixture of β form O-[4-(β-D-glucopyranosyloxy)-3-methoxybenzyl]-decanoic acid ester (16) and α form (as a result of ¹H-NMR analysis, β form:α form ratio was about 9:1; 2.01 g, 4.27 mmol, yield 70%) as a pale-yellow solid.

¹H-NMR (400 MHz, methanol-d₄) δ: 0.90 (t, 3H, J=6.6 Hz), 1.24-1.36 (m, 12H), 1.61 (tt, 2H, J=7.3 Hz, 7.3 Hz), 2.34 (t, 2H, J=7.3 Hz), 3.35-3.56 (m, 4H), 3.65-3.73 (m, 1H), 3.86 (s, 3H), 3.86-3.89 (m, 1H), 4.90 (d, 1H, J=7.3 Hz), 5.05 (s, 2H), 6.91 (dd, 1H, J=1.9 Hz, 8.3 Hz), 7.00 (d, 1H, J=1.9 Hz), 7.15 (d, 1H, J=8.3 Hz). ESIMS (m/z): 493.2 ([M+Na]⁺), 509.2 ([M+K]⁺).

Example 6

O-[4-(2,3,4,6-tetra-O-acetyl-β-D-glucopyranosyloxy)-3-methoxybenzyl]-7-methyloctanoic acid ester (17)

Under an argon atmosphere, 2,3,4,6-tetra-O-acetyl-D-glucopyranose (2) (5.62 g, 16.1 mmol) was dissolved in toluene (35 ml), and triphenylphosphine (4.28 g, 16.3 mmol) and nordihydrocapsiate (2.98 g, 10.1 mmol) were added at room temperature. Then, the reaction mixture was cooled in an ice bath, and diethyl azodicarboxylate 2.2 M toluene solution (7.5 ml, 16.5 mmol) was added dropwise. After stirring for 5 minutes, the ice bath was removed and the mixture was warmed to room temperature and stirred for 18 hours. The reaction solution was concentrated under reduced pressure, the insoluble material was filtered off, and the filtrate was concentrated under reduced pressure. The residue was purified by silica gel column chromatography (gradient; ethyl acetate:n-hexane=24:76→45:55) to give a mixture of β form O-[4-(2,3,4,6-tetra-O-acetyl-β-D-glucopyranosyloxy)-3-methoxybenzyl]-7-methyloctanoic acid ester (17) and α form (as a result of ¹H-NMR analysis, β form:α form ratio was about 7:1; 4.16 g, 6.66 mmol, yield 66%) as a pale-yellow oil.

¹H-NMR (400 MHz, CDCl₃) δ: 0.85 (d, 6H, J=6.7 Hz), 1.11-1.19 (m, 2H), 1.23-1.36 (m, 4H), 1.45-1.56 (m, 1H), 1.60-1.68 (m, 2H), 2.04 (s, 3H), 2.04 (s, 3H), 2.08 (s, 3H), 2.08 (s, 3H), 2.34 (t, 2H, J=7.5 Hz), 3.76 (ddd, 1H, J=2.5 Hz, 5.0 Hz, 10.0 Hz), 3.82 (s, 3H), 4.16 (dd, 1H, J=2.5 Hz, 12.2 Hz), 4.28 (dd, 1H, J=5.0 Hz, 12.2 Hz), 4.93-4.97 (m, 1H), 5.05 (s, 2H), 5.10-5.21 (m, 1H), 5.23-5.32 (m, 2H), 6.86 (dd, 1H, J=1.9 Hz, 8.0 Hz), 6.90 (d, 1H, J=1.9 Hz), 7.09 (d, 1H, J=8.0 Hz). ESIMS (m/z): 647.2 ([M+Na]⁺), 663.3 ([M+K]⁺).

O-[4-(β-D-glucopyranosyloxy)-3-methoxybenzyl]-7-methyloctanoic acid ester (18)

A mixture of β form O-[4-(2,3,4,6-tetra-O-acetyl-β-D-glucopyranosyloxy)-3-methoxybenzyl]-7-methyloctanoic acid ester (17) and α form (β form:α form ratio was about 7:1; 3.36 g, 5.38 mmol) was dissolved in methanol (46 ml) at room temperature, and the reaction mixture was cooled in an ice bath. Triethylamine (46.0 ml, 330 mmol) was added, the ice bath was removed and the mixture was heated under reflux for 23 hours. The reaction mixture was cooled to room temperature, the solvent was concentrated under reduced pressure, and the residue was purified by silica gel column chromatography (gradient; methanol:ethyl acetate=2:98→11:89) to give a mixture of β form O-[4-(β-D-glucopyranosyloxy)-3-methoxybenzyl]-7-methyloctanoic acid ester (18) and α form (as a result of ¹H-NMR analysis, β form:α form ratio was about 9:1; 1.71 g, 3.75 mmol, yield 70%) as a pale-yellow solid.

¹H-NMR (400 MHz, methanol-d₄) δ: 0.89 (d, 6H, J=6.7 Hz), 1.14-1.23 (m, 2H), 1.25-1.37 (m, 4H), 1.46-1.58 (m, 1H), 1.58-1.68 (m, 2H), 2.36 (t, 2H, J=7.4 Hz), 3.40-3.58 (m, 4H), 3.68-3.76 (m, 1H), 3.86-3.90 (m, 1H), 3.87 (s, 3H), 4.92 (d, 1H, J=7.3 Hz), 5.07 (s, 2H), 6.93 (dd, 1H, J=1.9 Hz, 8.3 Hz), 7.03 (d, 1H, J=1.9 Hz), 7.16 (d, 1H, J=8.3 Hz). ESIMS (m/z): 479.0 ([M+Na]⁺), 495.2 ([M+K]⁺).

Example 7

O-[4-(2,3,4,6-tetra-O-acetyl-β-D-glucopyranosyloxy)-3-methoxybenzyl]-8-methyl-6-nonenoic acid ester (19)

Under an argon atmosphere, 2,3,4,6-tetra-O-acetyl-D-glucopyranose (2) (6.03 g, 17.3 mmol) was dissolved in toluene (35 ml), and triphenylphosphine (4.54 g, 17.3 mmol) and capsiate (3.27 g, 10.7 mmol) were added at room temperature. Then, the reaction mixture was cooled in an ice bath, and diethyl azodicarboxylate 2.2 M toluene solution (7.8 ml, 17.2 mmol) was added dropwise. After stirring for 5 minutes, the ice bath was removed and the mixture was warmed to room temperature and stirred for 17 hours. The reaction solution was concentrated under reduced pressure, the insoluble material was filtered off, and the filtrate was concentrated under reduced pressure. The residue was purified by silica gel column chromatography (gradient; ethyl acetate:n-hexane=25:75→46:54) to give a mixture of β form O-[4-(2,3,4,6-tetra-O-acetyl-β-D-glucopyranosyloxy)-3-methoxybenzyl]-8-methyl-6-nonenoic acid ester (19) and α form (as a result of ¹H-NMR analysis, β form:α form ratio was about 6:1; 4.58 g, 7.19 mmol, yield 67%) as a pale-yellow oil.

¹H-NMR (400 MHz, CDCl₃) δ: 0.95 (d, 6H, J=6.7 Hz), 1.33-1.43 (m, 2H), 1.60-1.68 (m, 2H), 1.94-2.02 (m, 2H), 2.04 (s, 3H), 2.04 (s, 3H), 2.08 (s, 3H), 2.08 (s, 3H), 2.16-2.27 (m, 1H), 2.35 (t, 2H, J=7.5 Hz), 3.76 (ddd, 1H, J=2.4 Hz, 5.0 Hz, 9.9 Hz), 3.82 (s, 3H), 4.16 (dd, 1H, J=2.4 Hz, 12.2 Hz), 4.28 (dd, 1H, J=5.0 Hz, 12.2 Hz), 4.94-4.97 (m, 1H), 5.05 (s, 2H), 5.16 (dd, 1H, J=9.9, 9.9 Hz), 5.25-5.41 (m, 4H), 6.87 (dd, 1H, J=1.8 Hz, 8.1 Hz), 6.89 (d, 1H, J=1.8 Hz), 7.09 (d, 1H, J=8.1 Hz). ESIMS (m/z): 659.3 ([M+Na]⁺), 675.3 ([M+K]⁺).

O-[4-(β-D-glucopyranosyloxy)-3-methoxybenzyl]-8-methyl-6-nonenoic acid ester (20)

A mixture of β form O-[4-(2,3,4,6-tetra-O-acetyl-β-D-glucopyranosyloxy)-3-methoxybenzyl]-8-methyl-6-nonenoic acid ester (19) and α form (β form:α form ratio was about 6:1; 4.00 g, 6.28 mmol) was dissolved in methanol (53 ml) at room temperature, and the mixture was cooled in an ice bath. Triethylamine (53.0 ml, 380 mmol) was added, the ice bath was removed, and the mixture was heated to 70° C. and stirred for 23 hours. The reaction mixture was cooled to room temperature, the solvent was concentrated under reduced pressure, and the residue was purified by silica gel column chromatography (gradient; methanol:ethyl acetate=2:98→11:89) to give a mixture of β form O-[4-(β-D-glucopyranosyloxy)-3-methoxybenzyl]-8-methyl-6-nonenoic acid ester (20) and α form (as a result of $^1$H-NMR analysis, β form:α form ratio was about 6:1; 2.08 g, 4.44 mmol, yield 71%) as a pale-yellow solid.

$^1$H-NMR (400 MHz, methanol-$d_4$) δ: 0.97 (d, 6H, J=6.8 Hz), 1.33-1.43 (m, 2H), 1.58-1.68 (m, 2H), 1.96-2.04 (m, 2H), 2.17-2.31 (m, 1H), 2.37 (t, 2H, J=7.3 Hz), 3.40-3.59 (m, 4H), 3.67-3.76 (m, 1H), 3.86-3.93 (m, 1H), 3.88 (s, 3H), 4.92 (d, 1H, J=7.5 Hz), 5.07 (s, 2H), 5.30-5.48 (m, 2H), 6.93 (dd, 1H, J=2.1 Hz, 8.3 Hz), 7.03 (d, 1H, J=2.1 Hz), 7.16 (d, 1H, J=8.3 Hz). ESIMS (m/z): 491.1 ([M+Na]$^+$), 507.1 ([M+K]$^+$).

Example 8

O-8-methylnonyl-2-[4-(β-D-glucopyranosyl-(1→4)-β-D-glucopyranosyloxy)-3-methoxyphenyl]acetic acid ester (22)

Under an argon atmosphere, compound 21 (740 mg, 5.84 mmol) was dissolved in a mixed solvent of toluene (5 ml) and tetrahydrofuran (THF, 5 ml), and triphenylphosphine (PPh$_3$, 1.54 g, 5.86 mmol) and D-cellobiose 2,2',3,3',4',6,6'-heptaacetate (10) (2.32 g, 3.65 mmol) were added at room temperature. Then, the reaction mixture was cooled in an ice bath, and diethyl azodicarboxylate 2.2 M toluene solution (DEAD, 2.65 ml, 5.84 mmol) was added dropwise. After stirring for 10 minutes, the ice bath was removed and the mixture was warmed to room temperature, and further stirred for 22 hours. The reaction solution was concentrated under reduced pressure, the insoluble material was filtered off, and the filtrate was concentrated under reduced pressure. The residue was purified by silica gel column chromatography (gradient; ethyl acetate:n-hexane=1:9→1:1) to give a mixture of β form and α form of compound 22-1 (as a result of $^1$H-NMR analysis, β form:α form ratio was about 4:1; 2.49 g, 2.64 mmol, yield 72%) as a colorless solid.

$^1$H-NMR (400 MHz, CDCl$_3$) δ: 0.85 (d, 6H, J=6.6 Hz), 1.10-1.52 (m, 2H), 1.29-1.32 (m, 8H), 1.46-1.56 (m, 3H), 1.98 (s, 3H), 2.01 (s, 3H), 2.03 (s, 3H), 2.04 (s, 3H), 2.06 (s, 3H), 2.09 (s, 3H), 2.10 (s, 3H), 3.55-3.58 (m, 2H), 3.63-3.69 (m, 2H), 3.79 (s, 3H), 3.79-3.88 (m, 1H), 4.04-4.15 (m, 5H), 4.35-4.40 (m, 1H), 4.50-4.55 (m, 2H), 4.87-4.98 (m, 2H), 5.04-5.27 (m, 3H), 6.75 (dd, 1H, J=2.0 Hz, 9.2 Hz), 6.83 (d, 1H, J=2.0 Hz), 7.01 (d, 1H, J=9.2 Hz). ESIMS (m/z): 963.4 ([M+Na]$^+$), 979.4 ([M+K]$^+$).

Then, a mixture of β form and α form of compound 22-1 (β form:α form ratio was about 4:1; 2.27 g, 2.41 mmol) was dissolved in methanol (MeOH, 40 ml) at room temperature, and the mixture was cooled in an ice bath. Triethylamine (Et$_3$N, 40 ml, 289 mmol) was added, and the mixture was stirred for 10 min. The ice bath was removed and the mixture was heated under reflux for 45 hours. The reaction mixture was cooled to room temperature, and concentrated under reduced pressure, and the residue was purified by ODS column chromatography (gradient; water:methanol=97:3→17:3). Since the purification was insufficient, 80.2 mg of the obtained sample (183 mg) was further purified by preparative thin layer chromatography (PTLC) (methanol:dichloromethane=1:9) to give a mixture of β form and α form of O-8-methylnonyl-2-[4-(β-D-glucopyranosyl-(1→4)-β-D-glucopyranosyloxy)-3-methoxyphenyl]acetic acid ester (22) (as a result of $^1$H-NMR analysis, β form:α form ratio was about 4:1; 21.4 mg, 0.033 mmol, theoretical yield 32%) as a colorless solid.

$^1$H-NMR (400 MHz, methanol-$d_4$) δ: 0.88 (d, 6H, J=6.6 Hz), 1.18 (m, 2H), 1.30 (m, 8H), 1.48-1.63 (m, 3H), 3.22-3.40 (m, 3H), 3.51-3.73 (m, 7H), 3.84-4.03 (m, 4H), 3.85 (s, 3H), 4.08 (t, 2H, J=6.6 Hz), 4.44 (d, 1H, J=7.8 Hz), 4.91 (d, 1H, J=7.6 Hz), 6.81 (dd, 1H, J=1.7 Hz, 8.2 Hz), 6.95 (d, 1H, J=1.7 Hz), 7.10 (d, 1H, J=8.2 Hz). ESIMS (m/z): 669.3 ([M+Na]$^+$).

Example 9

O-[4-(β-D-glucopyranosyl-(1→4)-β-D-glucopyranosyloxy)-3-methoxyphenethyl]-8-methylnonanoic acid ester (23)

Under an argon atmosphere, compound 23-1 (755 mg, 2.34 mmol) was dissolved in a mixed solvent of toluene (2.5 ml) and THF (2.5 ml), and triphenylphosphine (966 mg, 3.68 mmol) and D-cellobiose 2,2',3,3',4',6,6'-heptaacetate (10) (2.30 g, 3.62 mmol) were added at room temperature. Then, the reaction mixture was cooled in an ice bath, and diethyl azodicarboxylate 2.2 M toluene solution (1.70 ml, 3.74 mmol) was added dropwise. After stirring for 10 minutes, the ice bath was removed and the mixture was warmed to room temperature, and further stirred for 14 hours. The reaction solution was concentrated under reduced pressure, the insoluble material was filtered off, and the filtrate was concentrated under reduced pressure. The residue was purified by silica gel column chromatography (gradient; ethyl acetate:n-hexane=1:9→1:1) to give a mixture of β form and α form of compound 23-2 (as a result of $^1$H-NMR analysis, β form:α form ratio was about 9:1; 1.01 g, 1.08 mmol, yield 46%) as a colorless solid.

$^1$H-NMR (400 MHz, CDCl$_3$) δ: 0.86 (d, 6H, J=6.6 Hz), 1.12-1.17 (m, 2H), 1.23-1.31 (m, 6H), 1.42-1.54 (m, 1H), 1.56-1.63 (m, 2H), 1.98 (s, 3H), 2.01 (s, 3H), 2.02 (s, 3H), 2.04 (s, 3H), 2.06 (s, 3H), 2.07 (s, 3H), 2.10 (s, 3H), 2.28 (t, 2H, J=7.7 Hz), 2.87 (t, 2H, J=7.1 Hz), 3.63-3.69 (m, 2H), 3.78 (s, 3H), 3.78-3.87 (m, 2H), 4.03-4.26 (m, 3H), 4.35-4.40 (m, 1H), 4.51-4.54 (m, 2H), 4.87-5.27 (m, 6H), 6.70 (dd, 1H, J=1.7 Hz, 8.1 Hz), 6.73 (d, 1H, J=1.7 Hz), 7.00 (d, 1H, J=8.1 Hz). ESIMS (m/z): 963.4 ([M+Na]$^+$), 979.4 ([M+K]$^+$).

Then, a mixture of β form and α form of compound 23-2 (β form:α form ratio was about 9:1; 804 mg, 0.854 mmol) was dissolved in methanol (14 ml) at room temperature, and the mixture was cooled in an ice bath. Triethylamine (14 ml, 102 mmol) was added and after stirring for 10 min, the ice bath was removed and the mixture was heated under reflux for 40 hours. The reaction mixture was cooled to room temperature, and concentrated under reduced pressure, and the residue was purified by preparative thin layer chromatography (PTLC) (methanol:dichloromethane=3:17) to give a mixture of β form and α form of O-[4-(β-D-glucopyranosyl-(1→4)-β-D-glucopyranosyloxy)-3-methoxyphenethyl]-8-methylnonanoic acid ester (23) (as a result of $^1$H-NMR analysis, β form:α form ratio was about 9:1; 88.6 mg, 0.137 mmol, theoretical yield 44%) as a pale-yellow solid.

$^1$H-NMR (400 MHz, methanol-$d_4$) δ: 0.88 (d, 6H, J=6.6 Hz), 1.15-1.20 (m, 2H), 1.24-1.31 (m, 6H), 1.48-1.59 (m, 3H), 2.29 (t, 2H, J=7.4 Hz), 2.88 (t, 2H, J=6.8 Hz), 3.24 (t, 1H, J=8.4 Hz), 3.28-3.40 (m, 3H), 3.50-3.70 (m, 5H), 3.85 (s, 3H), 3.85-3.91 (m, 3H), 4.26 (t, 2H, J=6.9 Hz), 4.44 (d, 1H, J=7.8

Hz), 4.90 (d, 1H, J=7.6 Hz), 6.78 (dd, 1H, J=1.9 Hz, 8.4 Hz), 6.90 (d, 1H, J=1.9 Hz), 7.08 (d, 1H, J=8.4 Hz). ESIMS (m/z): 669.3 ([M+Na]$^+$).

Example 10

O-[2-(β-D-glucopyranosyl-(1→4)-β-D-glucopyranosyloxy)-3-methoxybenzyl]-8-methylnonanoic acid ester (24)

Under an argon atmosphere, compound 24-1 (698 mg, 2.26 mmol) was dissolved in a mixed solvent of toluene (3.5 ml) and THF (3.5 ml), and triphenylphosphine (829 mg, 3.16 mmol) and D-cellobiose 2,2',3,3',4',6,6'-heptaacetate (10) (2.31 g, 3.62 mmol) were added at room temperature. Then, the reaction mixture was cooled in an ice bath, and diethyl azodicarboxylate 2.2 M toluene solution (1.43 ml, 3.15 mmol) was added dropwise. After stirring for 10 minutes, the ice bath was removed and the mixture was warmed to room temperature, and further stirred for 14 hours. The reaction solution was concentrated under reduced pressure, the insoluble material was filtered off, and the filtrate was concentrated under reduced pressure. The residue was purified by silica gel column chromatography (gradient; ethyl acetate:n-hexane=1:9→1:1) to give a mixture of β form and α form of compound 24-2 (as a result of $^1$H-NMR analysis, β form:α form ratio was about 3:2; 607 mg, 0.655 mmol, yield 29%) as a colorless solid.

$^1$H-NMR (400 MHz, CDCl$_3$) δ: 0.86 (d, 6H, J=6.6 Hz), 1.11-1.17 (m, 2H), 1.25-1.33 (m, 6H), 1.47-1.54 (m, 1H) 1.60-1.68 (m, 2H,) 1.97 (s, 3H), 1.98 (s, 3H), 2.01 (s, 3H), 2.05 (s, 3H), 2.08 (s, 3H), 2.09 (s, 3H), 2.10 (s, 3H), 2.35 (t, 2H, J=7.8 Hz), 3.44-3.48 (m, 1H), 3.65-3.69 (m, 1H), 3.82 (s, 3H), 3.82-3.89 (m, 1H), 4.00-4.08 (m, 2H), 4.36-4.40 (m, 1H), 4.46-4.53 (m, 2H), 4.90-4.94 (m, 1H), 5.02-5.08 (m, 3H), 5.12-5.18 (m, 2H), 5.23-5.29 (m, 2H), 6.85-6.87 (m, 1H), 6.92-6.94 (m, 1H), 7.09 (d, 1H, J=8.0 Hz). ESIMS (m/z): 949.4 ([M+Na]$^+$), 965.3 ([M+K]$^+$).

Then, a mixture of β form and α form of compound 24-2 (β form:α form ratio was about 3:2; 565 mg, 0.609 mmol) was dissolved in methanol (10 ml) at room temperature, and the mixture was cooled in an ice bath. Triethylamine (10 ml, 73.2 mmol) was added and after stirring for 10 minutes, the ice bath was removed and the mixture was heated under reflux for 42 hours. The reaction mixture was cooled to room temperature, and concentrated under reduced pressure, and the residue was purified by silica gel column chromatography (gradient; ethyl acetate:methanol=97:3→23:2) to give a mixture of β form and α form of O-[2-(β-D-glucopyranosyl-(1→4)-β-D-glucopyranosyloxy)-3-methoxybenzyl]-8-methylnonanoic acid ester (24) (as a result of $^1$H-NMR analysis, β form:α form ratio was about 3:2; 104 mg, 0.16 mmol, yield 26%) as a pale-yellow solid.

$^1$H-NMR (400 MHz, methanol-d$_4$) δ: 0.88 (d, 6H, J=6.6 Hz), 1.14-1.20 (m, 2H), 1.26-1.38 (m, 6H), 1.47-1.57 (m, 1H), 1.60-1.67 (m, 2H), 2.38 (t, 2H, J=7.4 Hz), 3.22 (t, 1H, J=8.4 Hz), 3.28-3.39 (m, 4H), 3.51-3.69 (m, 4H), 3.76-3.91 (m, 6H), 4.43 (d, 1H, J=7.9 Hz), 4.92 (d, 1H, J=5.8 Hz), 5.30 (d, 1H, J=13.2 Hz), 5.36 (d, 1H, J=13.1 Hz), 6.92 (dd, 1H, J=1.5 Hz, 7.8 Hz), 7.01 (dd, 1H, J=1.5 Hz, 7.8 Hz), 7.10 (d, 1H, J=7.8 Hz). ESIMS (m/z): 655.3 ([M+Na]$^+$).

Example 11

O-[4-(β-D-maltotriosyloxy)-3-methoxybenzyl]-8-methylnonanoic acid ester (25)

D-maltotriose (25-1) (5.0 g, 9.91 mmol) was dissolved in pyridine (30 ml) at room temperature, and the mixture was cooled in an ice bath. Acetic anhydride (Ac$_2$O, 15 ml, 149 mmol) was slowly added using a dropping funnel and the mixture was stirred for 10 minutes. The ice bath was removed and the mixture was warmed to room temperature and stirred for 20 hours. The reaction container was cooled in an ice bath, water (50 ml) was added slowly, and the mixture was extracted 5 times with ethyl acetate (50 ml) at room temperature. To the combined is organic layer was washed twice with 3 N HCl (50 ml), then successively washed once with each of water (50 ml), aqueous sodium hydrogen carbonate solution (50 ml), and 15% brine (30 ml) in this order. The organic layer was dried over anhydrous magnesium sulfate, and filtered, and the filtrate was concentrated under reduced pressure. Three spots were confirmed by thin layer chromatography (TLC) and, since MS analysis values with one missing acetyl group (Ac group) were obtained, acetylation was performed again. The obtained crude product was dissolved in pyridine (25 ml) at room temperature, and the mixture was cooled in an ice bath. N,N-dimethyl-4-aminopyridine (DMAP, 229 mg, 1.88 mmol) and acetic anhydride (5 ml, 49.5 mmol) were slowly added using a dropping funnel. The ice bath was removed and the mixture was warmed to room temperature and heated under reflux for 12 hours. The reaction container was cooled in an ice bath, water (50 ml) was added slowly, and the mixture was extracted 5 times with ethyl acetate (50 ml) at room temperature. The combined organic layer was washed twice with 3 N HCl (50 ml), then twice with water (50 ml), and once each with aqueous sodium hydrogen carbonate solution (50 ml) and 15% brine (30 ml). The organic layer was dried over anhydrous magnesium sulfate and filtered, and the filtrate was concentrated under reduced pressure to give a mixture of β form and α form of compound 25-2 (the ratio of β form:α form was difficult to determine from the results of $^1$H-NMR analysis; 8.71 g, 9.01 mol, yield 91%) as a colorless solid. This compound 25-2 (4.0 g, 4.32 mmol) was dissolved in N,N-dimethylformamide (8 ml) at room temperature, and the mixture was cooled in an ice bath. To this solution was added ammonium acetate (793 mg, 10.8 mmol), the ice bath was removed and the mixture was warmed to room temperature and stirred for 21 hours. The reaction container was cooled in an ice bath, water (50 ml) was added slowly, the ice bath was removed, and the mixture was extracted 5 times with ethyl acetate (50 ml) at room temperature. The combined organic layer was washed with 15% brine (50 ml), and the organic layer was dried over anhydrous magnesium sulfate and filtered, and the filtrate was concentrated under reduced pressure. The residue was purified by silica gel column chromatography (gradient; ethyl acetate:n-hexane=3:7→3:2) to give a mixture of β form and α form of compound 25-3 (the ratio of β form:α form was difficult to determine from the results of $^1$H-NMR analysis; 3.44 g, 3.72 mmol, yield 86%) as a colorless solid.

$^1$H-NMR (400 MHz, methanol-d$_4$) δ: 1.99-2.06 (m, 24H), 2.13 (s, 3H), 2.14 (s, 3H), 3.93-3.99 (m, 2H), 4.04-4.14 (m, 3H), 4.19-4.27 (m, 3H), 4.29-4.34 (m, 1H), 4.41-4.50 (m, 2H), 4.67-4.79 (m, 2H), 5.05 (t, 1H, J=9.7 Hz), 5.24-5.45 (m, 6H), 5.55 (t, 1H, J=9.7 Hz). ESIMS (m/z): 941.9 ([M+NH$_4$]$^+$), 946.9 ([M+K]$^+$), 963.0 ([M+K]$^+$).

Then, under an argon atmosphere, compound 6 (579 mg, 2.95 mmol) was dissolved in a mixed solvent of toluene (5 ml) and THF (5 ml), and triphenylphosphine (774 mg, 2.95 mmol) and compound 25-3 (2.01 g, 2.29 mmol) were added at room temperature. The reaction mixture was cooled in an ice bath, and diethyl azodicarboxylate 2.2 M toluene solution (1.34 ml, 2.95 mmol) was added dropwise. After stirring for 10 minutes, the ice bath was removed, and the mixture was warmed to room temperature, and further stirred for 13 hours.

The reaction solution was concentrated under reduced pressure, the insoluble material was filtered off, and the filtrate was concentrated under reduced pressure. The residue was purified by silica gel column chromatography (gradient; ethyl acetate:n-hexane=1:5→11:9) to give a mixture of β form and α form of compound 25-4 as a colorless solid as a mixture with triphenylphosphine oxide (O=PPh$_3$) (the ratio of β form:α form was difficult to determine from the results of $^1$H-NMR analysis; 1.02 g, 0.925 mmol, yield 31%). Then, compound 25-4 (1.02 g, 0.925 mmol) was dissolved in methanol (7 ml), and sodium methoxide 5 M methanol solution (NaOMe, 100 μl, 500 mmol) was added in an ice bath. The ice bath was removed and the mixture was warmed to room temperature and stirred for 1.5 hours. The reaction solution was neutralized with a strong acidic cation exchange resin (Amberlite IR120B H AG). The resin was filtered off, and the filtrate was concentrated under reduced pressure to give a mixture of β form and α form of compound 25-5 (the ratio of β form:α form was difficult to determine from the results of $^1$H-NMR analysis; 367 mg, 0.572 mmol, yield 49%) as a colorless solid as a mixture with O=PPh$_3$. The compound 25-5 (250 mg, 0.390 mmol) was dissolved in acetone (8 ml) at room temperature, 8-methylnonanoic acid (8-MNA, 672 mg, 3.90 mmol) was added, and the reaction mixture was cooled in an ice bath. Novozym 435 (53.6 mg) and molecular sieves 3A (253 mg) were added. After stirring for 10 minutes, the ice bath was removed and the mixture was heated under reflux for 17 hours. Since acetone evaporated during the reaction, supplemental acetone was added appropriately. Then, the reaction mixture was cooled to room temperature, and the solid was filtered off. Since precipitation occurred in the filtrate, the solid was collected by filtration, dissolved in methanol, and the mixture was concentrated under reduced pressure. The obtained residue was purified by ODS column chromatography (gradient; water:methanol=17:3→3:2→0:100). Since purification was insufficient, the obtained sample was slurried with diethyl ether, filtered and concentrated to give a mixture of β form and α form of O-[4-(β-D-maltotriosyloxy)-3-methoxybenzyl]-8-methylnonanoic acid ester (25) (as a result of $^1$H-NMR analysis, β form:α form ratio was about 4:1; 31.4 mg, 0.0114 mmol, yield 6%) as a colorless solid.

$^1$H-NMR (400 MHz, methanol-d$_4$) δ: 0.88 (d, 6H, J=6.6 Hz), 1.16-1.20 (m, 2H), 1.29 (m, 6H), 1.49-1.63 (m, 3H), 2.35 (t, 2H, J=7.4 Hz), 3.42-3.89 (m, 18H), 3.86 (s, 3H), 4.93 (d, 1H, J=7.8 Hz), 5.06 (s, 2H), 5.15 (d, 1H, J=3.8 Hz), 5.21 (d, 1H, J=3.8 Hz), 6.92 (dd, 1H, J=1.9 Hz, 8.3 Hz), 7.02 (d, 1H, J=1.9 Hz) 7.14 (d, 1H, J=8.3 Hz). ESIMS (m/z): 812.0 ([M+NH$_4$]$^+$), 817.0 ([M+Na]$^+$), 832.9 ([M+K]$^+$).

Example 12

O-[4-(β-D-maltotriosyloxy)-3-methoxybenzyl]-n-hexanoic acid ester (26)

Compound 25-5 (250 mg, 0.390 mmol) in a mixture with O=PPh$_3$ was dissolved in acetone (8 ml) at room temperature, n-hexanoic acid (456 mg, 3.92 mmol) was added, and the reaction mixture was cooled in an ice bath. Novozym 435 (50 mg) and molecular sieves 3A (256 mg) were added. After stirring for 10 minutes, the ice bath was removed and the mixture was heated under reflux for 19 hours. Since acetone evaporated during the reaction, supplemental acetone was added appropriately. Then, the reaction mixture was cooled to room temperature, and the solid was filtered off. Since precipitation occurred in the filtrate, the solid was collected by filtration, and dissolved in methanol, and the mixture was concentrated under reduced pressure. The obtained residue was purified by ODS column chromatography (gradient; water:methanol=17:3→1:4). Since purification was insufficient, the obtained sample was slurried with diethyl ether, filtered and concentrated to give a mixture of β form and α form of O-[4-(β-D-maltotriosyloxy)-3-methoxybenzyl]-n-hexanoic acid ester (26) (as a result of $^1$H-NMR analysis, β form:α form ratio was about 4:1; 17.8 mg, 0.024 mmol, yield 13%) as a colorless solid.

$^1$H-NMR (400 MHz, methanol-d$_4$) δ: 0.86 (t, 3H, J=7.0 Hz), 1.28-1.35 (m, 4H), 1.58-1.66 (m, 2H), 2.35 (t, 2H, J=7.4 Hz), 3.42-3.89 (m, 18H), 3.86 (s, 3H), 4.94 (d, 1H, J=7.7 Hz), 5.15 (d, 1H, J=3.8 Hz), 5.21 (d, 1H, J=3.8 Hz), 6.92 (dd, 1H, J=2.0 Hz, 8.3 Hz), 7.02 (d, 1H, J=2.0 Hz), 7.14 (d, 1H, J=8.3 Hz). ESIMS (m/z): 755.9 ([M+NH$_4$]$^+$), 760.9 ([M+Na]$^+$).

Comparative Example 1

N-[4-(β-D-glucopyranosyl-(1→4)-β-D-glucopyranosyloxy)-3-methoxybenzyl]-8-methylnonanamide (27)

4-Hydroxy-3-methoxybenzylamine hydrochloride (27-1) (316 mg, 1.67 mmol) was dissolved in a mixed solvent of dichloromethane (CH$_2$Cl$_2$, 4 ml) and water (H$_2$O, 4 ml) at room temperature, and the mixture was cooled in an ice bath. Sodium hydrogen carbonate (741 mg, 8.35 mmol) and carbobenzoxy chloride (Cbz-Cl, 0.715 ml, 5.01 mmol) were added. After stirring for 10 minutes, the ice bath was removed and the mixture was warmed to room temperature, and stirred for 1 hour. After 2 times of extraction with dichloromethane (5 ml), the combined organic layer was washed with 15% brine (30 ml). The combined organic layer was dried over anhydrous magnesium sulfate, and filtered, and the filtrate was concentrated under reduced pressure. The residue was purified by silica gel chromatography (gradient; ethyl acetate:n-hexane=4:21→7:28) to give compound 27-2 (375 mg, 1.31 mmol, yield 78%) as a colorless solid.

$^1$H-NMR (400 MHz, CDCl$_3$) δ: 3.86 (s, 3H), 4.30 (d, 2H, J=5.8 Hz), 5.00 (s, 0.7H), 5.14 (s, 2H), 5.57 (s, 0.9H), 6.76-6.78 (m, 2H), 6.86 (d, 1H, J=8.0 Hz), 7.31-7.38 (m, 5H). ESIMS (m/z): 288.0 ([M+H]$^+$), 310.0 ([M+Na]$^+$), 326.0 ([M+K]$^+$).

Then, under an argon atmosphere, compound 27-2 (210 mg, 0.731 mmol) was dissolved in a mixed solvent of toluene (4 ml) and THF (3 ml), and triphenylphosphine (288 mg, 1.10 mmol) and D-cellobiose 2,2',3,3',4',6,6'-heptaacetate (10) (694 mg, 1.10 mmol) were added at room temperature. Then, the reaction mixture was cooled in an ice bath, and diethyl azodicarboxylate 2.2 M toluene solution (0.5 ml, 1.10 mmol) was added dropwise. After stirring for 10 minutes, the ice bath was removed and the mixture was warmed to room temperature, and further stirred for 3 hours. The reaction solution was concentrated under reduced pressure, the insoluble material was filtered off, and the filtrate was concentrated under reduced pressure. The residue was purified by silica gel column chromatography (gradient; ethyl acetate:n-hexane=4:1→3:2) to give a mixture of β form and α form of compound 27-3 (as a result of $^1$H-NMR analysis, β form:α form ratio was about 9:1; 216 mg, 0.238 mmol, yield 32%) as a colorless solid.

$^1$H-NMR (400 MHz, CDCl$_3$) δ: 1.98 (s, 3H), 2.01 (s, 3H), 2.02 (s, 3H), 2.04 (s, 3H), 2.06 (s, 3H), 2.09 (s, 3H), 2.10 (s, 3H), 3.62-3.69 (m, 2H), 3.77 (m, 3H), 3.84 (t, 1H, J=9.4 Hz), 4.06 (dd, 1H, J=2.2 Hz, 12.4 Hz), 4.32 (d, 2H, J=5.8 Hz), 4.38 (dd, 1H, J=4.5 Hz, 12.5 Hz), 4.50-4.54 (m, 2H), 4.87 (d, 1H, J=7.7 Hz), 4.93 (dd, 1H, J=8.0 Hz, 9.3 Hz), 5.07 (t, 1H, J=9.4

Hz), 5.13-5.20 (m, 4H), 5.25 (t, 1H, J=9.4 Hz), 6.75-6.81 (m, 2H), 7.02 (d, 1H, J=8.1 Hz), 7.29-7.36 (m, 5H). ESIMS (m/z): 923.0 ([M+NH$_4$]$^+$), 928.0 ([M+Na]$^+$), 943.7 ([M+K]$^+$).

Then, under an argon atmosphere, a mixture of β form and a form of compound 27-3 (β form:α form ratio was about 9:1; 216 mg, 0.239 mmol) was dissolved in methanol (3.5 ml) at room temperature. Palladium hydroxide/carbon (Pd 20%, Pd(OH)$_2$/C, 216 mg) was added, the atmosphere was substituted with hydrogen and the mixture was stirred for 1 hour. Since the remainder of the starting material was confirmed by thin layer chromatography (TLC), palladium hydroxide/carbon (Pd 20%, 100 mg) was further added and the mixture was stirred for 1 hour. Palladium hydroxide/carbon was filtered off from the reaction mixture, and the filtrate was concentrated under reduced pressure to give a mixture of β form and α form of compound 27-4 (the ratio of β form:α form was difficult to determine from the results of $^1$H-NMR analysis; 124 mg, 0.161 mmol, yield 67%) as a colorless solid.

$^1$H-NMR (400 MHz, CDCl$_3$) δ: 1.98 (s, 3H), 2.01 (s, 3H), 2.02 (s, 3H), 2.04 (s, 3H), 2.06 (s, 3H), 2.09 (s, 3H), 2.11 (s, 3H), 3.64-3.70 (m, 2H), 3.75-3.88 (m, 4H), 4.04-4.15 (m, 3H), 4.38 (dd, 1H, J=4.0 Hz, 12.1 Hz), 4.52-4.54 (m, 2H), 4.84-4.95 (m, 2H), 5.07 (t, 1H, J=9.6 Hz), 5.13-5.20 (m, 3H), 5.25 (t, 1H, J=9.6 Hz), 6.81 (m, 1H), 6.93 (m, 1H), 7.03 (m, 1H). ESIMS (m/z): 772.0 ([M+H]$^+$), 793.9 ([M+Na]$^+$).

Then, a mixture of β form and α form of compound 27-4 (the ratio of β form:α form was difficult to determine from the results of $^1$H-NMR analysis; 124 mg, 0.161 mmol) was dissolved in dichloromethane (5 ml), and 8-MNA (44.6 mg, 0.258 mmol) was added at room temperature. The reaction mixture was cooled in an ice bath, and 1-ethyl-3-(3-dimethylaminopropyl)carbodiimide hydrochloride (WSC hydrochloride, 76.9 mg, 0.401 mmol) was added. After stirring for 10 minutes, the ice bath was removed and the mixture was warmed to room temperature, and further stirred for 17 hours. To the reaction mixture was added water (10 ml), and the mixture was extracted 5 times with dichloromethane (10 ml) at room temperature. The combined organic layer was washed with 15% brine (30 ml), dried over anhydrous magnesium sulfate and filtered. The filtrate was concentrated under reduced pressure, and the residue was purified by silica gel column chromatography (gradient; ethyl acetate:n-hexane=1:4→1:1→16:9→3:1) to give a mixture of β form and α form of compound 27-5 (the ratio of β form:α form was difficult to determine from the results of $^1$H-NMR analysis; 57.3 mg, 0.0619 mmol, yield 39%) as a colorless solid.

$^1$H-NMR (400 MHz, CDCl$_3$) δ: 0.85 (d, 6H, J=6.6 Hz), 1.13-1.17 (m, 2H), 1.27-1.33 (m, 6H), 1.49-1.53 (m, 1H), 1.61-1.67 (m, 2H), 1.98 (s, 3H), 2.01 (s, 3H), 2.03 (s, 3H), 2.04 (s, 3H), 2.06 (s, 3H), 2.09 (s, 3H), 2.11 (s, 3H), 2.20 (t, 2H, J=7.6 Hz), 3.63-3.69 (m, 2H), 3.77-3.87 (m, 1H), 3.79 (s, 3H), 4.04-4.15 (m, 2H), 4.36-4.40 (m, 3H), 4.51-4.55 (m, 2H), 4.87-4.95 (m, 2H), 5.05-5.27 (m, 4H), 6.75 (dd, 1H, J=2.0 Hz, 8.2 Hz), 6.82 (d, 1H, J=2.0 Hz), 7.02 (d, 1H, J=8.2 Hz). ESIMS (m/z): 926.1 ([M+H]$^+$), 948.1 ([M+Na]$^+$), 964.1 ([M+K]$^+$).

Then, compound 27-5 (57.3 mg, 0.0619 mmol) was dissolved in methanol (3 ml), and sodium methoxide 0.5 M methanol solution (75 μl, 0.0375 mmol) was added in an ice bath. The ice bath was removed and the mixture was warmed to room temperature and stirred for 1 hour. Since the remainder of the starting material was confirmed by thin layer chromatography (TLC), sodium methoxide 0.5 M methanol solution (75 μl, 0.0375 mmol) was further added and the mixture was stirred for 1 hour. The reaction solution was neutralized with a strong acidic cation exchange resin (Amberlite IR120B H AG). The resin was filtered off, and the filtrate was concentrated under reduced pressure to give a mixture of β form and α form of N-[4-(β-D-glucopyranosyl-(1→4)-β-D-glucopyranosyloxy)-3-methoxybenzyl]-8-methylnonanamide (27) (as a result of $^1$H-NMR analysis, β form:α form ratio was about 9:1; 39.0 mg, 0.061 mmol, yield 99%) as a colorless solid.

$^1$H-NMR (400 MHz, methanol-d$_4$) δ: 0.88 (d, 6H, J=7.5 Hz), 1.15-1.20 (m, 2H), 1.26-1.38 (m, 6H), 1.48-1.57 (m, 1H), 1.59-1.67 (m, 2H), 2.22 (t, 2H, J=7.5 Hz), 3.24 (t, 1H, J=8.4 Hz), 3.29-3.40 (m, 3H), 3.51-3.70 (m, 5H), 3.83-3.90 (m, 3H), 3.85 (s, 3H), 4.30 (s, 2H), 4.44 (d, 1H, J=7.8 Hz), 4.91 (d, 1H, J=7.6 Hz), 6.82 (dd, 1H, J=2.0 Hz, 8.3 Hz), 6.94 (d, 1H, J=2.0 Hz), 7.09 (d, 1H, J=8.3 Hz). ESIMS (m/z): 632.1 ([M+H]$^+$), 654.2 ([M+Na]$^+$).

Comparative Example 2

N-[4-(β-D-maltotriosyloxy)-3-methoxybenzyl]-8-methylnonanamide (28)

Under an argon atmosphere, compound 27-2 (104 mg, 0.374 mmol) was dissolved in a mixed solvent of toluene (2 ml) and THF (1.5 ml), and triphenylphosphine (119 mg, 0.454 mmol) and compound 25-3 (404 mg, 0.457 mmol) were added at room temperature. Then, the reaction mixture was cooled in an ice bath, and diethyl azodicarboxylate 2.2 M toluene solution (0.2 ml, 0.440 mmol) was added dropwise. After stirring for 10 minutes, the ice bath was removed and the mixture was warmed to room temperature, and further stirred for 14 hours. The reaction solution was concentrated under reduced pressure, the insoluble material was filtered off, and the filtrate was concentrated under reduced pressure. The residue was purified by silica gel column chromatography (gradient; ethyl acetate:n-hexane=1:5→11:9) to give a mixture of β form and α form of compound 28-1 (the ratio of β form:α form was difficult to determine from the results of $^1$H-NMR analysis; 407 mg, 0.526 mmol, yield >99%) as a colorless solid as a mixture of O=PPh$_3$ and compound 25-3. The compound 28-1 (407 mg, 0.526 mmol) was dissolved in methanol (7 ml), and sodium methoxide 5 M methanol solution (100 μl, 5 mmol) was added while cooling in an ice bath. The ice bath was removed and the mixture was warmed to room temperature and stirred for 1 hour. The reaction solution was neutralized with a strong acidic cation exchange resin (Amberlite IR120B H AG). The resin was filtered off, and the filtrate was concentrated under reduced pressure. Since a peak of acetyl group was confirmed by $^1$H-NMR, the obtained compound was dissolved again in MeOH (7 ml) and sodium methoxide 5 M methanol solution (75 μl, 0.375 mmol) was added in an ice bath. The ice bath was removed and the mixture was warmed to room temperature and stirred for 1 hour. The reaction solution was neutralized with a strong acidic cation exchange resin (Amberlite IR120B H AG). The resin was filtered off, and the filtrate was concentrated under reduced pressure and purified by ODS column chromatography (gradient; methanol:water=1:19→1:3→4:1) to give a mixture of β form and α form of compound 28-2 (the ratio of β form:α form was difficult to determine from the results of $^1$H-NMR analysis; 47.2 mg, 0.0610 mmol, yield 14%) as a colorless solid.

$^1$H-NMR (400 MHz, methanol-d$_4$) δ: 3.42 (m, 18H), 3.81 (s, 3H), 4.24 (s, 2H), 4.89 (d, 1H, J=7.8 Hz), 5.15 (d, 1H, J=3.8 Hz), 5.21 (d, 1H, J=3.8 Hz), 6.80-6.83 (m, 1H), 6.92-6.93 (m, 1H), 7.10 (d, 1H, J=8.3 Hz), 7.29-7.37 (m, 5H). ESIMS (m/z): 772.0 ([M+H]$^+$), 796.0 ([M+Na]$^+$), 811.8 ([M+K]$^+$).

Then, under an argon atmosphere, compound 28-2 (47.2 mg, 0.0610 mmol) was dissolved in methanol (4 ml) at room temperature. Palladium hydroxide/carbon (Pd 20%, 47.7 mg) was added, the atmosphere was substituted with hydrogen and the mixture was stirred for 1.5 hours. Palladium hydroxide/carbon was filtered off from the reaction mixture, and the filtrate was concentrated under reduced pressure to give a mixture of α form and β form of compound 28-3 (as a result of $^1$H-NMR analysis, β form:α form ratio was about 1:1; 29.0 mg, 0.0453 mmol, yield 74%) as a colorless solid.

$^1$H-NMR (400 MHz, methanol-$d_4$) both β form and α form are described δ: 3.43-3.89 (m, 21H), 4.91 (d, ½H, J=3.2 Hz), 4.93 (d, ½H, J=3.2 Hz), 5.15 (d, 1H, J=3.8 Hz), 5.21 (d, 1H, J=3.8 Hz), 6.88-6.91 (m, 1H), 7.04 (d, ½H, J=2.1 Hz), 7.05 (d, ½H, J=2.2 Hz), 7.14 (d, ½H, J=8.3 Hz), 7.15 (d, ½H, J=8.2 Hz). ESIMS (m/z): 640.0 ([M+H]$^+$).

Then, a mixture of β form and α form of compound 28-3 (3 form:α form ratio was about 1:1; 29.0 mg, 0.0453 mmol) was suspended in dichloromethane (2 ml), and 8-MNA (12.6 mg, 0.0731 mmol) was added at room temperature. Since compound 28-3 did not dissolve, N,N-dimethylformamide (DMF, 4 ml) was added to dissolve the compound. Then, the reaction mixture was cooled in an ice bath, and WSC hydrochloride (21.8 mg, 0.113 mmol) was added. After stirring for 10 minutes, the ice bath was removed and the mixture was warmed to room temperature, and further stirred for 13 hours. The reaction mixture was concentrated under reduced pressure and the residue was purified by ODS column chromatography (gradient; methanol:water=3:7→17:3→100:0). Since purification was insufficient, the obtained sample was slurried with diethyl ether, filtered and concentrated to give a mixture of β form and α form of N-[4-(β-D-maltotriosyloxy)-3-methoxybenzyl]-8-methylnonanamide (28) (as a result of $^1$H-NMR analysis, β form:α form ratio was about 1:1; 19.4 mg, 0.0244 mmol, yield 53%) as a colorless solid.

$^1$H-NMR (400 MHz, methanol-$d_4$) δ: 0.87-0.89 (m, 6H), 1.10-1.20 (m, 2H), 1.29-1.44 (m, 6H), 1.48-1.68 (m, 3H), 2.21-2.46 (m, 2H), 3.42-3.91 (m, 21H), 4.29-4.58 (m, 2H), 4.89 (d, ½H, J=5.2 Hz), 4.91 (d, ½H, J=5.1 Hz), 5.15 (d, 1H, J=3.8 Hz), 6.71 (d, 1H, J=3.9 Hz), 6.78-6.84 (m, 1H), 6.90 (d, ½H, J=1.8 Hz), 6.95 (d, ½H, J=2.1 Hz), 7.11 (d, ½H, J=8.3 Hz), 7.12 (d, ½H, J=8.2 Hz). ESIMS (m/z): 792.1 ([M+H]$^-$).

Example 13

O-[4-(β-D-glucopyranosyloxy)-3-methoxybenzyl]-3-cyclohexylpropionic acid ester (29)

Under an argon atmosphere, compound 29-1 (1.01 g, 3.46 mmol) was dissolved in toluene (13 ml), and triphenylphosphine (1.49 g, 5.68 mmol) and compound 2 (1.93 g, 5.54 mmol) were added at room temperature. Then, the reaction mixture was cooled in an ice bath, and diethyl azodicarboxylate 2.2 M toluene solution (2.5 ml, 5.50 mmol) was added dropwise. After stirring for 10 minutes, the ice bath was removed and the mixture was warmed to room temperature, and further stirred for 22 hours. The reaction solution was concentrated under reduced pressure, the insoluble material was filtered off, and the filtrate was concentrated under reduced pressure. The residue was purified by silica gel column chromatography (gradient; ethyl acetate:n-hexane=1:9→3:2) to give a mixture of β form and α form of compound 29-2 (as a result of $^1$H-NMR analysis, β form:α form ratio was about 7:3; 932.3 mg, 1.49 mmol, yield 43%) as a colorless solid.

$^1$H-NMR (400 MHz, CDCl$_3$) δ: 0.84-0.92 (m, 2H), 1.16-1.28 (m, 4H), 1.51-1.56 (m, 2H), 1.63-1.76 (m, 5H), 2.04-2.08 (m, 12H), 2.35 (t, 2H, J=7.84 Hz), 3.73-3.78 (m, 1H), 3.82 (s, 3H), 4.07-4.18 (m, 1H), 4.24-4.33 (m, 1H), 4.91-5.00 (m, 1H), 5.04 (s, 2H), 5.11-5.20 (m, 1H), 5.23-5.31 (m, 1H), 5.67-5.75 (m, 1H), 6.86-6.90 (m, 2H), 7.09 (d, 1H, J=7.66 Hz). ESIMS (m/z): 645.2 ([M+Na]$^+$).

Then, a mixture of β form and α form of compound 29-2 (β form:α form ratio was about 7:3; 750 mg, 1.20 mmol) was dissolved in methanol (13 ml) at room temperature, and the reaction mixture was cooled in an ice bath. Triethylamine (13 ml, 96 mmol) was added and, after stirring for 10 minutes, the ice bath was removed and the mixture was heated under reflux for 14.5 hours. The reaction mixture was cooled to room temperature, and concentrated under reduced pressure, and the residue was purified by ODS column chromatography (gradient; water:methanol=100:0→19:1) to give a mixture of β form and α form of O-[4-(β-D-glucopyranosyloxy)-3-methoxybenzyl]-3-cyclohexylpropionic acid ester (29) (as a result of $^1$H-NMR analysis, β form:α form ratio was about 7:3; 300 mg, 0.066 mmol, yield 55%) as a pale-yellow solid.

$^1$H-NMR (400 MHz, methanol-$d_4$) δ: 0.87-0.93 (m, 2H), 1.17-1.24 (m, 4H), 1.51 (q, 2H, J=7.3 Hz), 1.64-1.71 (m, 5H), 2.36 (t, 2H, J=7.7 Hz), 3.39-3.56 (m, 4H), 3.67-3.72 (m, 1H), 3.80-3.90 (m, 1H), 3.86 (s, 3H), 4.90 (d, 1H, J=7.4 Hz), 5.05 (s, 2H), 6.92 (dd, 1H, J=1.8 Hz, 8.3 Hz), 7.02 (d, 1H, J=1.8 Hz), 7.15 (d, 1H, J=8.3 Hz).

Example 14

O-8-methylnonyl-3-[4-(β-D-glucopyranosyloxy)-3-methoxyphenyl]propionic acid ester (30)

By an operation similar to the synthesis of compound 29-2 and using compound 30-1 (1.06 g, 3.16 mmol), a mixture of β form and α form of compound 30-2 (as a result of $^1$H-NMR analysis, β form:α form ratio was about 9:1; 1.71 g, 2.56 mmol, yield 81%) was obtained as a colorless oil.

$^1$H-NMR (400 MHz, methanol-$d_4$) δ: 0.86 (d, 6H, J=6.6 Hz), 1.14-1.17 (m, 2H), 1.30-1.35 (m, 8H), 1.48-1.54 (m, 1H), 1.56-1.62 (m, 2H), 2.03-2.07 (m, 12H), 2.60 (t, 2H, J=7.8 Hz), 2.90 (t, 2H, J=7.8 Hz), 3.72-3.77 (m, 1H), 3.80 (s, 3H), 4.06 (t, 2H, J=6.8 Hz), 4.11-4.17 (m, 1H), 4.28 (dd, 1H, J=5.0 Hz, 12.2 Hz), 4.90-4.92 (m, 1H), 5.13-5.18 (m, 1H), 5.26-5.28 (m, 2H), 6.72 (dd, 1H, J=2.0 Hz, 8.1 Hz), 6.74 (d, 1H, J=2.0 Hz), 7.02 (d, 1H, J=8.1 Hz). ESIMS (m/z): 689.2 ([M+Na]$^+$), 705.2 ([M+K]$^+$).

Then, by an operation similar to the synthesis of O-[4-(β-D-glucopyranosyloxy)-3-methoxybenzyl]-3-cyclohexylpropionic acid ester (29) and using a mixture of β form and α form of compound 30-2 (β form:α form ratio was about 9:1; 1.40 g, 2.09 mmol), a mixture of β form and α form of O-8-methylnonyl-3-[4-(β-D-glucopyranosyloxy)-3-methoxyphenyl]propionic acid ester (30) (as a result of $^1$H-NMR analysis, β form:α form ratio was about 9:1; 959.5 mg, 1.92 mmol, yield 92%) was obtained as a pale-yellow solid.

$^1$H-NMR (400 MHz, CDCl$_3$) δ: 0.86 (t, 6H, J=6.6), 1.12-1.27 (m, 2H), 1.27-1.33 (m, 8H), 1.48-1.62 (m, 3H), 2.61 (t, 2H, J=7.8 Hz), 2.92 (t, 2H, J=7.7 Hz), 3.44-3.48 (m, 1H), 3.60-3.68 (m, 3H), 3.83-3.87 (m, 1H), 3.86 (s, 3H), 3.95 (dd, 1H, J=3.6 Hz, 12.0 Hz), 4.07 (t, 2H, J=6.8 Hz), 4.68-4.70 (m, 1H), 6.74 (dd, 1H, J=1.9 Hz, 8.1 Hz), 6.78 (d, 1H, J=1.9 Hz), 7.06 (d, 1H, J=8.1 Hz). ESIMS (m/z): 521.2 ([M+Na]$^+$), 537.0 ([M+K]$^+$).

Example 15

O-[4-(β-D-glucopyranosyl-(1→4)-β-D-glucopyranosyloxy)-3-methoxybenzyl]-n-tridecanoic acid ester (31)

By an operation similar to the synthesis of compound 22-1 and using compound 31-1 (306 mg, 0.860 mmol), a mixture of β form and α form of compound 31-2 (the ratio of β form:α form was difficult to determine from the results of ¹H-NMR analysis; 723 mg, 0.75 mmol, yield 87%) was obtained as a colorless solid.

¹H-NMR (400 MHz, CDCl₃) δ: 0.88 (t, 3H, J=6.8), 1.25 (m, 18H), 1.61-1.64 (m, 2H), 1.98 (s, 3H), 2.01 (s, 3H), 2.02 (s, 3H), 2.04 (s, 3H), 2.06 (s, 3H), 2.09 (s, 3H), 2.10 (s, 3H), 2.33 (t, 2H, J=7.6 Hz), 3.64-3.69 (m, 2H), 3.81 (s, 3H), 3.81-3.88 (m, 1H), 4.04-4.07 (m, 1H), 4.13 (dd, 1H, J=5.1 Hz, 11.9 Hz), 4.38 (dd, 1H, J=4.6 Hz, 12.4 Hz), 4.52-4.53 (m, 2H), 4.92 (q, 2H, J=7.8 Hz), 5.04-5.27 (m, 6H), 6.82-6.88 (m, 2H), 7.05 (d, 1H, J=8.1 Hz). ESIMS (m/z): 991.4 ([M+Na]⁺).

Then, by an operation similar to the synthesis of O-8-methylnonyl-2-[4-(β-D-glucopyranosyl-(1→4)-β-D-glucopyranosyloxy)-3-methoxyphenyl]acetic acid ester (22) and using a mixture of β form and α form of compound 31-2 (the ratio of β form:α form was difficult to determine; 615 mg, 0.63 mmol), a mixture of β form and α form of O-[4-(β-D-glucopyranosyl-(1→4)-β-D-glucopyranosyloxy)-3-methoxybenzyl]-n-tridecanoic acid ester (31) (the ratio of β form:α form was difficult to determine from the results of ¹H-NMR analysis; 102 mg, 0.15 mmol, yield 24%) was obtained as a colorless solid.

¹H-NMR (400 MHz, methanol-d₄) δ: 0.90 (d, 3H, J=6.9 Hz), 1.26-1.32 (m, 18H), 1.60-1.63 (m, 2H), 2.35 (t, 2H, J=7.4 Hz), 3.22-3.38 (m, 3H), 3.54-3.70 (m, 6H), 3.86 (s, 3H), 3.86-3.91 (s, 3H), 4.45 (d, 1H, J=7.8 Hz), 4.95 (d, 1H, J=7.6 Hz), 5.05 (s, 2H), 6.91 (dd, 1H, J=2.0 Hz, 8.3 Hz), 7.02 (d, 1H, J=2.0 Hz), 7.13 (d, 1H, J=8.3 Hz). ESIMS (m/z): 697.3 ([M+Na]⁺).

Example 16

O-8-methylnonyl-3-[4-(β-D-glucopyranosyl-(1→4)-β-D-glucopyranosyloxy)-3-methoxyphenyl]propionic acid ester (32)

By an operation similar to the synthesis of compound 22-1 and using compound 32-1 (305 mg, 0.910 mmol), a mixture of β form and α form of compound 32-2 (as a result of ¹H-NMR analysis, β form:α form ratio was about 4:1; 448 mg, 0.47 mmol, yield 52%) was obtained as a colorless solid.

¹H-NMR (400 MHz, CDCl₃) δ: 0.86 (d, 6H, J=6.6 Hz), 1.12-1.27 (m, 2H), 1.48-1.54 (m, 1H), 1.98 (s, 3H), 2.01 (s, 3H), 2.02 (s, 3H), 2.04 (s, 3H), 2.06 (s, 3H), 2.09 (s, 3H), 2.10 (s, 3H), 2.59 (t, 2H, J=7.8 Hz), 2.89 (t, 2H, J=7.8 Hz), 3.63-3.70 (m, 2H), 3.78 (s, 3H), 3.82-3.87 (m, 1H), 4.04-4.07 (m, 3H), 4.11-4.15 (m, 1H), 4.37 (dd, 1H, J=4.4 Hz, 12.5 Hz), 4.50-4.55 (m, 2H), 4.87 (d, 1H, J=7.7 Hz), 4.91-4.95 (m, 1H), 5.06 (t, 1H, J=9.6), 5.11-5.19 (m, 2H), 5.24 (t, 1H, J=9.2 Hz), 6.68 (dd, 1H, J=2.0 Hz, 8.1 Hz), 6.73 (d, 1H, J=2.0 Hz), 6.98 (d, 1H, J=8.1 Hz). ESIMS (m/z): 977.4 ([M+Na]⁺), 993.4 ([M+K]⁺).

Then, by an operation similar to the synthesis of O-8-methylnonyl-2-[4-(β-D-glucopyranosyl-(1→4)-β-D-glucopyranosyloxy)-3-methoxyphenyl]acetic acid ester (22) and using a mixture of β form and α form of compound 32-2 (β form:α form ratio was about 4:1; 350 mg, 0.367 mmol), a mixture of β form and α form of compound 32-3, which is a diacetylated compound (the ratio of β form:α form was difficult to determine from the results of ¹H-NMR analysis; 27.2 mg, 0.414 mmol, yield 11%) and a mixture of β form and α form of O-8-methylnonyl-3-[4-(β-D-glucopyranosyl-(1→4)-β-D-glucopyranosyloxy)-3-methoxyphenyl]propionic acid ester (32) (as a result of ¹H-NMR analysis, β form:α form ratio was about 4:1; 69.0 mg, 0.10 mmol, yield 27%) were obtained as colorless solids.

¹H-NMR (400 MHz, methanol-d₄) δ: 0.88 (d, 6H, J=6.6 Hz), 1.15-1.20 (m, 2H), 1.29-1.32 (m, 8H), 1.49-1.61 (m, 3H), 2.62 (t, 2H, J=7.2 Hz), 2.88 (d, 2H, J=7.5 Hz), 3.22-3.26 (m, 1H), 3.30-3.40 (m, 3H), 3.50-3.70 (m, 5H), 3.84 (s, 3H), 3.84-3.90 (m, 3H), 4.05 (t, 2H, J=6.6 Hz), 4.44 (d, 1H, J=7.8 Hz), 4.87 (d, 1H, J=7.7 Hz), 6.76 (dd, 1H, J=1.9 Hz, 8.2 Hz), 6.88 (d, 1H, J=1.9 Hz), 7.06 (d, 1H, J=8.2 Hz).

Example 17

O-[3-(β-D-glucopyranosyl-(1→4)-β-D-glucopyranosyloxy)-4-methoxybenzyl]-8-methylnonanoic acid ester (33)

Compound 33-2 (2.02 g, 11.8 mmol) and compound 33-1 (1.80 g, 11.8 mmol) were mixed at room temperature, Novozym 435 (90 mg) was added and the mixture was heated to 50° C. Using a vacuum pump, the mixture was stirred for 21 hours under reduced pressure. The reaction mixture was cooled to room temperature, hexane (9 ml) was added, the insoluble material was filtered off, and the filtrate was concentrated under reduced pressure. The residue was purified by silica gel column chromatography (gradient; ethyl acetate:n-hexane=1:19→1:5) to give compound 33-3 (3.13 g, 10.2 mmol, yield 86%) as a colorless oil.

¹H-NMR (400 MHz, CDCl₃) δ: 0.85 (d, 6H, J=6.6 Hz), 1.13-1.16 (m, 2H), 1.20-1.36 (m, 6H), 1.47-1.57 (m, 1H), 1.59-1.64 (m, 2H), 2.33 (t, 2H, J=7.6 Hz), 5.64 (s, 1H), 6.82 (d, 1H, J=8.2 Hz), 6.85 (dd, 1H, J=1.8 Hz, 8.2 Hz), 6.94 (d, 1H, J=1.8 Hz). ESIMS (m/z): 331.2 ([M+Na]⁺), 437.2 ([M+K]⁺), 639.4 ([2 m+Na]⁺).

Then, by an operation similar to the synthesis of compound 22-1 and using compound 33-3 (701 mg, 2.27 mmol), a mixture of β form and α form of compound 33-4 (the ratio of β form:α form was difficult to determine from the results of ¹H-NMR analysis; 1.21 g, 1.21 mmol, yield 53%) was obtained as a colorless solid.

¹H-NMR (400 MHz, CDCl₃) δ: 0.85 (d, 6H, J=6.6 Hz), 1.13-1.14 (m, 2H), 1.26-1.30 (m, 6H), 1.49-1.52 (m, 1H), 1.58-1.63 (m, 2H), 1.98 (s, 3H), 2.01 (s, 3H), 2.03 (s, 3H), 2.04 (s, 3H), 2.06 (s, 3H), 2.09 (s, 3H), 2.10 (s, 3H), 2.32 (t, 2H, J=7.6 Hz), 3.66-3.70 (m, 2H), 3.83-3.89 (m, 1H), 3.80 (s, 3H), 4.40-4.25 (m, 3H), 4.38 (dd, 1H, J=4.4 Hz, 12.4 Hz), 4.52-4.54 (s, 2H), 4.91-4.69 (m, 2H), 4.99 (s, 2H), 5.02-5.28 (m, 3H), 6.86 (d, 1H, J=8.1 Hz), 7.05-7.08 (m, 2H). ESIMS (m/z): 949.5 ([M+Na]⁺), 965.5 ([M+K]⁺).

Then, by an operation similar to the synthesis of O-8-methylnonyl-2-[4-(β-D-glucopyranosyl-(1→4)-β-D-glucopyranosyloxy)-3-methoxyphenyl]acetic acid ester (22) and using a mixture of β form and α form of compound 33-4 (the ratio of β form:α form was difficult to determine; 662 mg, 0.714 mmol), a mixture of β form and α form of O-[3-(β-D-glucopyranosyl-(1→4)-β-D-glucopyranosyloxy)-4-methoxybenzyl]-8-methylnonanoic acid ester (33) (as a result of ¹H-NMR analysis, β form:α form ratio was about 4:1; 125 mg, 0.197 mmol, yield 25%) was obtained as a colorless solid.

¹H-NMR (400 MHz, methanol-d₄) δ: 0.87 (d, 6H, J=6.6 Hz), 1.14-1.19 (m, 2H), 1.24-1.32 (m, 6H), 1.48-1.55 (m, 1H), 1.57-1.63 (m, 2H), 2.34 (t, 2H, J=7.3 Hz), 3.23-3.40 (m, 5H), 3.52-3.71 (m, 6H), 3.85-3.90 (m, 3H), 3.86 (s, 3H), 4.45 (d, 1H, J=7.9), 4.49 (d, 1H, J=7.6 Hz), 5.01 (d, 1H, J=12.1 Hz), 5.05 (d, 1H, J=12.1 Hz), 6.98 (d, 1H, J=8.4 Hz), 7.03 (dd, 1H, J=1.8 Hz, 8.4 Hz), 7.18 (d, 1H, J=1.8 Hz). ESIMS (m/z): 655.2 ([M+Na]⁺).

Example 18

O-[3-(β-D-glucopyranosyloxy)-4-methoxybenzyl]-8-methylnonanoic acid ester (34)

By an operation similar to the synthesis of compound 29-2 and using compound 33-3 (715 mg, 2.32 mmol), a mixture of β form and α form of compound 34-1 (as a result of $^1$H-NMR analysis, β form:α form ratio was about 4:1; 928 mg, 1.45 mmol, yield 63%) was obtained as a colorless solid.

$^1$H-NMR (400 MHz, CDCl$_3$) δ: 0.85 (d, 6H, J=6.6 Hz), 1.13-1.15 (m, 2H), 1.24-1.34 (m, 6H), 1.47-1.54 (m, 1H), 1.58-1.65 (m, 2H), 2.04-2.08 (m, 12H), 2.32 (t, 2H, J=7.6 Hz), 3.76-3.84 (m, 1H), 3.82 (s, 3H), 4.07-4.21 (m, 1H), 4.26-4.31 (m, 1H), 4.97-5.02 (m, 1H), 5.00 (s, 2H), 5.12-5.19 (m, 1H), 5.26-5.30 (m, 2H), 6.86-6.89 (m, 1H), 7.06-7.09 (m, 1H), 7.13 (d, 1H, J=2.0 Hz). ESIMS (m/z): 661.4 ([M+Na]$^+$), 677.1 ([M+K]$^+$).

Then, by an operation similar to the synthesis of O-[4-(β-D-glucopyranosyloxy)-3-methoxybenzyl]-3-cyclohexylpropionic acid ester (29) and using a mixture of β form and α form of compound 34-1 (β form:α form ratio was about 4:1; 586 mg, 0.917 mmol), a mixture of β form and α form of O-[3-(β-D-glucopyranosyloxy)-4-methoxybenzyl]-8-methylnonanoic acid ester (34) (the ratio of β form:α form was difficult to determine from the results of $^1$H-NMR analysis; 145 mg, 0.31 mmol, yield 34%) was obtained as a colorless solid.

$^1$H-NMR (400 MHz, methanol-d$_4$) δ: 0.86 (d, 6H, J=1.4 Hz), 1.13-1.19 (m, 2H), 1.23-1.34 (m, 6H), 1.48-1.55 (m, 1H), 1.57-1.64 (m, 2H), 2.34 (t, 2H, J=7.2 Hz), 3.40-3.52 (m, 4H), 3.68-3.72 (m, 1H), 3.86-3.90 (m, 1H), 3.86 (s, 3H), 4.90 (d, 1H, J=7.5 Hz), 5.01 (d, 1H, J=12.1 Hz), 5.05 (d, 1H, J=12.1 Hz), 6.98 (d, 1H, J=8.3 Hz), 7.02 (dd, 1H, J=1.8 Hz, 8.3 Hz), 7.20 (d, 1H, J=1.8 Hz). ESIMS (m/z): 493.0 ([M+Na]$^+$), 509.0 ([M+K]$^+$), 963.2 ([2 m+Na]$^+$).

Example 19

O-[4-(β-D-glucopyranosyl-(1→4)-β-D-glucopyranosyloxy)-3-methoxybenzyl]-8-methyl-6-nonenoic acid ester (35)

By an operation similar to the synthesis of compound 22-1 and using compound 35-1 (346 mg, 1.13 mmol), a mixture of β form and α form of compound 35-2 (as a result of $^1$H-NMR analysis, β form:α form ratio was about 9:1; 191 mg, 0.21 mmol, yield 19%) was obtained as a colorless solid.

$^1$H-NMR (400 MHz, CDCl$_3$) δ: 0.94 (d, 6H, J=6.8 Hz), 1.23-1.31 (m, 1H), 1.33-1.41 (m, 2H), 1.59-1.67 (m, 3H), 1.98 (s, 3H), 2.00 (s, 3H), 2.02 (s, 3H), 2.04 (s, 3H), 2.06 (s, 3H), 2.08 (s, 3H), 2.10 (s, 3H), 2.17-2.25 (m, 1H), 2.34 (t, 2H, J=7.5 Hz), 3.64-3.69 (m, 2H), 3.80 (s, 3H), 3.78-3.87 (m, 1H), 4.04-4.07 (m, 1H), 4.13 (dd, 1H, J=5.2 Hz, 11.8 Hz), 4.37 (dd, 1H, J=4.4 Hz, 12.4 Hz), 4.51-4.53 (m, 2H), 4.88-4.95 (m, 2H), 5.03-5.39 (m, 6H), 5.03 (s, 2H), 6.84-6.88 (m, 2H), 7.04 (d, 1H, J=8.1 Hz). ESIMS (m/z): 947.3 ([M+Na]$^+$).

Then, by an operation similar to the synthesis of O-8-methylnonyl-2-[4-(β-D-glucopyranosyl-(1→4)-β-D-glucopyranosyloxy)-3-methoxyphenyl]acetic acid ester (22) and using a mixture of β form and α form of compound 35-2 (β form:α form ratio was about 9:1; 147 mg, 0.159 mmol), a mixture of β form and α form of O-[4-(β-D-glucopyranosyl-(1→4)-β-D-glucopyranosyloxy)-3-methoxybenzyl]-8-methyl-6-nonenoic acid ester (35) (the ratio of β form:α form was difficult to determine from the results of $^1$H-NMR analysis; 26.1 mg, 0.041 mmol, yield 26%) was obtained as a colorless solid.

$^1$H-NMR (400 MHz, methanol-d$_4$) δ: 0.95 (d, 6H, J=6.7 Hz), 1.33-1.40 (m, 2H), 1.58-1.65 (m, 2H), 1.96-2.00 (m, 2H), 2.17-2.25 (m, 1H), 2.35 (t, 2H, J=7.4 Hz), 3.22-3.40 (m, 2H), 3.53-3.70 (m, 6H), 3.86 (s, 3H), 3.86-3.90 (m, 4H), 4.45 (d, 1H, J=7.8 Hz) 4.95 (d, 1H, J=7.6 Hz), 5.06 (s, 2H), 5.53-5.37 (m, 2H), 6.91 (dd, 1H, J=1.7 Hz, 8.2 Hz), 7.02 (d, 1H, J=1.7 Hz), 7.13 (d, 1H, J=8.2 Hz). ESIMS (m/z): 653.2 ([M+Na]$^+$), 669.0 ([M+K]$^+$).

Example 20

O-[4-(β-D-glucopyranosyl-(1→4)-β-D-glucopyranosyloxy)-3-methoxybenzyl]-7-methyloctanoic acid ester (36)

By an operation similar to the synthesis of compound 22-1 and using compound 36-1 (544 mg, 1.84 mmol), a mixture of β form and α form of compound 36-2 (as a result of $^1$H-NMR analysis, β form:α form ratio was about 4:1; 403 mg, 0.44 mmol, yield 24%) was obtained as a colorless solid.

$^1$H-NMR (400 MHz, CDCl$_3$) δ: 0.85 (d, 6H, J=6.6 Hz), 1.12-1.17 (m, 2H), 1.24-1.33 (m, 4H), 1.45-1.55 (m, 1H), 1.59-1.67 (m, 2H), 1.98 (s, 3H), 2.01 (s, 3H), 2.03 (s, 3H), 2.04 (s, 3H), 2.06 (s, 3H), 2.09 (s, 3H), 2.10 (s, 3H), 2.34 (t, 2H, J=7.6 Hz), 3.64-6.69 (m, 2H), 3.79-3.90 (m, 1H), 3.81 (s, 3H), 4.06 (dd, 1H, J=2.3 Hz, 12.5 Hz), 4.09-4.16 (m, 1H), 4.38 (dd, 1H, J=4.4 Hz, 12.5 Hz), 4.51-4.55 (m, 2H), 4.89-4.95 (m, 2H), 5.04 (s, 2H), 5.04-5.23 (m, 4H), 6.85 (dd, 1H, J=2.0 Hz, 8.1 Hz), 6.88 (d, 1H, J=2.0 Hz), 7.10 (d, 1H, J=8.1 Hz). ESIMS (m/z): 935.3 ([M+Na]$^+$).

Then, by an operation similar to the synthesis of O-8-methylnonyl-2-[4-(β-D-glucopyranosyl-(1→4)-β-D-glucopyranosyloxy)-3-methoxyphenyl]acetic acid ester (22) and using a mixture of β form and α form of compound 36-2 (β form:α form ratio was about 4:1; 363 mg, 0.397 mmol), a mixture of β form and α form of O-[4-(β-D-glucopyranosyl-(1→4)-β-D-glucopyranosyloxy)-3-methoxybenzyl]-7-methyloctanoic acid ester (36) (as a result of $^1$H-NMR analysis, β form:α form ratio was about 4:1; 30.2 mg, 0.049 mmol, theoretical yield 33%) was obtained as a colorless solid.

$^1$H-NMR (400 MHz, methanol-d$_4$) δ: 0.88 (d, 6H, J=6.6 Hz), 1.14-1.19 (m, 2H), 1.29-1.32 (m, 4H), 1.46-1.55 (m, 1H), 1.56-1.64 (m, 2H), 2.35 (t, 2H, J=7.5 Hz), 3.22-3.40 (m, 4H), 3.52-3.70 (m, 5H), 3.86-3.92 (m, 3H), 3.86 (s, 3H), 4.45 (d, 1H, J=7.9 Hz), 4.95 (d, 1H, J=7.6 Hz), 5.06 (s, 2H), 6.91 (dd, 1H, J=1.9 Hz, 8.3 Hz), 7.02 (d, 1H, J=1.9 Hz), 7.13 (d, 1H, J=8.3 Hz).

Example 21

O-[4-(β-D-glucopyranosyl-(1→4)-β-D-glucopyranosyloxy)-3-methoxybenzyl]-n-propionic acid ester (38)

n-Propionic acid (37) (1.73 g, 23.4 mmol) and vanillyl alcohol (5) (3.50 g, 22.7 mmol) were mixed at room temperature, Novozym 435 (350 mg) and acetone (7 ml) were added, and the mixture was heated under reflux for 14 hours. Since the remainder of the starting material was confirmed by TLC, acetone (7 ml) and Novozym 435 (349 mg) were added again, and the mixture was further stirred for 48 hours with heating. Since acetone evaporated during the reaction, supplemental acetone was added appropriately. The reaction mixture was cooled to room temperature, hexane (20 ml) was added, the insoluble material was filtered off, and the filtrate was concentrated under reduced pressure. The residue was purified by ODS column chromatography (gradient; ethyl acetate:n-hexane=1:99→17:3) to give compound 38-1 (3.94 mg, 17.6 mmol, yield 78%) as a colorless liquid.

$^1$H-NMR (400 MHz, CDCl$_3$) δ: 1.45 (t, 3H, J=7.6 Hz), 2.36 (q, 2H, J=7.6 Hz), 3.90 (s, 3H), 5.03 (t, 2H), 5.63 (s, 1H), 6.87-6.91 (m, 3H).

Then, by an operation similar to the synthesis of compound 22-1 and using compound 38-1 (621 mg, 2.85 mmol), a mixture of β form and α form of compound 38-2 (the ratio of β form:α form was difficult to determine from the results of $^1$H-NMR analysis; 350 mg, 0.42 mmol, theoretical yield 22%) was is obtained as a colorless solid.

$^1$H-NMR (400 MHz, CDCl$_3$) δ: 1.16 (t, 3H, J=7.6 Hz), 1.98 (s, 3H), 2.01 (s, 3H), 2.03 (s, 3H), 2.04 (s, 3H), 2.06 (s, 3H), 2.09 (s, 3H), 2.10 (s, 3H), 2.37 (q, 2H, J=7.6 Hz), 3.65-3.69 (m, 2H), 3.81 (s, 3H), 3.81-3.87 (m, 1H), 4.06 (dd, 1H, J=2.0 Hz, 12.4 Hz), 4.13 (dd, 1H, J=5.3 Hz, 11.8 Hz), 4.38 (dd, 1H, J=4.4 Hz, 12.4 Hz), 4.52-4.54 (m, 2H), 4.89-4.95 (m, 2H), 5.04 (s, 2H), 5.04-5.09 (m, 1H), 5.12-5.28 (m, 3H), 6.84-6.87 (m, 1H), 6.89 (d, 1H, J=1.8 Hz), 7.05 (d, 1H, J=8.1 Hz). ESIMS (m/z): 850.9 ([M+Na]$^+$), 867.0 ([M+K]$^+$).

Then, by an operation similar to the synthesis of O-8-methylnonyl-2-[4-(β-D-glucopyranosyl-(1→4)-β-D-glucopyranosyloxy)-3-methoxyphenyl]acetic acid ester (22) and using a mixture of β form and α form of compound 38-2 (the ratio of β form:α form was difficult to determine; 252 mg, 0.304 mmol), a mixture of β form and α form of O-[4-(1-D-glucopyranosyl-(1→4)-β-D-glucopyranosyloxy)-3-methoxybenzyl]-n-propionic acid ester (38) (the ratio of β form:α form was difficult to determine from the results of $^1$H-NMR analysis; 183 mg, 0.342 mmol, yield >99%) was obtained as a brown solid.

$^1$H-NMR (400 MHz, methanol-d$_4$) δ: 1.12 (t, 3H, J=7.6 Hz), 2.37 (q, 2H, J=7.6 Hz), 3.19 (m, 4H), 3.52-3.71 (m, 5H), 3.86 (s, 3H), 3.81-3.95 (m, 3H), 4.45 (d, 1H, J=7.8 Hz), 4.95 (d, 1H, J=7.6 Hz), 5.06 (s, 2H), 6.87-6.93 (m, 1H), 7.02-7.03 (m, 1H), 7.13 (d, 1H, J=8.3 Hz). ESIMS (m/z): 556.8 ([M+Na]$^+$).

Example 22

O-[4-(β-D-glucopyranosyl-(1→4)-β-D-glucopyranosyloxy)-3-methoxybenzyl]-n-hexanoic acid ester (39)

A mixture of β form and α form of 4-(β-D-glucopyranosyl-(1→4)-β-D-glucopyranosyloxy)-3-methoxybenzyl alcohol (14) (as a result of $^1$H-NMR analysis, β form:α form ratio was about 7:1; 219 mg, 0.457 mmol) was dissolved in acetone (8 ml) at room temperature, n-hexanoic acid (531 mg, 4.57 mmol) was added, and the reaction mixture was cooled in an ice bath. Novozym 435 (45.8 mg) and anhydrous magnesium sulfate (224 mg) were added. After stirring for 10 minutes, the ice bath was removed and the mixture was heated under reflux for 16 hours. Since acetone evaporated during the reaction, supplemental acetone was added appropriately. Then, the reaction mixture was cooled to room temperature, and the solid was filtered off. Purification by ODS column chromatography (gradient; water:methanol=57:43→3:17) gave a mixture of β form and α form of O-[4-(β-D-glucopyranosyl-(1→4)-β-D-glucopyranosyloxy)-3-methoxybenzyl]-n-hexanoic acid ester (39) (as a result of $^1$H-NMR analysis, β form:α form ratio was about 9:1; 103 mg, 0.179 mmol, yield 39%) as a colorless solid.

$^1$H-NMR (400 MHz, methanol-d$_4$) δ: 0.89 (t, 3H, J=7.0 Hz), 1.28-1.35 (m, 4H), 1.58-1.66 (m, 2H), 2.35 (t, 2H, J=7.4 Hz), 3.22-3.40 (m, 4H), 3.53-3.71 (m, 5H), 3.85-3.91 (m, 3H), 3.86 (s, 3H), 4.44 (d, 1H, J=7.8 Hz), 4.95 (d, 1H, J=7.6 Hz), 5.06 (s, 2H), 6.91 (dd, 1H, J=1.9 Hz, 8.3 Hz), 7.02 (d, 1H, J=1.9 Hz), 7.13 (d, 1H, J=8.3 Hz). ESIMS (m/z): 599.1 ([M+Na]$^+$).

Example 23

O-[4-(β-D-maltotriosyloxy)-3-methoxyphenethyl]-8-methylnonanoic acid ester (40)

Compound 40-1 (5.00 g, 29.7 mmol) was dissolved in ethyl acetate (40 ml) at room temperature, and the mixture was cooled in an ice bath. Novozym 435 (1.00 g) was added and, after stirring for 10 minutes, the ice bath was removed and the mixture was heated under reflux for 18 hours. Then, the reaction mixture was cooled to room temperature, and the solid was filtered off. The filtrate was concentrated under reduced pressure, and the residue was purified by silica gel column chromatography (gradient; ethyl acetate:n-hexane=1:19→1:3) to give compound 40-2 (4.59 g, 21.8 mmol, yield 73%) as a colorless solid.

$^1$H-NMR (400 MHz, methanol-d$_4$) δ: 2.00 (s, 3H), 2.83 (t, 2H, J=7.1 Hz), 3.84 (s, 3H), 4.21 (t, 2H, J=7.1 Hz), 6.65 (dd, 1H, J=1.9 Hz, 8.0 Hz), 6.72 (d, 1H, J=8.0 Hz), 6.80 (d, 1H, J=1.9 Hz). ESIMS (m/z): 233.0 ([M+Na]$^+$).

By an operation similar to the synthesis of compound 25-4 and using compound 40-2 (736 mg, 3.50 mmol), a mixture of β form and α form of compound 40-3 was obtained as a mixture with O=PPh$_3$ and compound 25-3 (the ratio of β form:α form was difficult to determine; 482 mg, 0.431 mmol, yield 20%). Then, by an operation similar to the synthesis of compound 25-4 and using compound 40-3 (238 mg), a mixture of compound 40-4 and compound 25-1 ($^1$H-NMR analysis result, theoretical yield of object product: 99.5 mg, 0.14 mmol, yield 66%) was obtained as a colorless solid. Then, compound 40-4 (80.7 mg, 0.126 mmol) in the mixture was dissolved in a mixed solvent of acetone (4 ml) and dioxane (2 ml) at room temperature, 8-MNA (217 mg, 1.26 mmol) was added, and the reaction mixture was cooled in an ice bath. Novozym 435 (26.2 mg) and anhydrous magnesium sulfate (89.1 mg) were added and, after stirring for 10 minutes, the ice bath was removed and the mixture was stirred with heating at 50° C. for 20 hours. Since acetone evaporated during the reaction, supplemental acetone was added appropriately. Then, the reaction mixture was cooled to room temperature, and the solid was filtered off. Purification by ODS column chromatography (gradient; water:methanol=100:0→17:3→0:100) was performed. Since purification was insufficient, the obtained sample was slurried with diethyl ether, filtered and concentrated to give a mixture of β form and α form of O-[4-(β-D-maltotriosyloxy)-3-methoxyphenethyl]-8-methylnonanoic acid ester (40) (as a result of $^1$H-NMR analysis, β form:α form ratio was about 4:1; 11.4 mg, 0.014 mmol, yield 26%) as a colorless solid.

$^1$H-NMR (400 MHz, methanol-d$_4$) δ: 0.89 (d, 6H, J=6.6 Hz), 1.16-1.21 (m, 2H), 1.29-1.32 (m, 6H), 1.49-1.60 (m, 3H), 2.30 (t, 2H, J=7.4 Hz), 2.89 (t, 2H, J=6.9 Hz), 3.44-3.94 (m, 18H), 3.86 (m, 3H), 4.27 (t, 2H, J=6.9 Hz), 4.90 (d, 1H, J=7.3 Hz), 5.16 (d, 1H, J=3.9 Hz), 5.20 (d, 1H, J=3.8 Hz), 6.79 (dd, 1H, J=2.0 Hz, 8.3 Hz), 6.91 (d, 1H, J=2.0 Hz), 7.10 (d, 1H, J=8.3 Hz). ESIMS (m/z): 808.9 ([M+H]$^+$), 830.9 ([M+Na]$^+$), 846.7 ([M+K]$^+$).

Example 24

O-[4-(β-D-maltotriosyloxy)-3-methoxyphenethyl]-n-hexanoic acid ester (41)

Compound 40-4 (118 mg, 0.169 mmol) in the mixture was dissolved in a mixed solvent of acetone (5 ml) and dioxane (3 ml) at room temperature, n-hexanoic acid (196 mg, 1.69 mmol) was added, and the reaction mixture was cooled in an ice bath. Novozym 435 (36.6 mg) and anhydrous magnesium sulfate (118 mg) were added and, after stirring for 10 minutes, the ice bath was removed and the mixture was stirred with heating at 50° C. for 17 hours. Since acetone evaporated during the reaction, supplemental acetone was added appropriately. Then, the reaction mixture was cooled to room temperature, and the solid was filtered off. Purification by ODS column chromatography (gradient; water:methanol=100:0→17:3→0:100) was performed. Since purification was insufficient, the obtained sample was slurried with diethyl ether, filtered and concentrated to give a mixture of β form and α form of O-[4-(3-D-maltotriosyloxy)-3-methoxyphenethyl]-n-hexanoic acid ester (41) (as a result of H-NMR analysis, β form:α form ratio was about 4:1; 51.5 mg, 0.0684 mmol, yield 94%) as a colorless solid.

$^1$H-NMR (400 MHz, methanol-$d_4$) δ: 0.91 (t, 3H, J=7.0 Hz), 1.23-1.35 (m, 4H), 1.55-1.62 (m, 2H), 2.29 (t, 2H, J=7.4 Hz), 2.89 (t, 2H, J=6.8 Hz), 3.43-3.93 (m, 18H), 3.87 (s, 3H), 4.27 (t, 2H, J=6.8 Hz), 4.90 (d, 1H, J=7.8 Hz), 5.16 (d, 1H, J=3.8 Hz), 5.22 (d, 1H, J=3.9 Hz), 6.74 (dd, 1H, J=1.9 Hz, 9.8 Hz), 6.91 (d, 1H, J=1.9 Hz), 7.11 (d, 1H, J=9.8 Hz). ESIMS (m/z): 775.0 ([M+Na]$^+$).

Example 25

O-[4-(β-D-maltosyloxy)-3-methoxybenzyl]-n-hexanoic acid ester (42)

D-maltose (42-1) (10.1 g, 28.2 mmol) was dissolved in pyridine (40 ml) at room temperature, the mixture was cooled in an ice bath, acetic anhydride (19.6 ml, 207 mmol) was added, and the reaction mixture was warmed to room temperature and stirred for 20.5 hours. Since the remainder of the starting material was confirmed by thin layer chromatography (TLC), the reaction mixture was cooled in an ice bath, pyridine (24 ml) and acetic anhydride (12 ml, 127 mmol) were added, the ice bath was removed and the mixture was stirred at room temperature for 3 hours. The reaction mixture was cooled in an ice bath, water (100 ml) was slowly added, the ice bath was removed and the mixture was extracted 5 times with ethyl acetate (100 ml) at room temperature. The combined organic layer was washed twice with 3 N HCl (100 ml), then with water (100 ml), saturated aqueous sodium hydrogen carbonate solution (100 ml), and 15% brine (100 ml). The organic layer was dried over anhydrous magnesium sulfate, the solid was filtered off, and the filtrate was concentrated under reduced pressure. The residue was purified by silica gel column chromatography (gradient; ethyl acetate:n-hexane=46:54→66:34) to give D-maltose octaacetate (3.29 g) and a mixture (13.6 g) of D-maltose heptaacetate and compound 42-2 as a colorless solid. The mixture was dissolved in pyridine (21 ml) at room temperature, cooled in an ice bath, acetic anhydride (10.5 ml, 111 mmol) and N,N-dimethyl-4-aminopyridine (266 mg, 2.17 mmol) were added, and the reaction mixture was warmed to room temperature and stirred for 4 hours. The reaction mixture was cooled in an ice bath, water (100 ml) was slowly added, the ice bath was removed and the mixture was extracted 5 times with ethyl acetate (100 ml) at room temperature. The combined organic layer was washed twice with 3 N HCl (100 ml), then with water (100 ml), saturated aqueous sodium hydrogen carbonate solution (100 ml) and 15% brine (100 ml). The organic layer was dried over anhydrous magnesium sulfate, the solid was filtered off, and the filtrate was concentrated under reduced pressure. The residue was purified by silica gel column chromatography (gradient; ethyl acetate:n-hexane=46:54→66:34) to give a mixture of β form and α form of compound 42-2 (the ratio of β form:α form was difficult to determine from the results of $^1$H-NMR analysis; 14.3 g) as a white solid (total 17.6 g, 26.0 mmol, yield 92%).

$^1$H-NMR (400 MHz, CDCl$_3$) δ: 2.00 (s, 3H), 2.02 (s, 3H), 2.02 (s, 3H), 2.03 (s, 3H), 2.05 (s, 3H), 2.10 (s, 3H), 2.10 (s, 3H), 2.14 (s, 3H), 3.84 (ddd, 1H, J=2.6 Hz, 4.2 Hz, 10.1 Hz), 3.94 (ddd, 1H, J=2.4 Hz, 4.2 Hz, 10.1 Hz), 4.01-4.07 (m, 2H), 4.21-4.26 (m, 2H), 4.46 (dd, 1H, J=2.4 Hz, 12.3 Hz), 4.86 (dd, 1H, J=4.0 Hz, 10.5 Hz), 4.98 (dd, 1H, J=4.0 Hz, 10.5 Hz), 4.98 (dd, 1H, J=8.2 Hz, 9.2 Hz), 5.06 (dd, 1H, J=10.0 Hz, 10.0 Hz), 5.27-5.38 (m, 2H), 5.41 (d, 1H, J=4.0 Hz), 5.74 (d, 1H, J=8.2 Hz). ESIMS (m/z): 701.0 ([M+Na]$^+$), 716.8 ([M+K]$^+$).

Then, a mixture of β form and α form of compound 42-2 (the ratio of β form:α form was difficult to determine; 3.29 g, 4.85 mmol) was dissolved in N,N-dimethylformamide (10 ml) at room temperature, the mixture was cooled in an ice bath, ammonium acetate (935 mg, 12.1 mmol) was added, and the mixture was heated to 50° C. and stirred for 2 hours. The reaction mixture was cooled in an ice bath, water (50 ml) was slowly added, the ice bath was removed and the mixture was extracted 5 times with ethyl acetate (50 ml) at room temperature. The combined organic layer was washed with water (50 ml), and then with 15% brine (40 ml). The organic layer was dried over anhydrous magnesium sulfate, the solid was filtered off, and the filtrate was concentrated under reduced pressure. The residue was purified by silica gel column chromatography (gradient; ethyl acetate:n-hexane=46:54→66:34) to give a mixture of β form and α form of compound 42-3 (the ratio of β form:α form was difficult to determine from the results of $^1$H-NMR analysis; 1.23 g, 1.94 mmol, yield 40%) as a colorless solid.

$^1$H-NMR (400 MHz, CDCl$_3$) δ: 2.01 (s, 3H), 2.02 (s, 3H), 2.03 (s, 3H), 2.06 (s, 3H), 2.07 (s, 3H), 2.10 (s, 3H), 2.15 (s, 3H), 3.95-4.02 (m, 2H), 4.06 (dd, 1H, J=2.2 Hz, 12.4 Hz), 4.21-4.26 (m, 3H), 4.28-4.52 (m, 1H), 4.78-4.81 (m, 1H), 4.87 (dd, 1H, J=4.0 Hz, 10.5 Hz), 5.06 (dd, 1H, J=9.8 Hz, 9.8 Hz), 5.28-5.41 (m, 2H), 5.45 (d, 1H, J=4.0 Hz), 5.59 (dd, 1H, J=8.9 Hz, 10.2 Hz). ESIMS (m/z): 659.0 ([M+Na]$^+$), 675.0 ([M+K]$^+$).

Then, under an argon atmosphere, compound 42-3 (1.01 g, 1.58 mmol) was dissolved in a mixed solvent of tetrahydrofuran (9.5 ml) and toluene (9.5 ml) at room temperature, and triphenylphosphine (659 mg, 2.51 mmol) and compound 6 (494 mg, 2.51 mmol) were added. The reaction mixture was cooled in an ice bath, diethyl azodicarboxylate 2.2 M toluene solution (1.17 ml, 2.57 mmol) was added dropwise, the ice bath was removed and the mixture was warmed to room temperature, and stirred for 6 hours. The reaction solution was concentrated under reduced pressure, the insoluble material was filtered off, and the filtrate was concentrated under reduced pressure. The residue was purified by silica gel column chromatography (gradient; ethyl acetate:n-hexane=31:69→55:45) to give a mixture of β form and α form of compound 42-4 (as a result of $^1$H-NMR analysis, β form:α form ratio was about 15:1; 906 mg, 1.11 mmol, yield 70%) as a colorless solid.

$^1$H-NMR (400 MHz, CDCl$_3$) δ: 2.01 (s, 3H), 2.03 (s, 3H), 2.04 (s, 3H), 2.05 (s, 3H), 2.05 (s, 3H), 2.10 (s, 3H), 2.11 (s,

3H), 2.11 (s, 3H), 3.77 (ddd, 1H, J=2.5 Hz, 4.6 Hz, 10.0 Hz), 3.82 (s, 3H), 3.97 (ddd, 1H, J=2.3 Hz, 3.9 Hz, 10.0 Hz), 4.04-4.13 (m, 2H), 4.23-4.30 (m, 2H), 4.49 (dd, 1H, J=2.9 Hz, 12.0 Hz), 4.87 (dd, 1H, J=4.0 Hz, 10.5 Hz), 5.00-5.14 (m, 3H), 5.04 (s, 2H), 5.32 (dd, 1H, J=8.9 Hz, 8.9 Hz), 5.37 (dd, 1H, J=9.6 Hz, 10.4 Hz), 5.44 (d, 1H, J=4 Hz), 6.88-6.91 (m, 2H), 7.07 (d, 1H, J=7.9 Hz). ESIMS (m/z): 837.0 ([M+Na]+), 852.8 ([M+K]+).

Then, a mixture of β form and α form of compound 42-4 (as a result of $^1$H-NMR analysis, β form:α form ratio was about 15:1) was dissolved in methanol (6 ml) at room temperature, and the mixture was cooled in an ice bath. Sodium methoxide 0.5 M methanol solution (450 µl, 0.23 mmol) was added, the ice bath was removed and the mixture was warmed to room temperature and stirred for 1 hour. The reaction solution was neutralized with a strong acidic cation exchange resin (Amberlite IR120B H AG), the resin was filtered off, and the filtrate was concentrated under reduced pressure to give a mixture of β form and α form of compound 42-5 (the ratio of β form:α form was difficult to determine from the results of $^1$H-NMR analysis; 345 mg, 0.721 mmol, yield 98%) as a colorless solid.

$^1$H-NMR (400 MHz, methanol-d$_4$) δ: 3.26-3.32 (m, 1H), 3.82 (s, 3H), 3.47 (dd, 1H, J=3.8 Hz, 9.8 Hz), 3.51-3.59 (m, 2H), 3.61-3.78 (m, 5H), 3.82-3.92 (m, 3H), 3.82 (s, 3H), 4.56 (s, 2H), 4.93 (d, 1H, J=7.8 Hz), 5.22 (d, 1H, J=3.8 Hz), 6.90 (dd, 1H, J=1.9 Hz, 8.3 Hz), 7.05 (d, 1H, J=1.9 Hz), 7.15 (d, 1H, J=8.3 Hz). ESIMS (m/z): 500.8 ([M+Na]+), 516.9 ([M+K]+).

Then, a mixture of β form and α form of compound 42-5 (the ratio of β form:α form was difficult to determine; 110 mg, 0.230 mmol) was suspended in acetone (4 ml) at room temperature, and the compound n-hexanoic acid (317 µl, 2.52 mmol) was mixed at room temperature. Novozym 435 (55.8 mg) and molecular sieves 3A (110 mg) were added, acetone (5 ml) was further added, and the reaction mixture was stirred with heating under reflux for 16 hours. Then, the reaction mixture was cooled to room temperature, methanol (10 ml) was added, Novozym 435 and the molecular sieves were filtered off, and the filtrate was concentrated under reduced pressure. The residue was purified by ODS column chromatography (gradient; water:methanol=70:30→40:60) to give a mixture of β form and α form of O-[4-(β-D-maltosyloxy)-3-methoxybenzyl]-n-hexanoic acid ester (42) (the ratio of β form:α form was difficult to determine from the results of $^1$H-NMR analysis; 28.9 mg, 0.0501 mmol, yield 22%) as a colorless solid.

$^1$H-NMR (400 MHz, methanol-d$_4$) δ: 0.91 (t, 3H, J=7.0 Hz), 1.27-1.40 (m, 4H), 1.60-1.68 (m, 2H), 2.37 (t, 2H, J=7.4 Hz), 3.26-3.36 (m, 1H), 3.47 (dd, 1H, J=3.8 Hz, 9.7 Hz), 3.52-3.60 (m, 2H), 3.61-3.79 (m, 5H), 3.82-3.93 (m, 3H), 3.88 (s, 3H), 4.95 (d, 1H, J=7.8 Hz), 5.07 (s, 2H), 5.22 (d, 1H, J=3.8 Hz), 6.93 (dd, 1H, J=2.1 Hz, 8.3 Hz), 7.04 (d, 1H, J=2.1 Hz), 7.16 (d, 1H, J=8.3 Hz). ESIMS (m/z): 598.9 ([M+Na]+), 615.0 ([M+K]+).

Example 26

O-[4-(β-D-maltosyloxy)-3-methoxybenzyl]-8-methylnonanoic acid ester (43)

Compound 42-5 (99.0 mg, 0.207 mmol) was suspended in acetone (4 ml) at room temperature, 8-MNA (364 mg, 2.11 mmol) was mixed therewith at room temperature, and Novozym 435 (52.5 mg) and molecular sieves 3A (102 mg) were added. Acetone (4 ml) was further added, and the reaction mixture was stirred with heating under reflux for 17 hours. Then, the reaction mixture was cooled to room temperature, methanol (10 ml) was added, the enzyme and the molecular sieves were filtered off, and the filtrate was concentrated under reduced pressure. The residue was purified by ODS column chromatography (gradient; water:methanol=70:30→35:65). Since purification was insufficient, the obtained oil was purified by PTLC to give a mixture of β form and α form of O-[4-(β-D-maltosyloxy)-3-methoxybenzyl]-8-methylnonanoic acid ester (43) (as a result of $^1$H-NMR analysis, β form:α form ratio was about 10:1; 8.00 mg, 0.0126 mmol, yield 6%) as a colorless solid.

$^1$H-NMR (400 MHz, methanol-d$_4$) δ: 0.89 (d, 6H, J=6.5 Hz), 1.15-1.23 (m, 2H), 1.28-1.39 (m, 6H), 1.48-1.58 (m, 1H), 1.59-1.67 (m, 2H), 2.37 (t, 2H, J=7.3 Hz), 3.29-3.36 (m, 1H), 3.47 (dd, 1H, J=3.8 Hz, 9.7 Hz), 3.52-3.59 (m, 2H), 3.60-3.78 (m, 5H), 3.82-3.93 (m, 3H), 3.88 (s, 3H), 4.95 (d, 1H, J=7.8 Hz), 5.07 (s, 2H), 5.22 (d, 1H, J=3.7 Hz), 6.93 (dd, 1H, J=2.1 Hz, 8.3 Hz), 7.04 (d, 1H, J=2.1 Hz), 7.16 (d, 1H, J=8.3 Hz). ESIMS (m/z): 655.1 ([M+Na]+), 671.0 ([M+K]+).

Example 27

O-3-[4-(β-D-glucopyranosyl-(1→4)-β-D-glucopyranosyloxy)-3-methoxyphenyl]-2-propenyl-8-methylnonanoic acid ester (44)

Compound 44-1 (615 mg, 3.41 mmol) was dissolved in ethyl acetate (12 ml) at room temperature, Novozym 435 (185 mg) was added, and the mixture was heated under reflux for 19 hours. Since the remainder of the starting material was confirmed by thin layer chromatography (TLC), Novozym 435 (90.3 mg) and ethyl acetate (10 ml) were added, and the mixture was further heated under reflux for 6 hours. Then, the reaction mixture was cooled to room temperature, Novozym 435 was filtered off, and the filtrate was concentrated under reduced pressure. The residue was purified by silica gel column chromatography (gradient; ethyl acetate:n-hexane=25:75→45:55) to give compound 44-2 (733 mg, 3.30 mmol, yield 97%) as a colorless solid.

$^1$H-NMR (400 MHz, CDCl$_3$) δ: 2.10 (s, 3H), 3.91 (s, 3H), 1.44-1.58 (m, 1H), 4.71 (dd, 2H, J=1.3 Hz, 6.6 Hz), 6.14 (ddd, 1H, J=15.8 Hz, 6.6 Hz, 6.6 Hz), 6.58 (d, 1H, J=15.8 Hz), 6.85-6.92 (m, 3H).

Then, under an argon atmosphere, D-cellobiose 2,2',3,3',4',6,6'-heptaacetate (10) (1.31 g, 2.05 mmol) was dissolved in a mixed solvent of tetrahydrofuran (5.5 ml) and toluene (5.5 ml) at room temperature, and triphenylphosphine (544 mg, 2.07 mmol) and compound 44-2 (351 mg, 1.58 mmol) were added. The reaction mixture was cooled in an ice bath, diethyl azodicarboxylate 2.2 M toluene solution (0.93 ml, 2.05 mmol) was added dropwise, the ice bath was removed and the mixture was warmed to room temperature and stirred for 6 hours. The reaction solution was concentrated under reduced pressure, the insoluble material was filtered off, and the filtrate was concentrated under reduced pressure. The residue was purified by silica gel column chromatography (gradient; ethyl acetate:n-hexane=25:75→80:20) to give a mixture of β form and α form of compound 44-3 (the ratio of β form:α form was difficult to determine from the results of $^1$H-NMR analysis; 660 mg, 0.785 mmol, yield 50%) as a colorless solid.

$^1$H-NMR (400 MHz, CDCl$_3$) δ: 1.98 (s, 3H), 2.01 (s, 3H), 2.03 (s, 3H), 2.05 (s, 3H), 2.07 (s, 3H), 2.09 (s, 3H), 2.10 (s, 3H), 2.11 (s, 3H), 3.41-3.64 (m, 2H), 3.82 (s, 3H), 3.82-3.88 (m, 1H), 4.06 (dd, 1H, J=2.1 Hz, 12.4 Hz), 4.11-4.14 (m, 1H), 4.38 (dd, 1H, J=4.6 Hz, 12.4 Hz), 4.51-4.56 (m, 2H), 4.71 (dd, 2H, J=1.0 Hz, 6.5 Hz), 4.90-4.96 (m, 2H), 5.07 (dd, 1H, J=9.7

Hz, 9.7 Hz), 5.13-5.28 (m, 3H), 6.19 (ddd, 1H, J=15.8 Hz, 6.5 Hz, 6.5 Hz), 6.58 (d, 1H, J=15.8 Hz), 6.87 (dd, 1H, J=1.9 Hz, 8.3 Hz), 6.92 (d, 1H, J=1.9 Hz), 7.02 (d, 1H, J=8.3 Hz). ESIMS (m/z): 862.9 ([M+Na]$^+$), 879.0 ([M+K]$^+$).

Then, a mixture of β form and α form of compound 44-3 (the ratio of β form:α form was difficult to determine; 101 mg, 0.120 mmol) was dissolved in methanol (1 ml) at room temperature, and the mixture was cooled in an ice bath. Sodium methoxide 0.5 M methanol solution (70 µl, 0.035 mmol) was added, the ice bath was removed and the mixture was warmed to room temperature and stirred for 30 minutes. To the reaction solution was added methanol (10 ml) and the mixture was neutralized with a strong acidic cation exchange resin (Amberlite IR120B H AG), the resin was filtered off, and the filtrate was concentrated under reduced pressure to give a mixture of β form and α form of compound 44-4 (the ratio of β form:α form was difficult to determine from the results of $^1$H-NMR analysis; 58.2 mg, 0.115 mmol, yield 96%) as a pale-yellow solid.

$^1$H-NMR (400 MHz, methanol-d$_4$) δ: 3.19-3.37 (m, 3H), 3.51-3.76 (m, 6H), 3.90 (s, 3H), 3.86-3.95 (m, 3H), 4.23 (dd, 2H, J=1.5 Hz, 5.9 Hz), 4.46 (d, 1H, J=7.9 Hz), 4.95 (d, 1H, J=7.5 Hz), 6.30 (ddd, 1H, J=16.0 Hz, 5.9 Hz, 5.9 Hz), 6.57 (d, 1H, J=16.0 Hz), 6.96 (dd, 1H, J=2.0 Hz, 8.4 Hz), 7.09-7.12 (m, 2H). ESIMS (m/z): 527.0 ([M+Na]$^+$).

Then, a mixture of β form and α form of compound 44-4 (the ratio of β form:α form was difficult to determine; 58.2 mg, 0.115 mmol) was suspended in acetone (2 ml) at room temperature, the suspension was mixed with 8-MNA (197 mg, 1.24 mmol) at room temperature, and Novozym 435 (30.7 mg) and molecular sieves 3A (50 mg) were added. Acetone (2 ml) was further added, and the reaction mixture was heated under reflux for 15 hours. Then, the reaction mixture was cooled to room temperature, Novozym 435 and the molecular sieves were filtered off, and the solid was washed with methanol (10 ml). Then, the combined filtrate was concentrated under reduced pressure, and the residue was purified by ODS column chromatography (gradient; water:methanol=70:30→20:80). Since purification was insufficient, hexane (2 ml) was added to the obtained oil to allow partial solidification, which was followed by filtration. The obtained solid was purified by ODS column chromatography (gradient; water:methanol=100:0→20:80) to give β form of O-3-[4-(β-D-glucopyranosyl-(1→4)-β-D-glucopyranosyloxy)-3-methoxyphenyl]-2-propenyl-8-methylnonanoic acid ester (44) (13.0 mg, 0.0210 mmol, yield 18%) as a colorless solid.

$^1$H-NMR (400 MHz, methanol-d$_4$) δ: 0.89 (d, 6H, J=6.7 Hz), 1.15-1.25 (m, 2H), 1.26-1.41 (m, 6H), 1.48-1.57 (m, 1H), 1.61-1.69 (m, 2H), 2.38 (t, 2H, J=7.5 Hz), 3.24-3.42 (m, 4H), 3.54-3.75 (m, 5H), 3.88-3.995 (m, 3H), 3.89 (s, 3H), 4.46 (d, 1H, J=7.8 Hz), 4.72-4.74 (dd, 2H, J=0.6 Hz, 6.4 Hz), 4.96 (d, 1H, J=7.6 Hz), 6.27 (ddd, 1H, J=15.9 Hz, 6.4 Hz, 6.4 Hz), 6.64 (d, 1H, J=15.9 Hz), 6.98 (dd, 1H, J=1.9 Hz, 8.3 Hz), 7.00-7.13 (m, 2H). ESIMS (m/z): 681.0 ([M+Na]$^+$), 697.0 ([M+K]$^+$).

Example 28

O-[4-(α-L-rhamnosyloxy)-3-methoxybenzyl]-n-hexanoic acid ester (45)

L-rhamnose monohydrate (45-1) (5.00 g, 27.5 mmol) was dissolved in pyridine (31 ml) at room temperature, and the mixture was cooled in an ice bath. Acetic anhydride (15.5 ml, 164 mmol) was added, and the reaction mixture was warmed to room temperature and stirred for 13 ours. The reaction mixture was cooled in an ice bath, water (50 ml) was slowly added, the ice bath was removed and the mixture was extracted 3 times with ethyl acetate (50 ml) at room temperature. The combined organic layer was washed twice with 3 N HCl (50 ml), then with water (50 ml), saturated aqueous sodium hydrogen carbonate solution (50 ml), and 15% brine (50 ml). The organic layer was dried over anhydrous magnesium sulfate, the solid was filtered off, and the filtrate was concentrated under reduced pressure. The residue was purified by silica gel column chromatography (gradient; ethyl acetate:n-hexane=5:95→30:70) to give a mixture of α form and β form of compound 45-2 (the ratio of β form:α form was difficult to determine from the results of $^1$H-NMR analysis; 9.07 g, 27.3 mmol, yield 99%) as a colorless oil.

$^1$H-NMR (400 MHz, CDCl$_3$) δ: 1.24 (d, 3H, J=6.2 Hz), 2.01 (s, 3H), 2.06 (s, 3H), 2.16 (s, 3H), 2.17 (s, 3H), 3.94 (ddd, 1H, J=0.5 Hz, 6.2 Hz, 10.0 Hz), 5.18-5.15 (m, 1H), 5.25 (dd, 1H, J=1.8 Hz, 3.5 Hz), 5.31 (dd, 1H, J=3.5 Hz, 10.0 Hz), 6.02 (d, 1H, J=1.8 Hz). ESIMS (m/z): 355.0 ([M+Na]$^+$), 370.9 ([M+K]$^+$).

Then, a mixture of β form and α form of compound 45-2 (the ratio of β form:α form was difficult to determine; 2.59 g, 7.79 mmol) was dissolved in N,N-dimethylformamide (10 ml) at room temperature, and cooled in an ice bath. To this solution was added ammonium acetate (1.50 g, 19.4 mmol), and the ice bath was removed. The mixture was stirred at room temperature for 23 hours. The reaction container was cooled in an ice bath, water (50 ml) was added slowly, the ice bath was removed, and the mixture was extracted 5 times with ethyl acetate (30 ml) at room temperature. The combined organic layer was washed with 15% brine (30 ml), dried over anhydrous magnesium sulfate, and filtered, and the filtrate was concentrated under reduced pressure. The residue was purified by silica gel column chromatography (gradient; ethyl acetate:n-hexane=5:95→50:50) to give a mixture of α form and β form of compound 45-3 (the ratio of β form:α form was difficult to determine from the results of $^1$H-NMR analysis; 1.22 g, 4.20 mmol, yield 54%) as a colorless solid.

$^1$H-NMR (400 MHz, CDCl$_3$) δ: 1.23 (d, 3H, J=6.4 Hz), 2.00 (s, 3H), 2.06 (s, 3H), 2.20 (s, 3H), 2.81 (d, 1H, J=3.9 Hz), 4.08-4.17 (m, 1H), 5.17 (dd, 1H, J=1.9 Hz, 3.9 Hz), 5.28 (dd, 1H, J=1.9 Hz, 3.5 Hz), 5.38 (dd, 1H, J=3.5 Hz, 10.2 Hz). ESIMS (m/z): 12.9 ([M+Na]$^+$), 328.9 ([M+K]$^+$).

Then, under an argon atmosphere, a mixture of β form and α form of compound 45-3 (the ratio of β form:α form was difficult to determine; 399 mg, 1.37 mmol) was dissolved in a mixed solvent of tetrahydrofuran (1 ml) and toluene (6 ml) at room temperature, and triphenylphosphine (364 mg, 1.39 mmol) and compound 6 (208 mg, 1.06 mmol) were added. The reaction mixture was cooled in an ice bath, diethyl azodicarboxylate 2.2 M toluene solution (0.63 ml, 1.39 mmol) was added dropwise, the ice bath was removed and the mixture was warmed to room temperature, and stirred for 3 hours. The reaction solution was concentrated under reduced pressure, the insoluble material was filtered off, and the filtrate was concentrated under reduced pressure. The residue was purified by silica gel column chromatography (gradient; ethyl acetate:n-hexane=32:68→47:53) to give a mixture of α form and β form of compound 45-4 (as a result of $^1$H-NMR analysis, α form:β form ratio was about 11:1; 451 mg, 0.962 mmol, yield 91%) as a colorless solid.

$^1$H-NMR (400 MHz, CDCl$_3$) δ: 1.29 (d, 3H, J=7.1 Hz), 2.01 (s, 3H), 2.06 (s, 3H), 2.10 (s, 3H), 2.28 (s, 3H), 3.54 (dd, 1H, J=6.2 Hz, 9.2 Hz), 3.83 (s, 3H), 5.04 (s, 2H), 5.04-5.13 (m, 3H), 5.71 (dd, 1H, J=1.1 Hz, 3.2 Hz), 6.87 (dd, 1H, J=2.0 Hz, 8.2 Hz), 6.90 (d, 1H, J=2.0 Hz), 7.05 (d, 1H, J=8.1 Hz). ESIMS (m/z): 490.9 ([M+Na]$^+$), 506.7 ([M+K]$^+$).

Then, a mixture of β form and α form of compound 45-4 (β form:α form ratio was about 11:1; 365 mg, 0.779 mmol) was dissolved in methanol (3 ml) at room temperature, and the mixture was cooled in an ice bath. Sodium methoxide 0.5 M methanol solution (467 μl, 0.23 mmol) was added, the ice bath was removed and the mixture was warmed to room temperature and stirred for 2 hours. The reaction mixture was cooled in an ice bath, sodium methoxide 0.5 M methanol solution (312 μl, 0.16 mmol) was added, the ice bath was removed and the mixture was warmed to room temperature and stirred for 30 minutes. The reaction solution was neutralized with a strong acidic cation exchange resin (Amberlite IR120B H AG), the resin was filtered off, and the filtrate was concentrated under reduced pressure to give a mixture of α form and β form of compound 45-5 (as a result of $^1$H-NMR analysis, α form:β form ratio was about 11:1; 230 mg, 0.767 mmol, yield 98%) as a colorless solid.

$^1$H-NMR (400 MHz, methanol-$d_4$) δ: 1.33 (d, 3H, J=6.0 Hz), 3.34-3.45 (m, 2H), 3.50 (dd, 1H, J=3.2, 9.3 Hz), 3.89 (s, 3H), 4.12 (dd, 1H, J=0.9 Hz, 3.2 Hz), 4.57 (s, 2H), 5.06 (d, 1H, J=0.9 Hz), 6.89 (dd, 1H, J=1.9 Hz, 8.3 Hz), 7.05 (d, 1H, J=1.9 Hz), 7.09 (d, 1H, J=8.3 Hz). ESIMS (m/z): 323.0 ([M+Na]$^+$), 338.9 ([M+K]$^+$).

Then, compound 45-5 (102 mg, 0.341 mmol) was suspended in acetone (5 ml) at room temperature, the suspension was mixed with n-hexanoic acid (428 μl, 3.41 mmol) at room temperature, and Novozym 435 (49.9 mg) and molecular sieves 3A (101 mg) were added. Acetone (5 ml) was further added, and the reaction mixture was stirred with heating under reflux for 16 hours. Then, the reaction mixture was cooled to room temperature, methanol (10 ml) was added, Novozym 435 and the molecular sieves were filtered off, and the filtrate was concentrated under reduced pressure. The residue was purified by ODS column chromatography (gradient; water:methanol=70:30→30:70) to give a mixture of α form and β form of O-[4-(α-L-rhamnosyloxy)-3-methoxybenzyl]-n-hexanoic acid ester (45) (as a result of $^1$H-NMR analysis, α form:β form ratio was about 13:1; 62.6 mg, 0.137 mmol, yield 41%) as a colorless solid.

$^1$H-NMR (400 MHz, methanol-$d_4$) δ: 0.91 (t, 3H, J=6.7 Hz), 1.27-1.39 (m, 4H), 1.34 (d, 3H, J=6.2 Hz), 1.59-1.68 (m, 2H), 2.37 (t, 2H, J=7.4 Hz), 3.35-3.46 (m, 2H), 3.51 (dd, 1H, J=3.2 Hz, 9.0 Hz), 3.88 (s, 3H), 4.12 (brd, 1H, J=2.7 Hz), 5.08 (s, 2H), 5.09 (brs, 1H), 6.92 (dd, 1H, J=1.9 Hz, 8.2 Hz), 7.04 (d, 1H, J=1.9 Hz), 7.10 (d, 1H, J=8.2 Hz). ESIMS (m/z): 420.9 ([M+Na]$^+$), 436.9 ([M+K]$^+$).

Example 29

O-[4-(α-L-rhamnosyloxy)-3-methoxybenzyl]-8-methylnonanoic acid ester (46)

Compound 45-5 (100 mg, 0.334 mmol) was suspended in acetone (5 ml) at room temperature, 8-MNA (572 mg, 3.32 mmol) was added at room temperature, and Novozym 435 (50.4 mg) and molecular sieves 3A (99.5 mg) were added. Acetone (5 ml) was further added, the reaction mixture was stirred with heating under reflux for 16 hours. Then, the reaction mixture was cooled to room temperature, methanol (10 ml) was added, Novozym 435 and the molecular sieves were filtered off, and the filtrate was concentrated under reduced pressure. To the obtained oil was added hexane (20 ml) at −78° C., the mixture was warmed to room temperature and the solid was collected by filtration. The solid was purified by ODS column chromatography (gradient; water:methanol=70:30→10:90) to give a form of O-[4-(α-L-rhamnosyloxy)-3-methoxybenzyl]-8-methylnonanoic acid ester (46) (62.6 mg, 0.137 mmol, yield 41%) as a colorless solid.

$^1$H-NMR (400 MHz, methanol-$d_4$) δ: 0.89 (d, 6H, J=6.7 Hz), 1.15-1.23 (m, 2H), 1.28-1.39 (m, 6H), 1.34 (d, 3H, J=5.9 Hz), 1.50-1.57 (m, 1H), 1.59-1.67 (m, 2H), 2.37 (t, 2H, J=7.3 Hz), 3.35-3.44 (m, 2H), 3.51 (dd, 1H, J=3.2 Hz, 9.1 Hz), 3.89 (s, 3H), 4.12 (dd, 1H, J=1.0 Hz, 3.2 Hz), 5.08 (s, 2H), 5.09 (d, 1H, J=1.0 Hz), 6.93 (dd, 1H, J=2.1 Hz, 8.2 Hz), 7.05 (d, 1H, J=2.1 Hz), 7.10 (d, 1H, J=8.2 Hz). ESIMS (m/z): 477.0 ([M+Na]$^+$), 492.8 ([M+K]$^+$).

Comparative Example 3

N-[4-(β-D-glucopyranosyloxy)-3-methoxybenzyl]-8-methylnonanamide (47)

Under an argon atmosphere, compound 2 (159 mg, 0.458 mmol) was dissolved in toluene (2.0 ml) at room temperature, and triphenylphosphine (118 mg, 0.347 mmol) and compound 27-2 (99.8 mg, 0.450 mmol) were added. The reaction mixture was cooled in an ice bath, and diethyl azodicarboxylate 2.2 M toluene solution (0.21 ml, 0.462 mmol) was added dropwise. The ice bath was removed and the mixture was warmed to room temperature and stirred for 3 hours. The reaction solution was concentrated under reduced pressure, the insoluble material was filtered off, and the filtrate was concentrated under reduced pressure. The residue was purified by silica gel column chromatography (gradient; ethyl acetate:n-hexane=27:73→43:57) to give a mixture of β form and α form of compound 47-1 (the ratio of β form:α form was difficult to determine from the results of $^1$H-NMR analysis; 48.1 mg, 0.0779 mmol, yield 22%) as a colorless solid.

$^1$H-NMR (400 MHz, CDCl$_3$) δ: 3.85 (s, 3H), 4.30 (d, 2H, J=5.9 Hz), 8.13 (s, 2H), 5.60 (brs, 1H), 6.75-6.83 (m, 2H), 6.85 (d, 1H, J=8.1 Hz), 7.29-7.37 (m, 5H). ESIMS (m/z): 310.0 ([M+Na]$^+$), 326.0 ([M+K]$^+$).

Then, under an argon atmosphere, a mixture of β form and a form of compound 47-1 (the ratio of β form:α form was difficult to determine; 43.4 mg, 0.0703 mmol) was dissolved in methanol (1 ml) at room temperature. Palladium/carbon (Pd 2%, Pd/C, 21.7 mg) was added, the atmosphere was substituted with hydrogen and the mixture was stirred for 3 hours. Palladium/carbon was filtered off, and the filtrate was concentrated under reduced pressure to give a mixture of β form and α form of compound 47-2 (the ratio of β form:α form was difficult to determine from the results of $^1$H-NMR analysis; 33.7 mg, 0.0697 mmol, yield 99%) as a colorless solid.

$^1$H-NMR (400 MHz, CDCl$_3$) δ: 2.04 (s, 3H), 2.04 (s, 3H), 2.12 (s, 3H), 2.12 (s, 3H), 3.75 (ddd, 1H, J=2.5 Hz, 5.1 Hz, 10.0 Hz), 3.83 (s, 2H), 3.83 (s, 3H), 4.16 (dd, 1H, J=2.5 Hz, 12.2 Hz), 4.28 (dd, 1H, J=5.1 Hz, 12.2 Hz), 4.91-4.94 (m, 1H), 5.14-5.19 (m, 1H), 5.24-5.32 (m, 2H), 6.81 (dd, 1H, J=1.9 Hz, 8.1 Hz), 6.89 (d, 1H, J=1.9 Hz), 7.08 (d, 1H, J=8.1 Hz). ESIMS (m/z): 483.8 ([M+Na]$^+$), 505.8 ([M+K]$^+$), 967.0 ([2 m+H]$^+$), 989.0 ([2 m+Na]$^+$).

Then, a mixture of β form and α form of compound 47-2 (the ratio of β form:α form was difficult to determine; 30.4 mg, 0.0630 mmol) was dissolved in dichloromethane (1.0 ml) at room temperature, and 8-MNA (18.0 mg, 0.104 mmol) was added. The reaction mixture was cooled in an ice bath, and WSC hydrochloride (25.2 mg, 0.131 mmol) was added. The ice bath was removed and the mixture was warmed to room temperature, and stirred for 15 hours. Water (6 ml) was slowly added, the ice bath was removed and the mixture was extracted 3 times with dichloromethane (6 ml) at room temperature. The combined organic layer was washed with 15% brine (5 ml), and dried over anhydrous magnesium sulfate. The solid was filtered off, and the filtrate was concentrated under reduced pressure. To the obtained crude product 47-3 was added methanol (1 ml), and the reaction mixture was cooled in an ice bath. A strong basic anion exchange resin (Amberlite IRA 400 OH AG) was added, the resin was filtered off, and the filtrate was concentrated under reduced pressure. To the residue was added methanol (1.5 ml), and the reaction mixture was cooled in an ice bath. Sodium methoxide 0.5 M methanol solution (36 μl, 0.018 mmol) was added, the ice bath was removed and the mixture was warmed to room temperature and stirred for 30 minutes. The reaction solution was neutralized with a strong acidic cation exchange resin (Amberlite IR120B H AG), the resin was filtered off, and the filtrate was concentrated under reduced pressure. To the obtained residue was added diethyl ether (1 ml), and the mixture was ultrasonicated for 5 minutes. The solid was collected by filtration, and dried to give a mixture of β form and α form of N-[4-(β-D-glucopyranosyloxy)-3-methoxybenzyl]-8-methylnonanamide (47) (the ratio of β form:α form was difficult to determine from the results of $^1$H-NMR analysis; 16.0 mg, 0.0341 mmol, yield from compound 47-2 54%) as a colorless solid.

$^1$H-NMR (400 MHz, methanol-$d_4$) δ: 0.90 (d, 6H, J=6.7 Hz), 1.15-1.23 (m, 2H), 1.27-1.40 (m, 6H), 1.48-1.58 (m, 1H), 1.60-1.69 (m, 2H), 2.24 (t, 2H, J=7.3 Hz), 3.39-3.52 (m, 4H), 3.67-3.73 (m, 1H), 3.87 (s, 3H), 3.86-3.90 (m, 1H), 4.32 (s, 2H), 4.86-4.89 (m, 1H), 6.84 (dd, 1H, J=1.9 Hz, 8.3 Hz), 6.96 (d, 1H, J=1.9 Hz), 7.13 (d, 1H, J=8.3 Hz). ESIMS (m/z): 491.9 ([M+Na]$^+$), 507.9 ([M+K]$^+$).

Experimental Example 1

GLP-1 Secretion

Subcultured human colorectal cancer-derived cell line NCI-H716 (ATCC) was plated on a poly-D-lysine coated 96-well plate at 1×10$^5$ cells per well. After culture at 37° C., 5% $CO_2$ for 48 hours, the medium was substituted with a buffer (146 mM NaCl, 5 mM KCl, 1 mM $MgSO_4$, 5.5 mM Glucose, 20 mM HEPES, 1.5 mM $CaCl_2$, 0.2% BSA, pH 7.4), and dihydrocapsiate (DCT), dihydrocapsiate glycoside and structural analogs thereof (compounds 4, 12, 47, 27, 20, 18, 16, 30, 32, 32-3, 34, 35, 36, 24-2, 33, 14, 22, 23 and 24), each prepared to a given concentration with dimethyl sulfoxide (DMSO), were added. After treatment at 37° C., 5% $CO_2$ for 60 minutes, the supernatant was recovered, and the concentration of GLP-1 in the supernatant was measured by the ELISA method. The strength of the activity of each compound is expressed against GLP-1 concentration of the control group (0.1% DMSO treatment group) as 1, and the compound showing higher GLP-1 concentration than the control group was evaluated as active.

Figure 2:
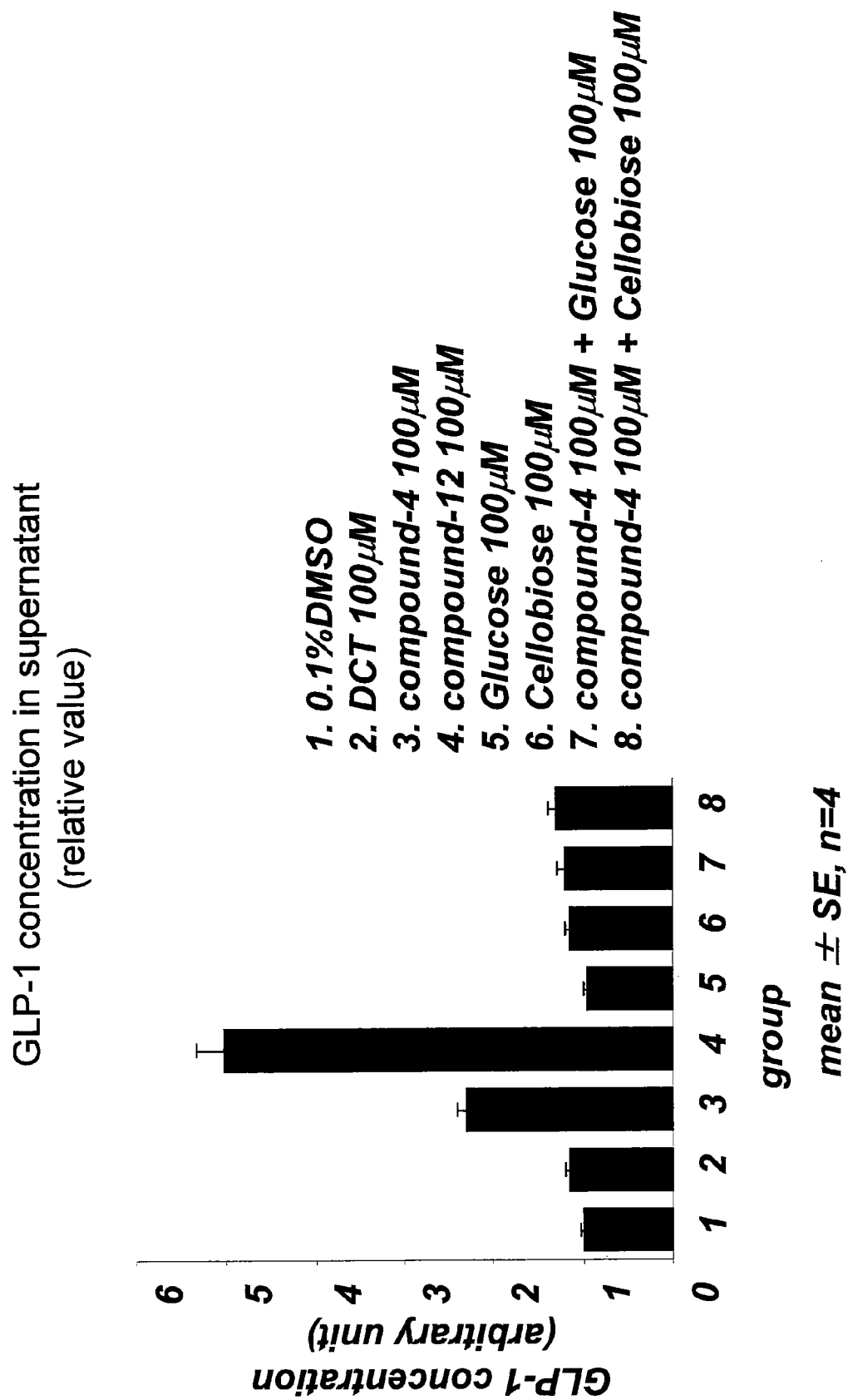
FIG. 2 is a graph showing the measurement results of the GLP-1 concentration in a supernatant in Experimental Example 1.
Figure 3:
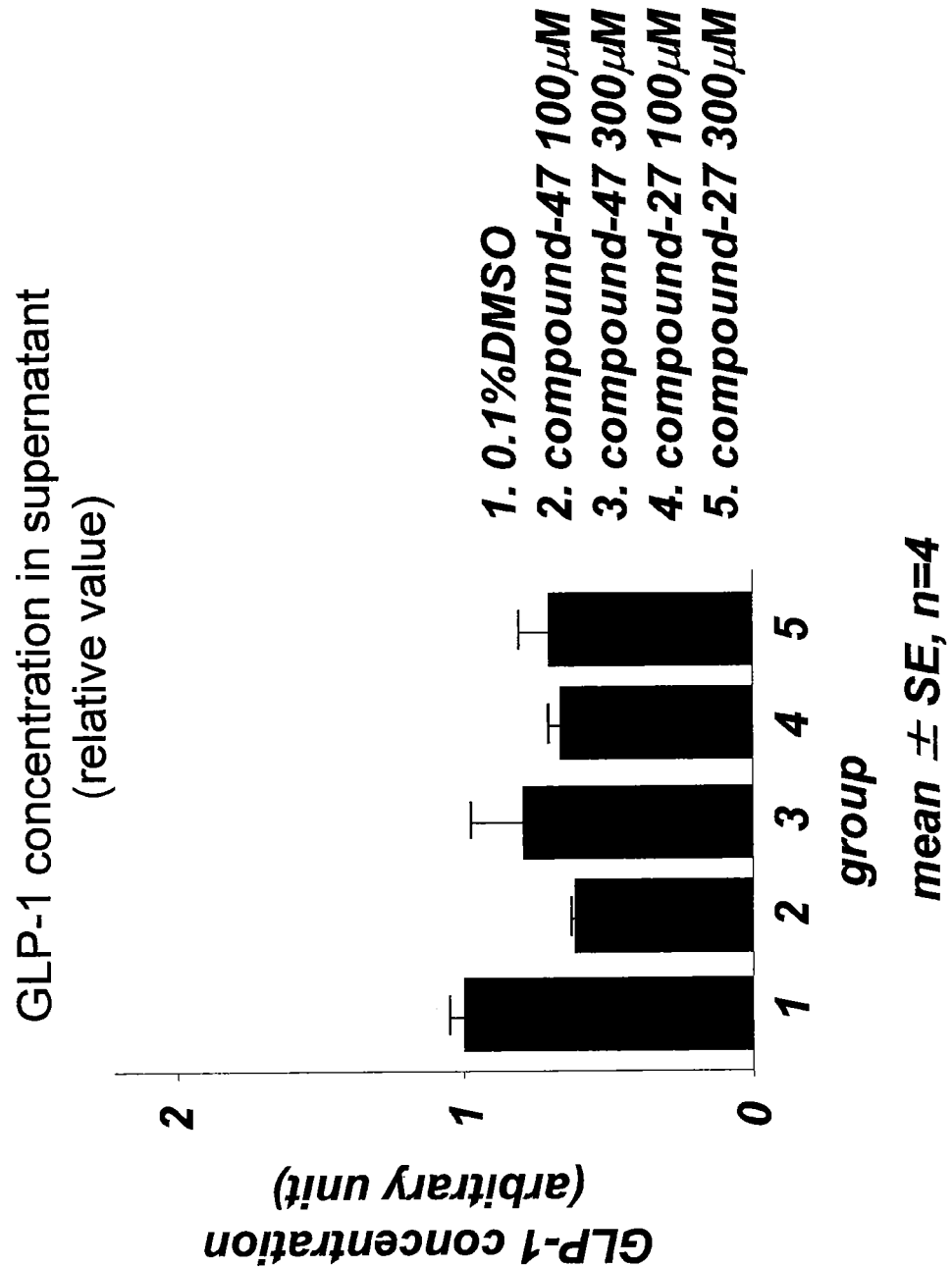
FIG. 3 is a graph showing the measurement results of the GLP-1 concentration in a supernatant in Experimental Example 1.
Figure 4:
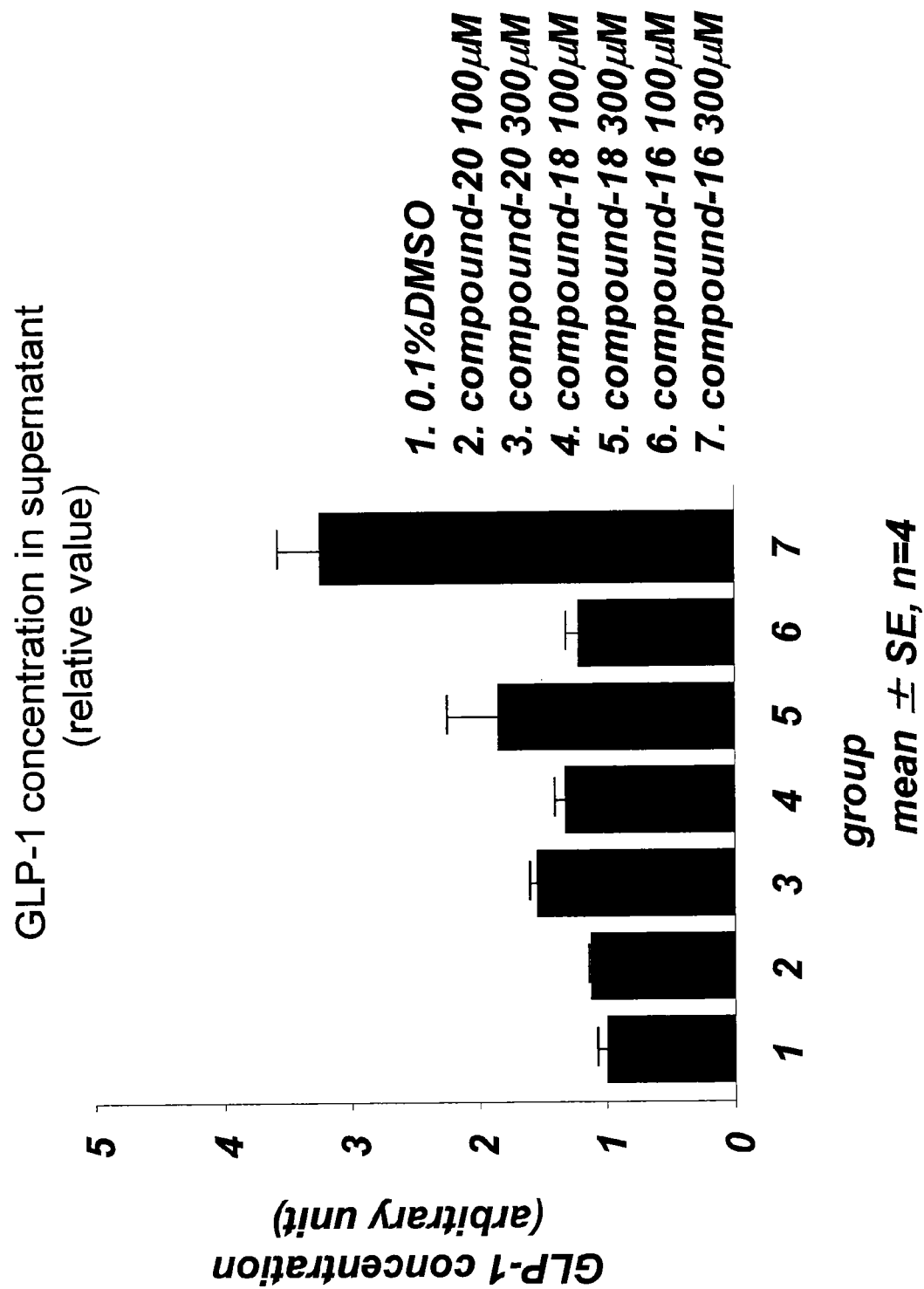
FIG. 4 is a graph showing the measurement results of the GLP-1 concentration in a supernatant in Experimental Example 1.
Figure 5:
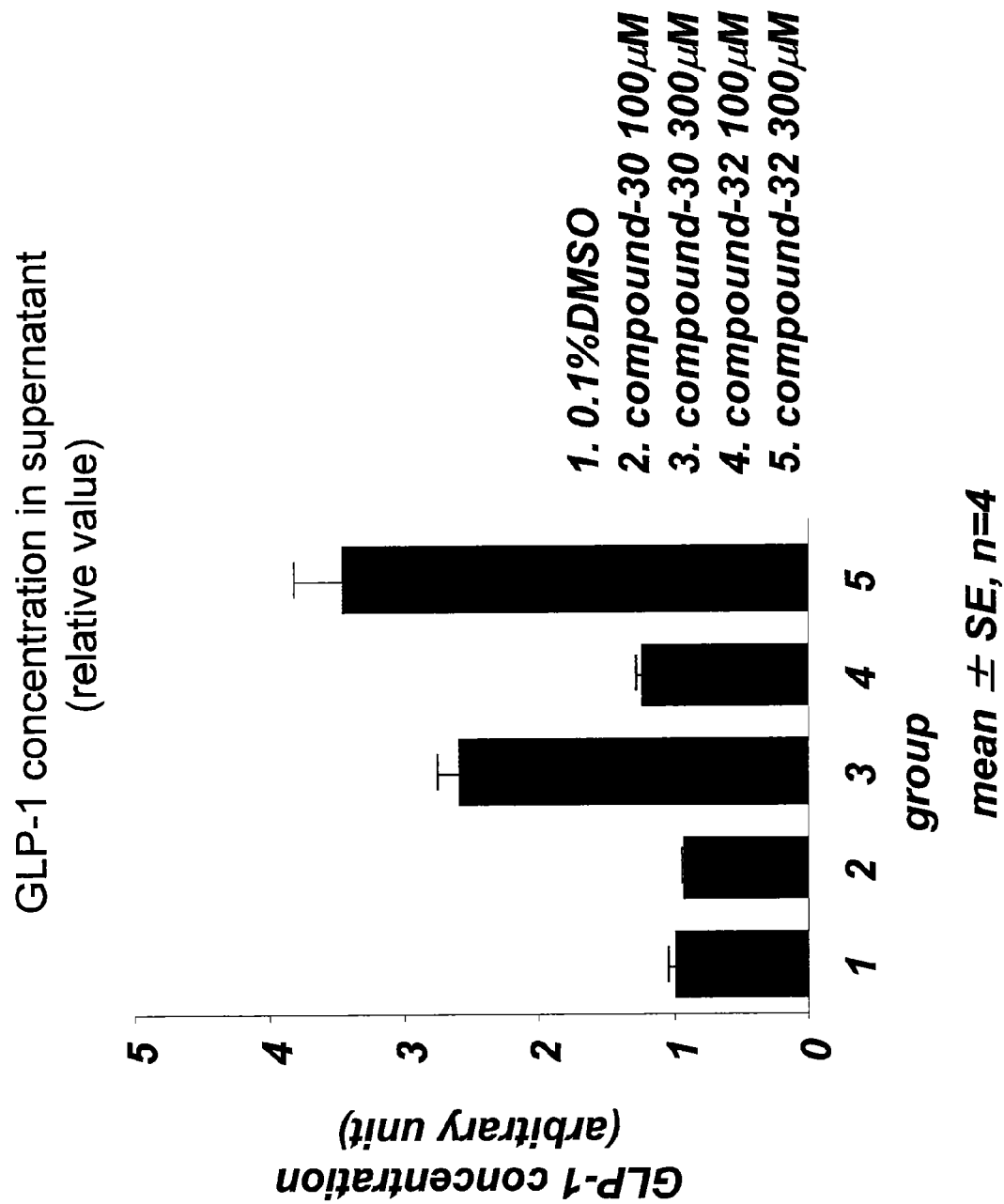
FIG. 5 is a graph showing the measurement results of the GLP-1 concentration in a supernatant in Experimental Example 1.
Figure 6:
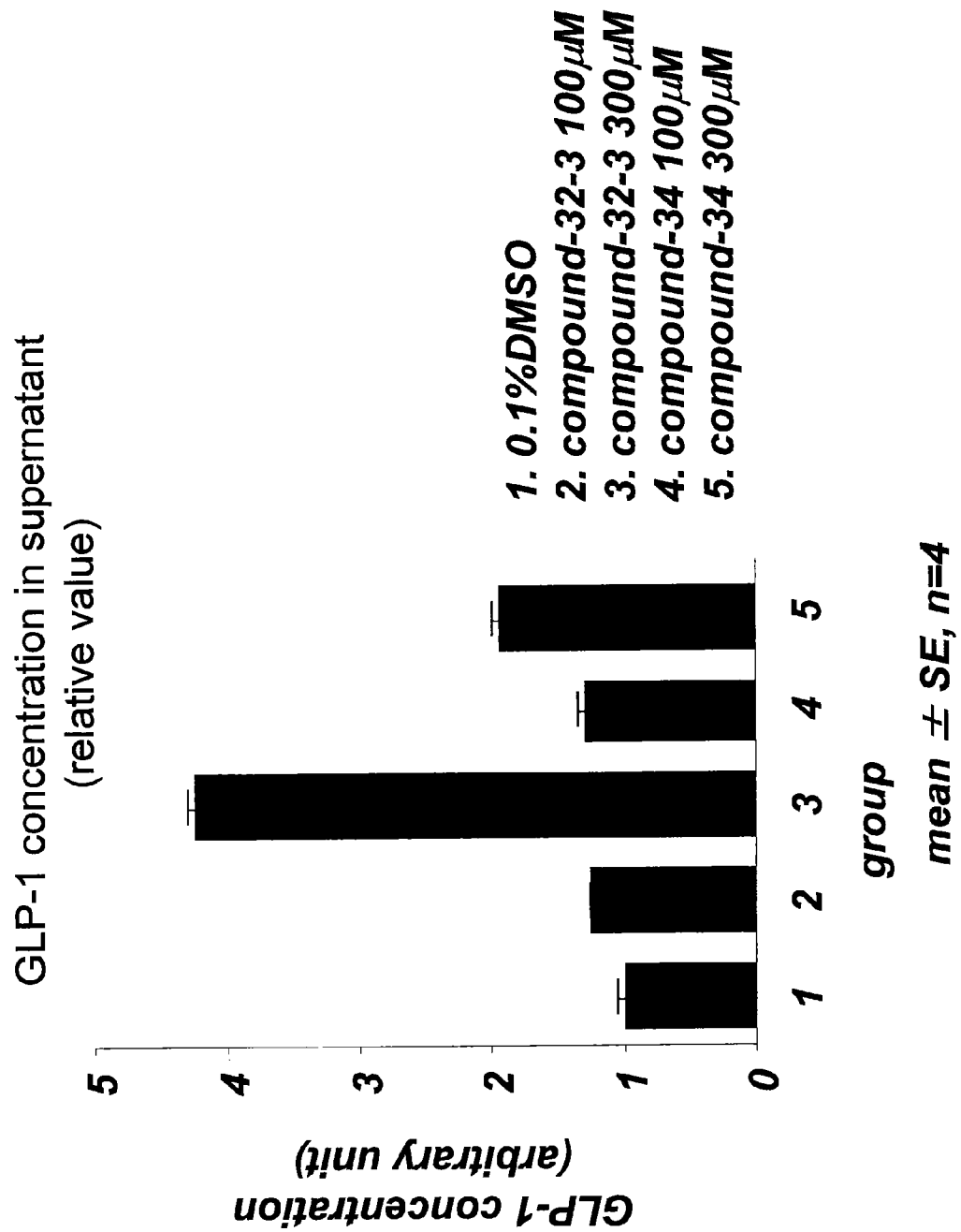
FIG. 6 is a graph showing the measurement results of the GLP-1 concentration in a supernatant in Experimental Example 1.
Figure 7:
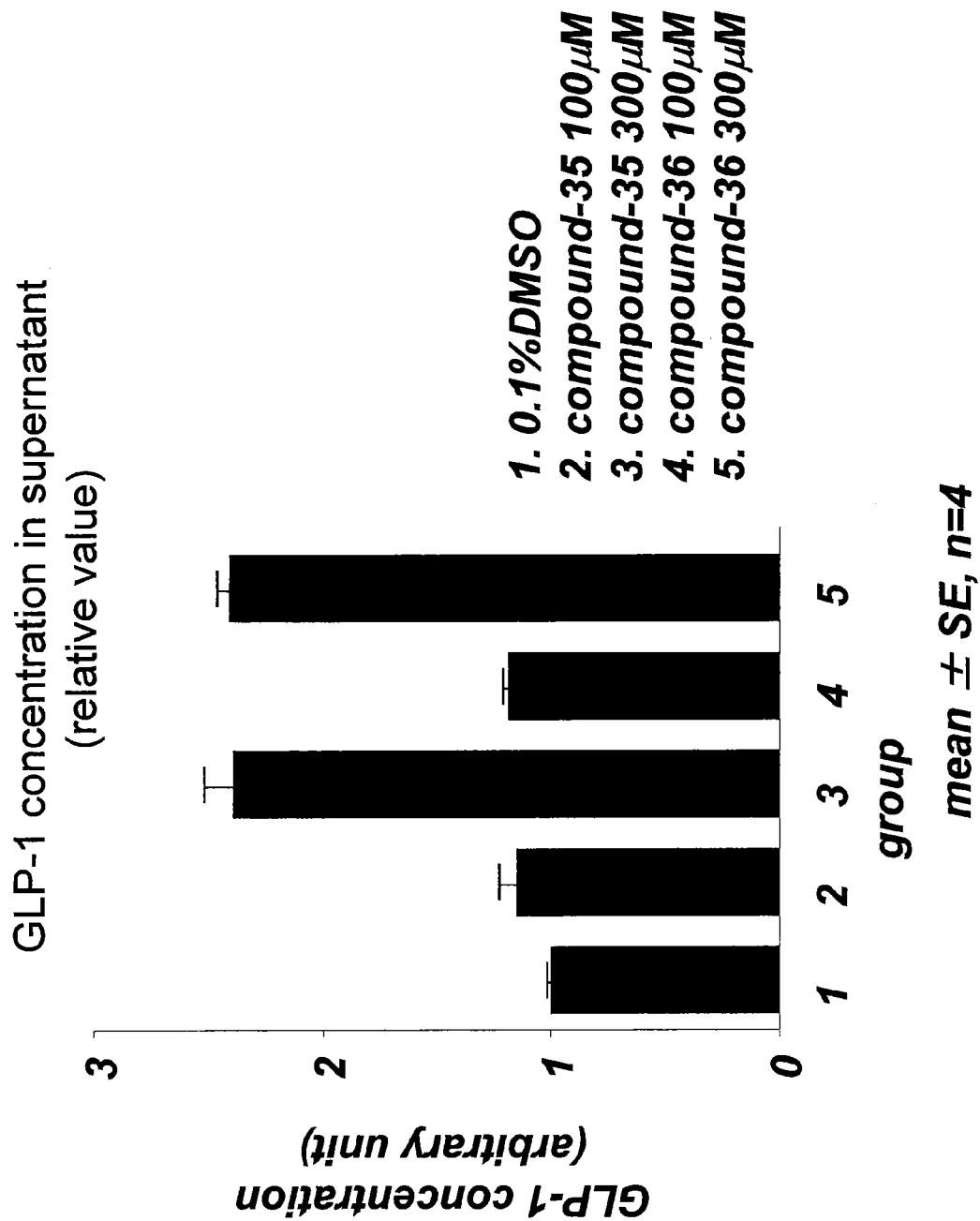
FIG. 7 is a graph showing the measurement results of the GLP-1 concentration in a supernatant in Experimental Example 1.
Figure 8:
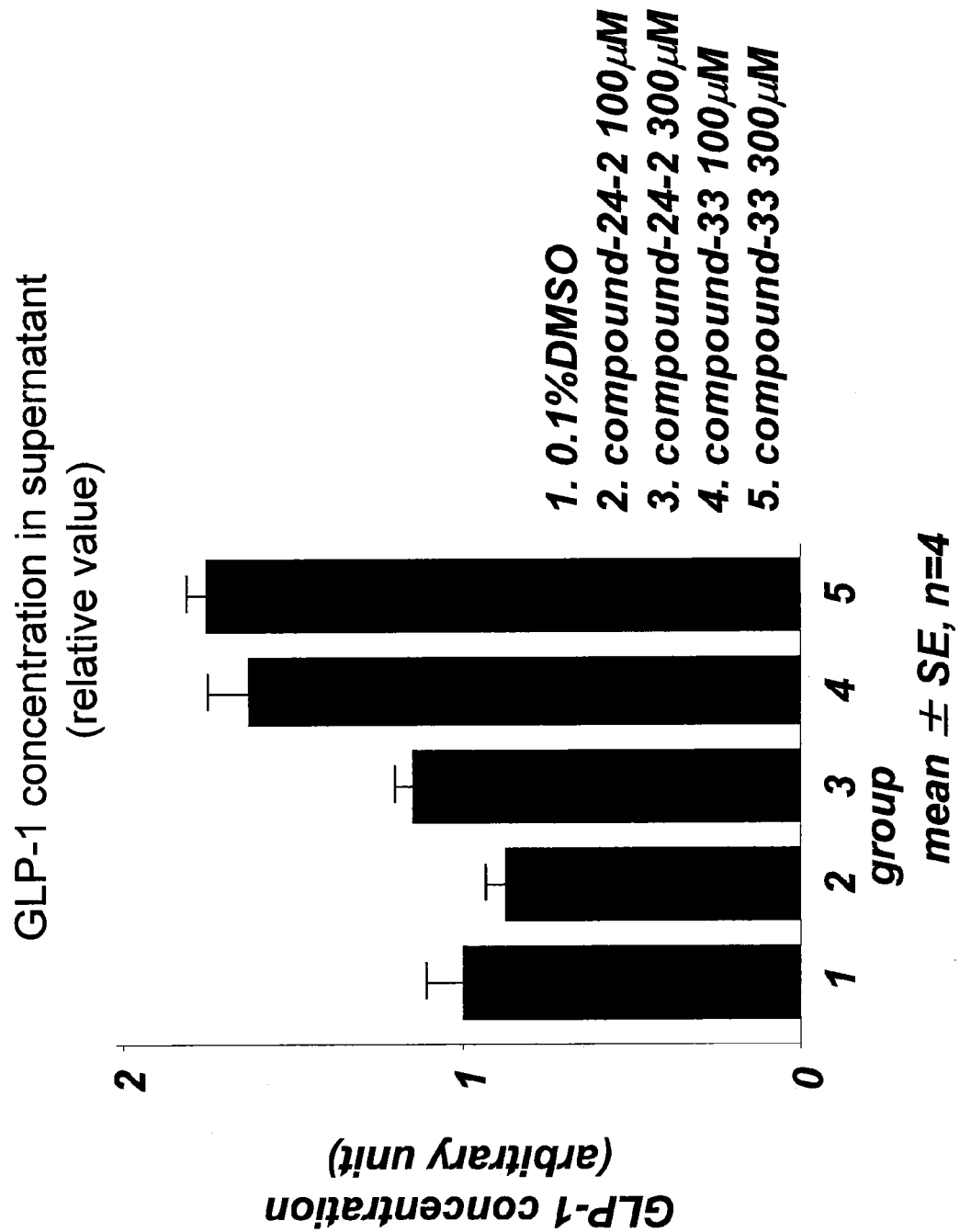
FIG. 8 is a graph showing the measurement results of the GLP-1 concentration in a supernatant in Experimental Example 1.
Figure 9:
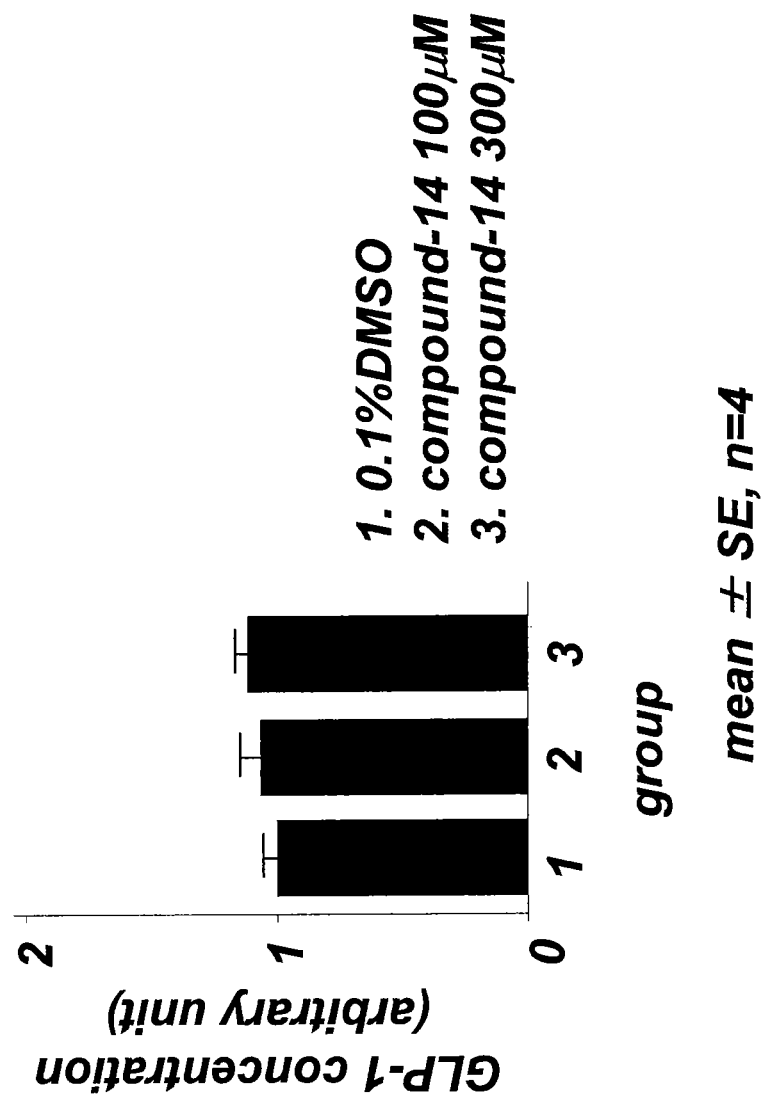
FIG. 9 is a graph showing the measurement results of the GLP-1 concentration in a supernatant in Experimental Example 1.
Figure 10:
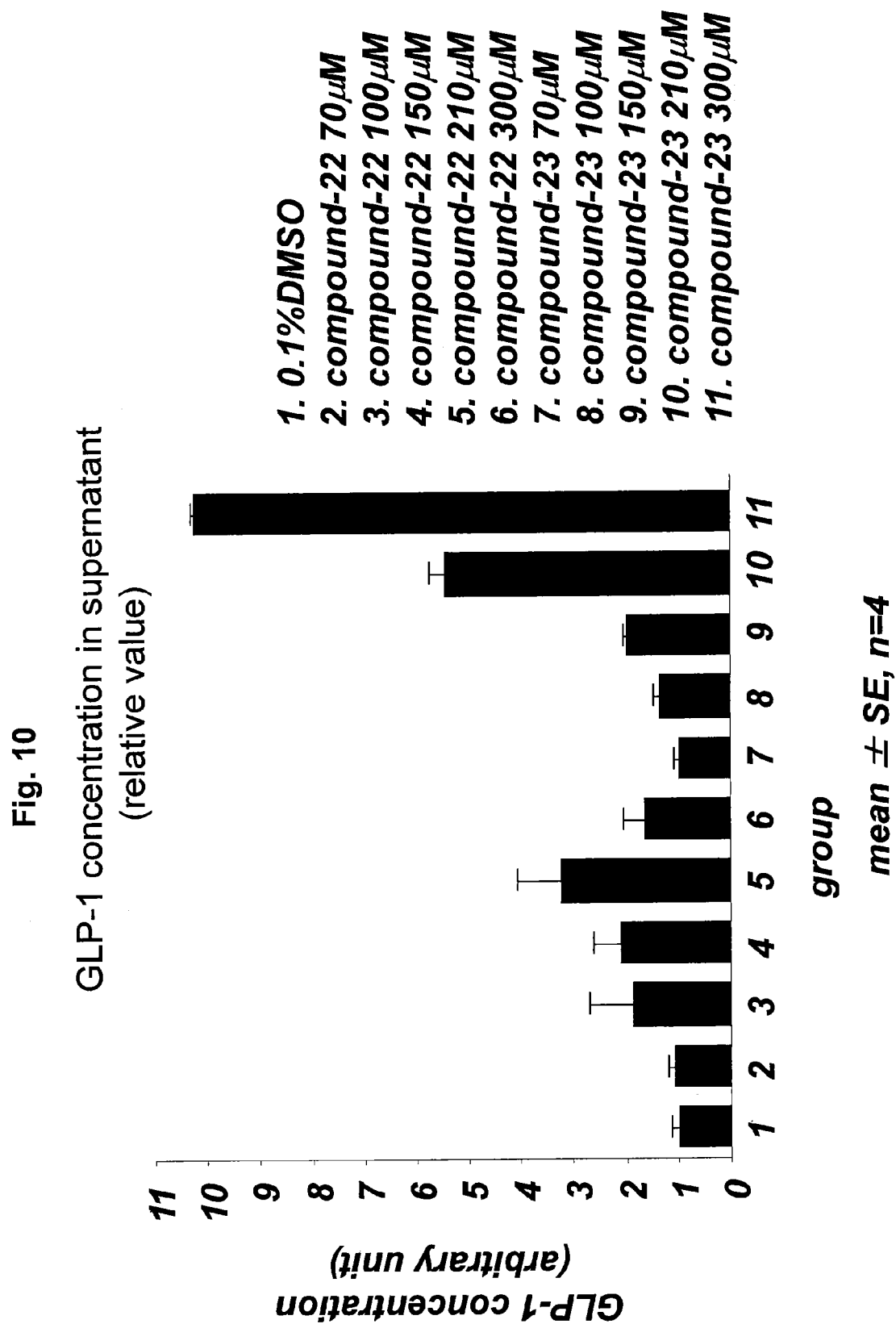
FIG. 10 is a graph showing the measurement results of the GLP-1 concentration in a supernatant in Experimental Example 1.
Figure 11:
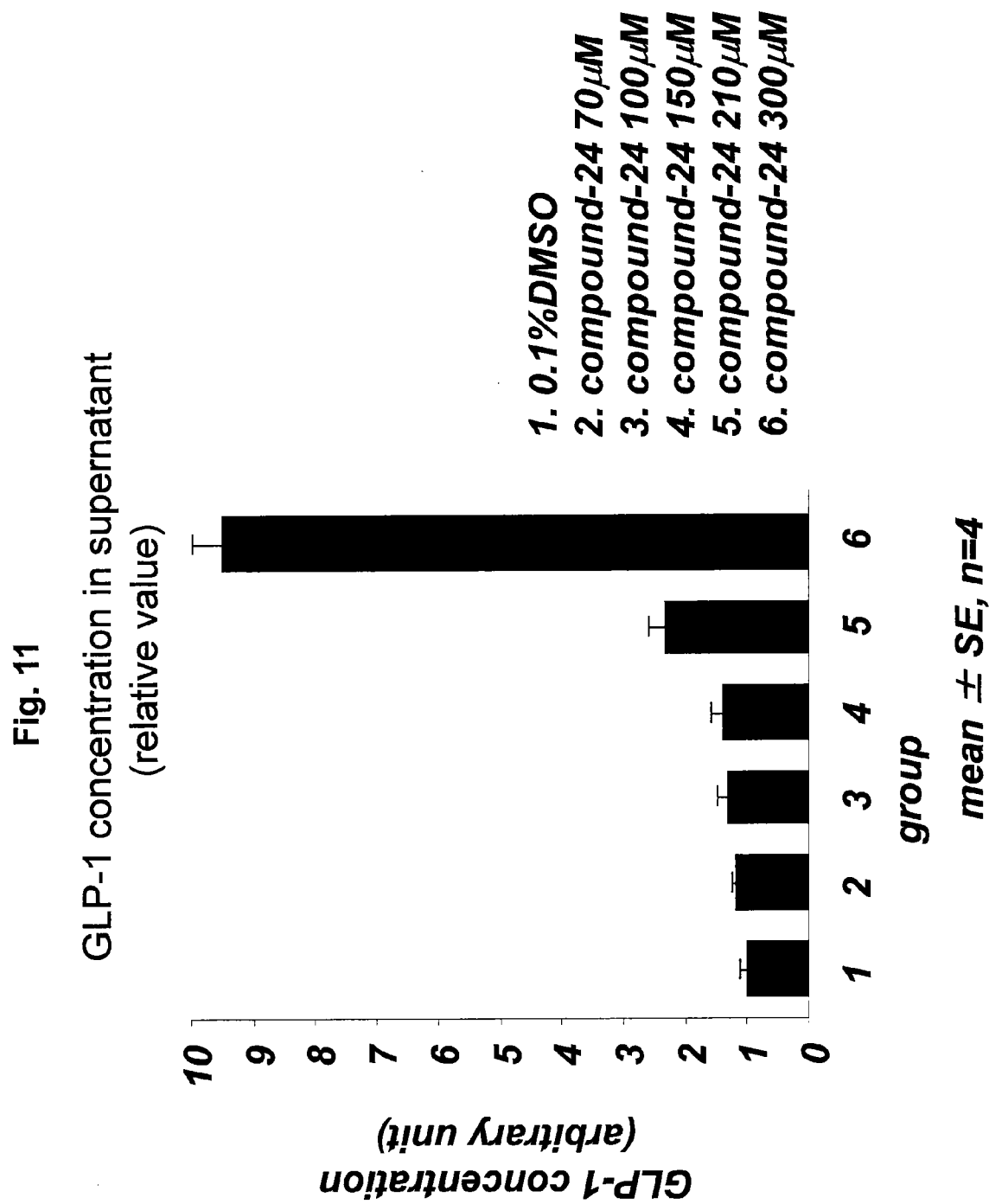
FIG. 11 is a graph showing the measurement results of the GLP-1 concentration in a supernatant in Experimental Example 1.
Figure 12:
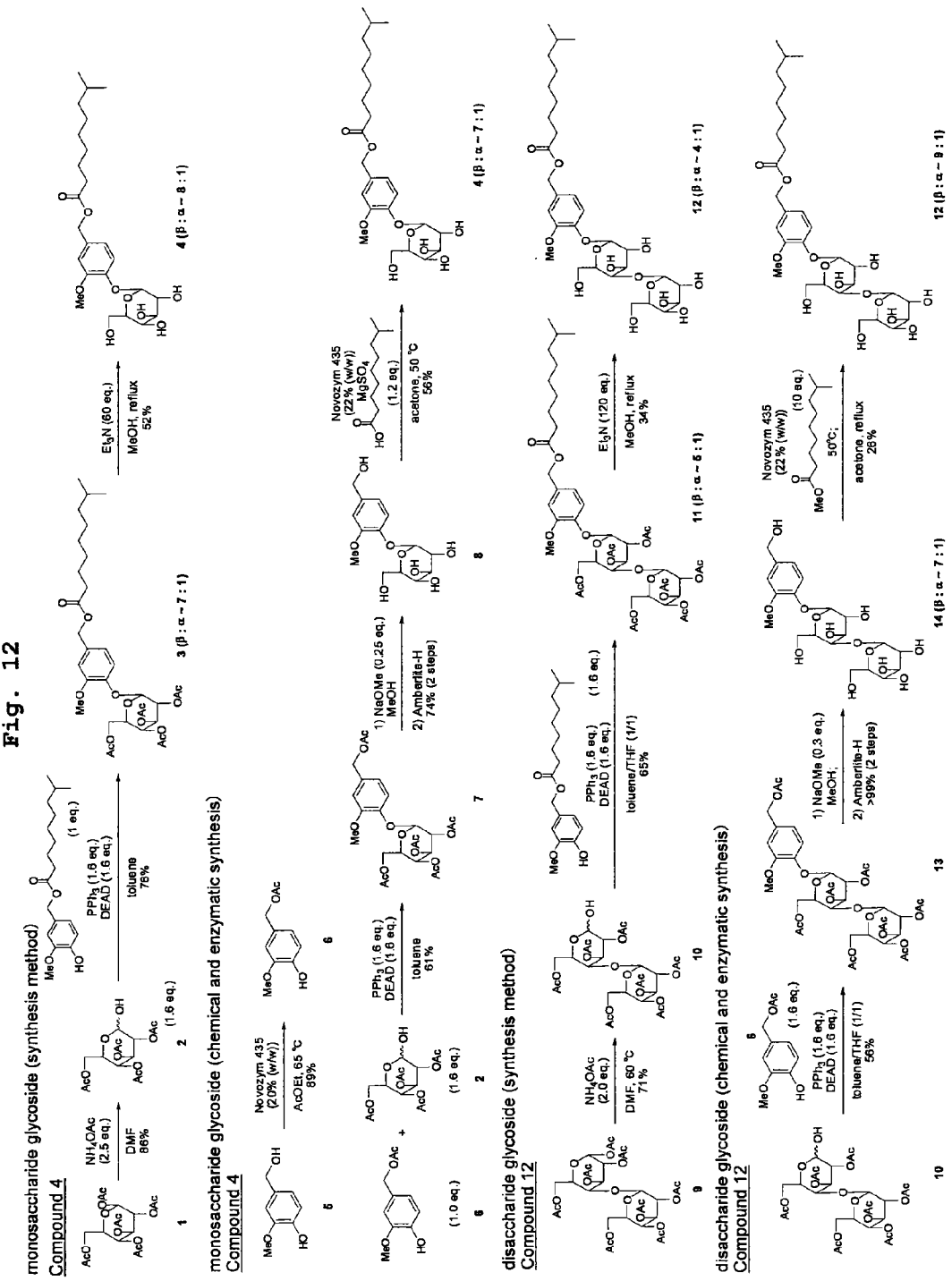
FIG. 12 shows the schemes of Examples 1 to 4.
Figure 14:
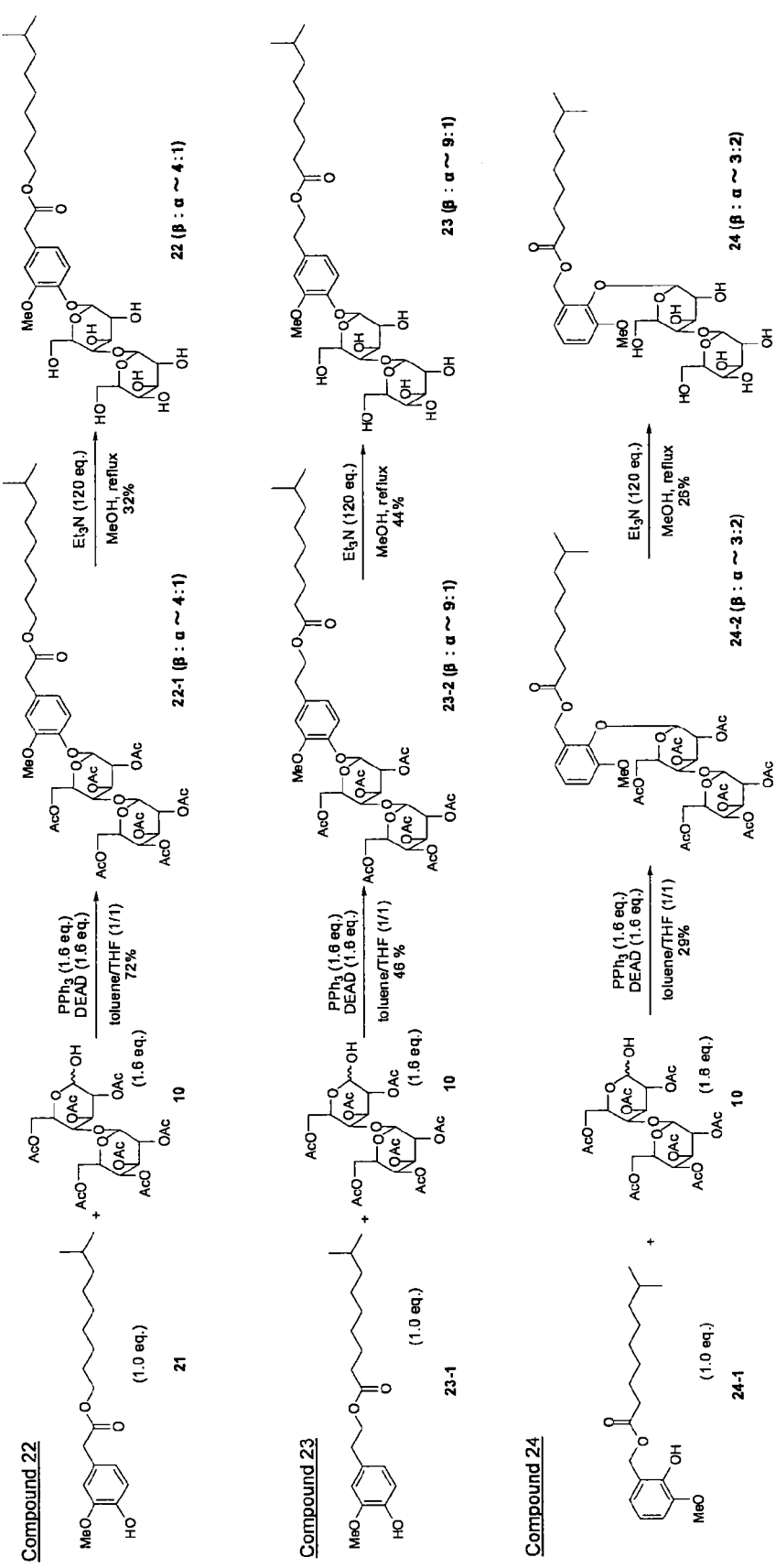
FIG. 14 shows the schemes of Examples 8 to 10.
Figure 15:
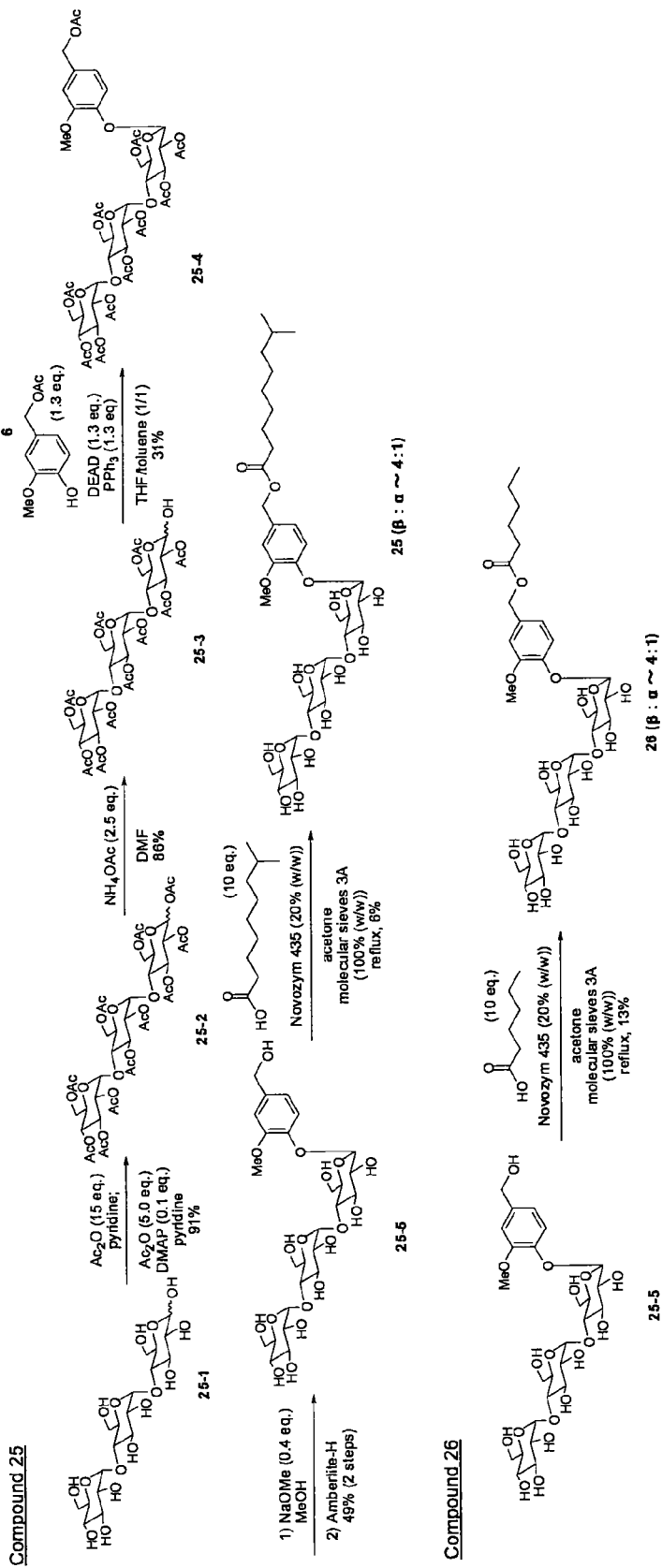
FIG. 15 shows the schemes of Examples 11 and 12.
Figure 16:
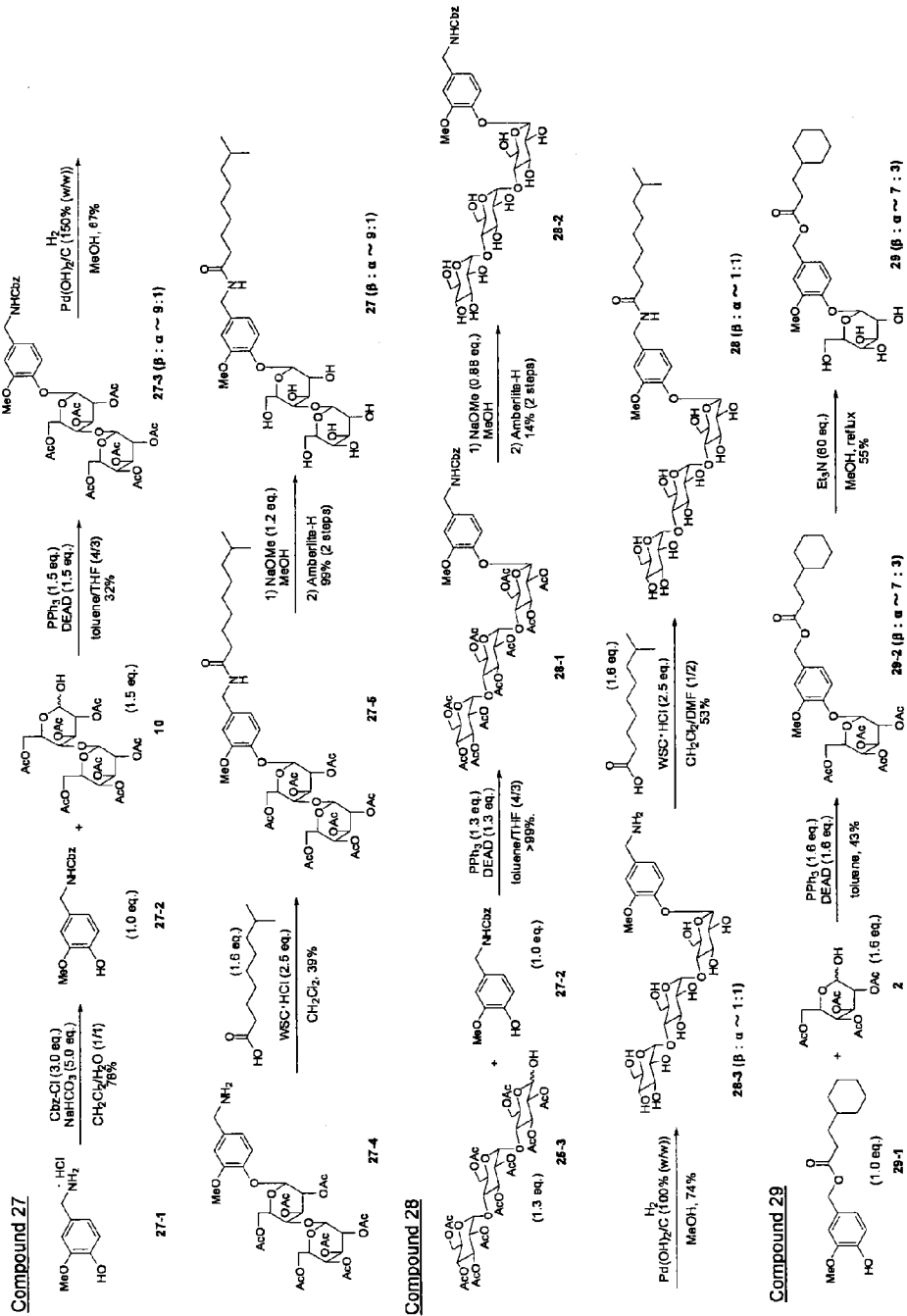
FIG. 16 shows the schemes of Comparative Examples 1 and 2, and Example 13.
Figure 17:
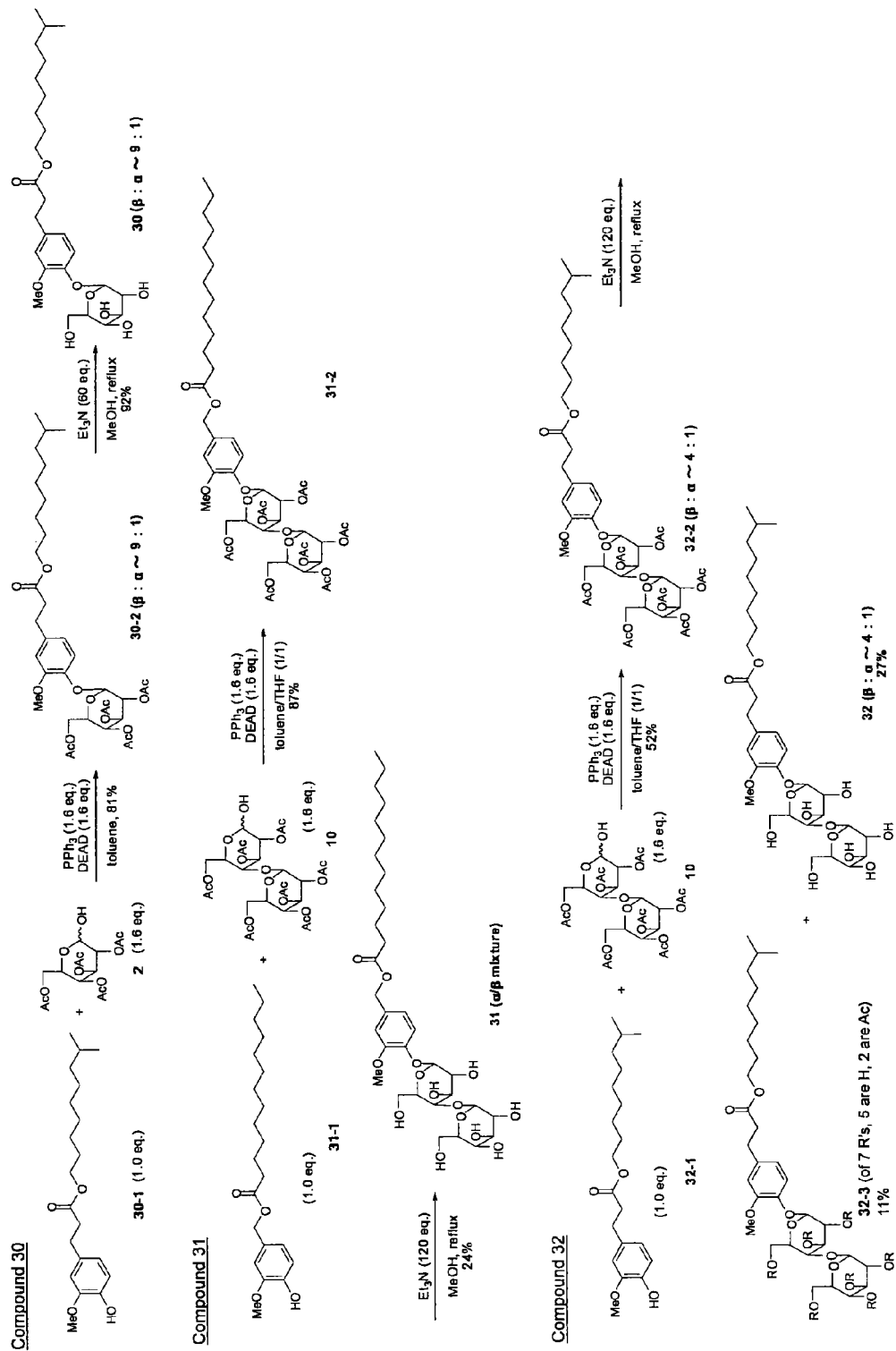
FIG. 17 shows the schemes of Examples 14 to 16.
Figure 18:
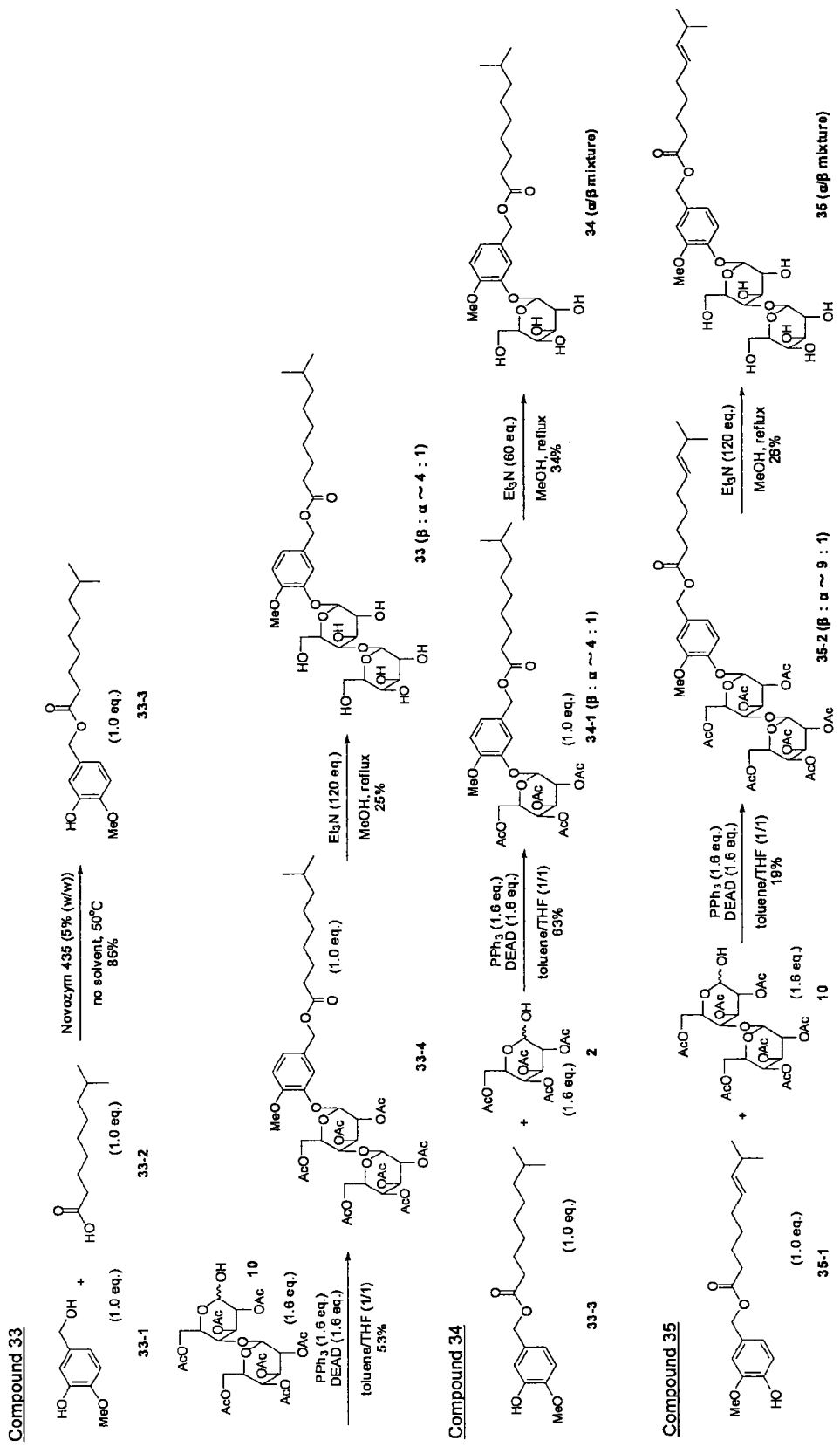
FIG. 18 shows the schemes of Examples 17 to 19.
Figure 19:
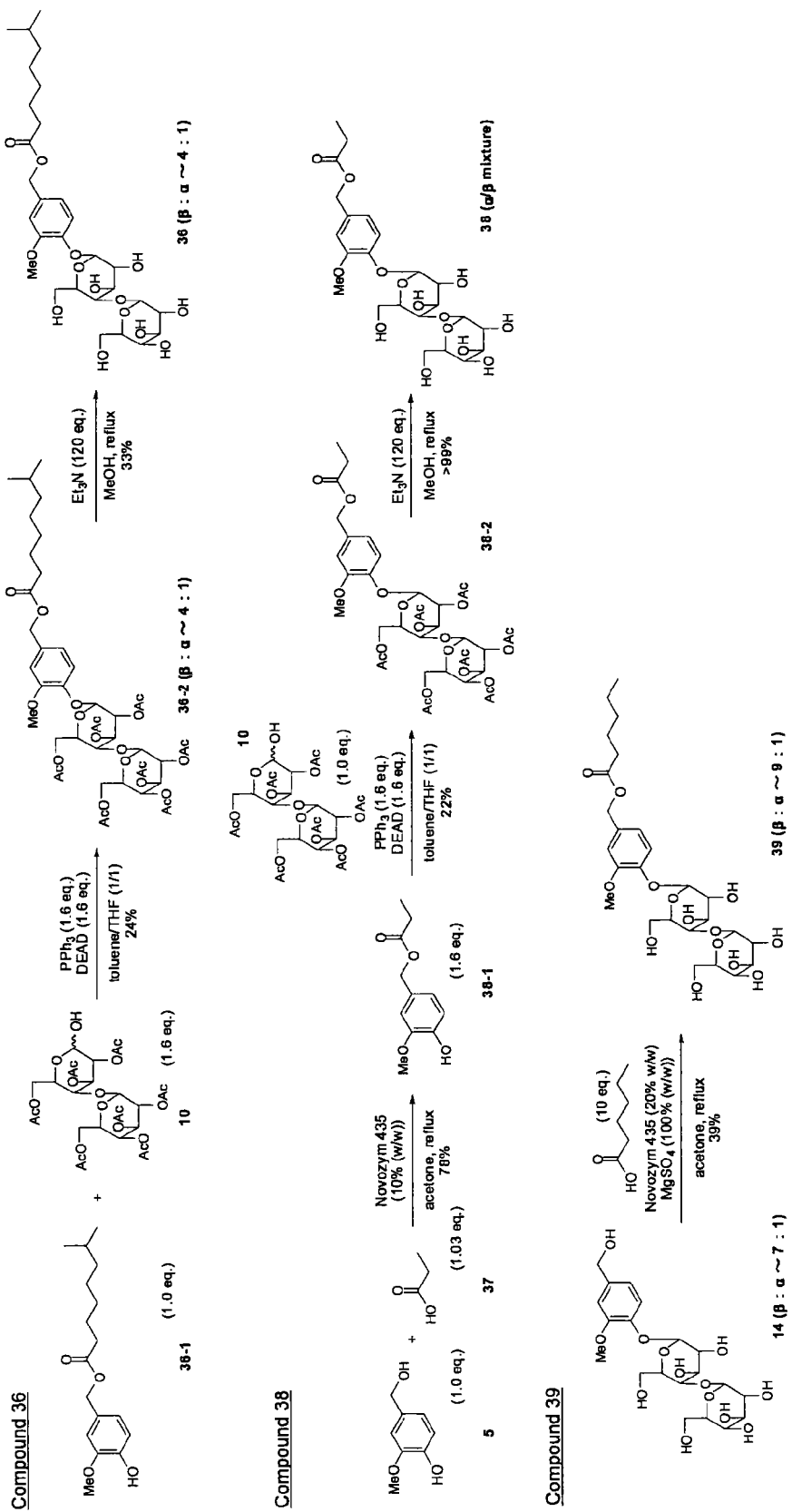
FIG. 19 shows the schemes of Examples 20 to 22.
Figure 20:
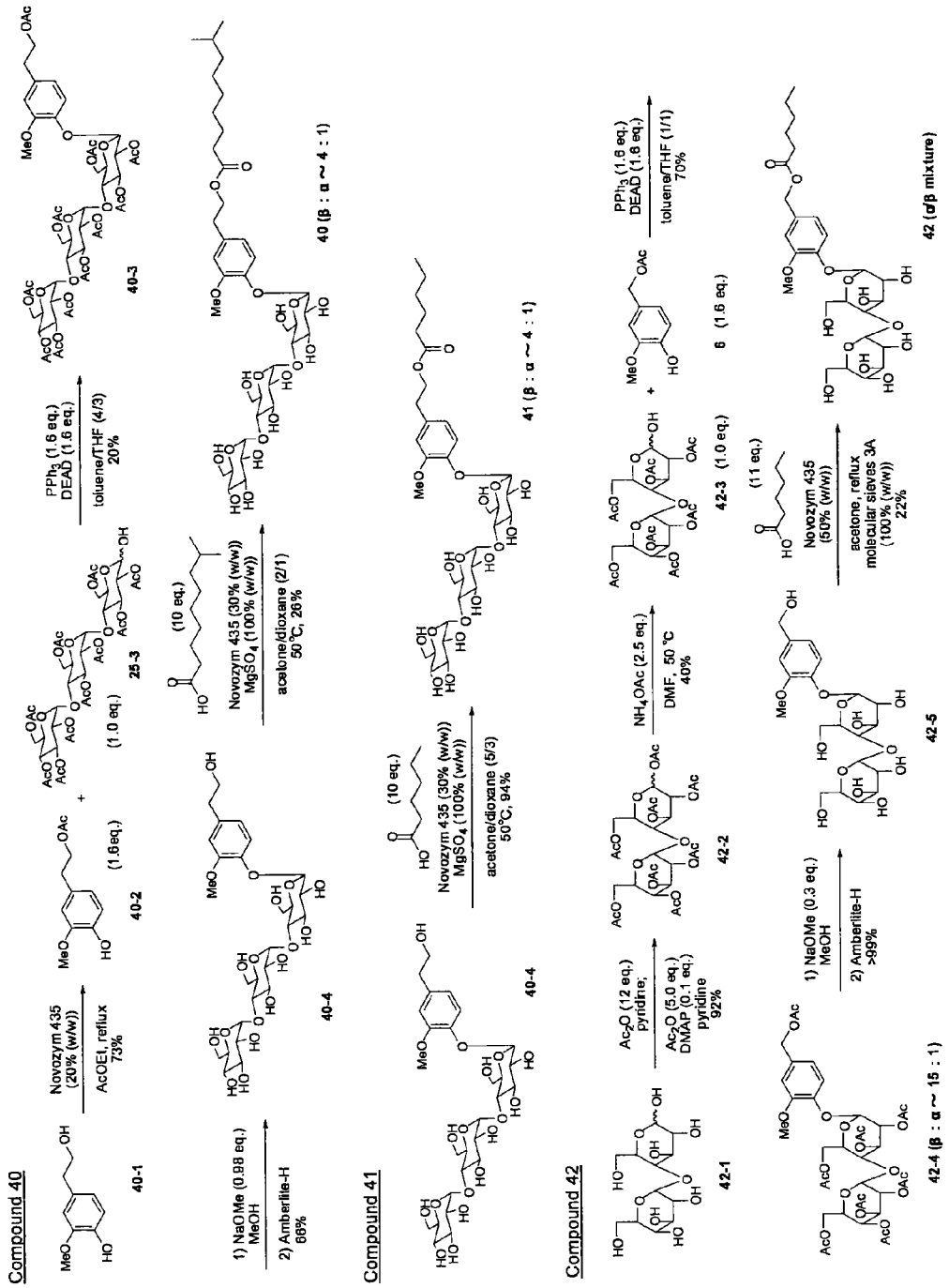
FIG. 20 shows the schemes of Examples 23 to 25.
Figure 21:
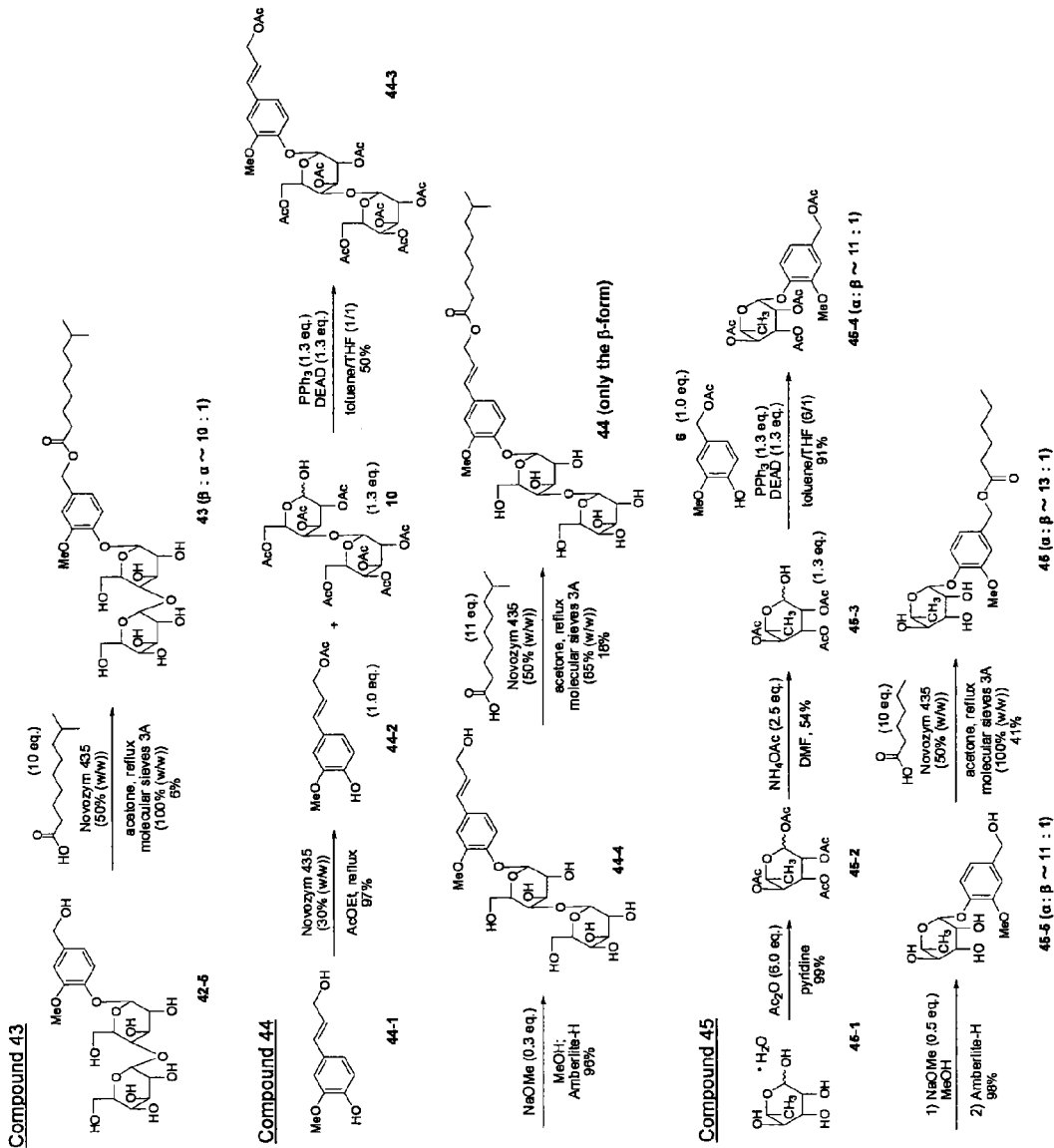
FIG. 21 shows the schemes of Examples 26 to 28.
Figure 22:
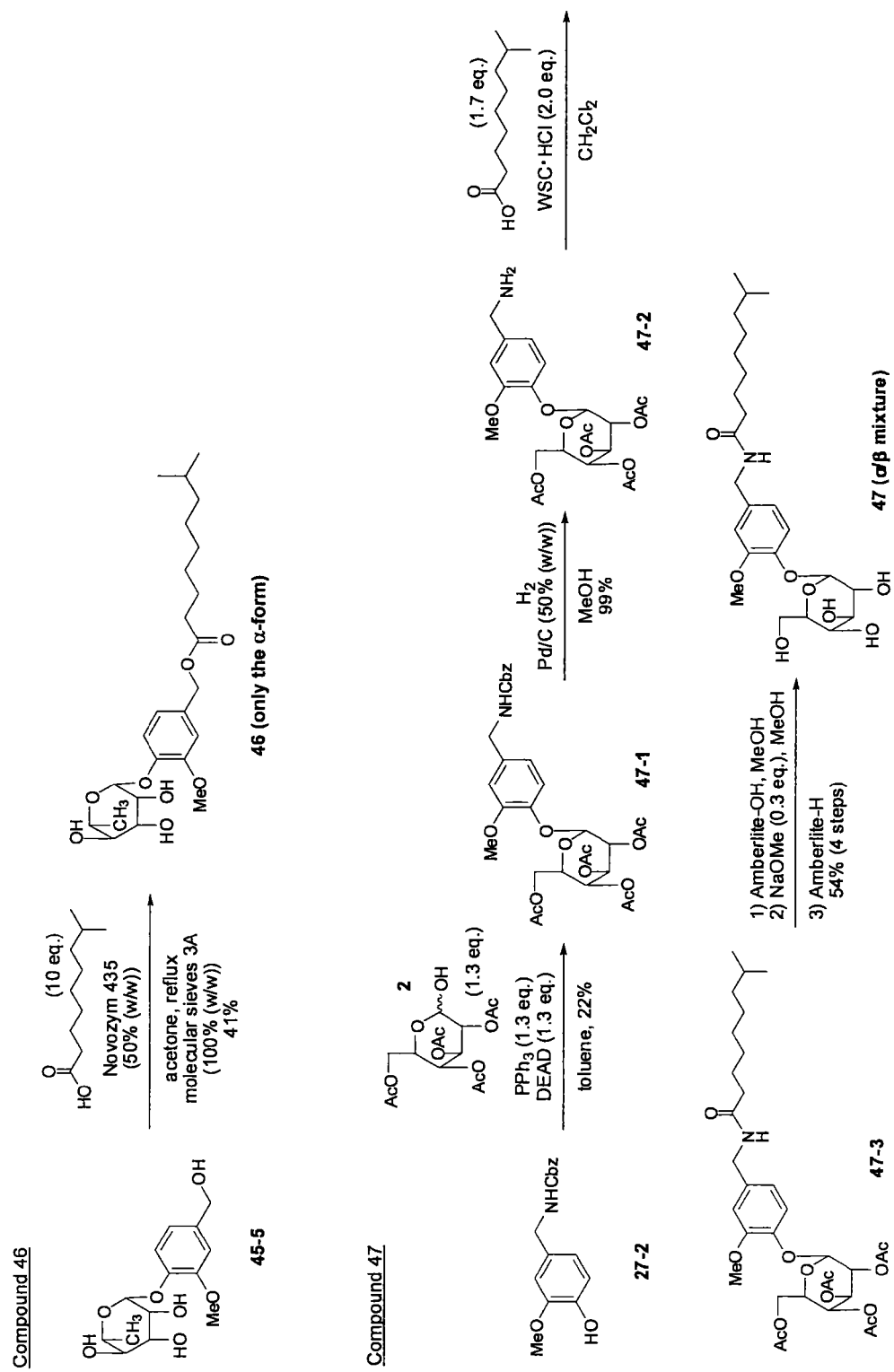
FIG. 22 shows the schemes of Example 29 and Comparative Example 3.

In the dihydrocapsiate glycoside compound 4 or 12 treatment group, GLP-1 concentration in the supernatant increased in a compound concentration-dependent manner as compared to the DMSO treatment group. However, the DCT treatment group did not show a similar change (see FIGS. 1 and 2). While induction of GLP-1 secretion by saccharide has been reported, since GLP-1 concentration of the compound 4 or 12 treatment group was markedly high as compared to the group treated with equimolar concentration of glucose or cellobiose, it is suggested that compound 4 or 12 itself has a GLP-1 secretion inducing action, rather than the saccharide produced by the decomposition of compound 4 or 12 (see FIG. 2). In addition, the capsaicin glycoside compound 47 or 27 treatment group did not show GLP-1 secretion promoting activity, as shown in FIG. 3. The GLP-1 concentration increased by the treatment with any of compounds 20, 18, 16, 30, 32, 32-3, 34, 35, 36, 24-2, 33, 14, 22, 23 and 24, as compared to the control group (FIGS. 4, 5, 6, 7, 8, 9, 10 and 11). The compound number, structural formula, and activity value are summarized in Table 1.

TABLE 1

| compound number | structural formula | activity value (100 μM) | activity value (300 μM) |
| --- | --- | --- | --- |
| 4 | [structure of N-[4-(β-D-glucopyranosyloxy)-3-methoxybenzyl] dihydrocapsiate glycoside] | 2.30 | — |
| 12 | [structure of dihydrocapsiate diglycoside] | 5.02 | — |

TABLE 1-continued

| # | Structure | | |
|---|---|---|---|
| 14 | (disaccharide-O-aryl-CH2OH with MeO) | 1.07 | 1.12 |
| 16 | (monosaccharide-O-aryl-CH2-O-C(=O)-C9H19, MeO) | 1.23 | 3.25 |
| 18 | (monosaccharide-O-aryl-CH2-O-C(=O)-(CH2)5-CH(CH3)2, MeO) | 1.33 | 1.85 |
| 20 | (monosaccharide-O-aryl-CH2-O-C(=O)-(CH2)3-CH=CH-CH(CH3)2, MeO) | 1.13 | 1.56 |
| 22 | (disaccharide-O-aryl-CH2-C(=O)-O-(CH2)7-CH(CH3)2, MeO) | 1.87 | 1.66 |
| 23 | (disaccharide-O-aryl-CH2CH2-O-C(=O)-(CH2)6-CH(CH3)2, MeO) | 1.37 | 10.27 |

TABLE 1-continued

| # | Structure | | |
|---|---|---|---|
| 24 | (structure) | 1.33 | 9.50 |
| 24-2 | (structure) | 0.87 | 1.15 |
| 30 | (structure) | 0.93 | 2.60 |
| 32 | (structure) | 1.24 | 3.46 |
| 32-3 | (structure) | 1.24 | 4.29 |

32-3 (of 7 R's, 5 are H, 2 are Ac)

TABLE 1-continued

| # | Structure | | |
|---|---|---|---|
| 33 | (glycoside structure) | 1.63 | 1.76 |
| 34 | (glycoside structure) | 1.29 | 1.94 |
| 35 | (diglycoside structure) | 1.14 | 2.40 |
| 36 | (diglycoside structure) | 1.19 | 2.41 |
| 27 | (glycoside amide structure) | 0.66 | 0.71 |
| 47 | (glycoside amide structure) | 0.61 | 0.78 |

Experimental Example 2

Glycoside dihydrocapsiate (to be abbreviated as glycoside DCT) used in Experimental Example 2 is O-[4-(β-D-glucopyranosyloxy)-3-methoxybenzyl]-8-methylnonanoic acid ester (4) (as a result of $^1$H-NMR analysis, β form:α form ratio was about 8:1) produced in Example 1.

Glycoside DCT was added at a proportion of 0.459% (w/w) to AIN-93 composition diet containing 30% lard (to be abbreviated as glycoside DCT diet or glycoside diet), and fed to mouse. As a result, long-term ingestion of glycoside DCT was confirmed to suppress food ingestion calories of mouse. As a control, AIN-93 composition diet containing 7% lard (to be abbreviated as normal diet), AIN-93 composition diet containing 30% lard (to be abbreviated as high-fat diet), and high-fat diet containing 0.3% (w/w) dihydrocapsiate (DCT) (to be abbreviated as DCT diet) were fed to the mouse.

The details of the test method are shown below. 7-week-old male C57BL/6J mice (n=46) (Charles River Laboratories) were acclimated for 2 weeks, divided into 4 groups such that they have the same average body weight, and each group was allowed to freely ingest a food having the composition shown in Table 2 for 56 days. The body weight and the food ingestion amount were measured every 3-4 days.

The mice that ingested a high-fat diet added with glycoside DCT showed a significant decrease in the total ingested calories during the test period, as compared to the mice that ingested a normal diet, a high-fat diet alone, or a high-fat diet added with DCT (see Table 3).

TABLE 2

Test Diet Composition (%)

| | normal diet | high-fat diet | DCT diet | glycoside DCT diet |
|---|---|---|---|---|
| cornstarch | 39.7486 | 22.4825 | 22.4825 | 22.3631 |
| vitamin free casein | 20.00 | 20.00 | 20.00 | 20.00 |
| α-starch | 13.2000 | 7.4661 | 7.4661 | 7.4265 |
| sucrose | 10.00 | 10.00 | 10.00 | 10.00 |
| lard | 7.00 | 30.00 | 30.00 | 30.00 |
| cellulose | 5.00 | 5.00 | 5.00 | 5.00 |
| vitamin mix (AIN93) | 1.00 | 1.00 | 1.00 | 1.00 |
| mineral mix (AIN93G) | 3.50 | 3.50 | 3.50 | 3.50 |
| cystine | 0.30 | 0.30 | 0.30 | 0.30 |
| choline bitartrate | 0.25 | 0.25 | 0.25 | 0.25 |
| TBHQ | 0.0014 | 0.0014 | 0.0014 | 0.0014 |
| DCT | | | 0.3 | |
| glycoside DCT | | | | 0.459 |
| | 100.0 | 100.0 | 100.3 | 100.3 |

*0.159% of GDCT is substituted by hydrocarbon

TABLE 3

Ingested Calories

| | normal diet | high-fat diet | DCT diet | glycoside diet |
|---|---|---|---|---|
| total ingested calories (kcal) | 790.2 ± 6.36$^a$ | 797.3 ± 18.99$^a$ | 802.1 ± 7.24$^a$ | 721.1 ± 16.87$^b$ |

Values are means ± SEM
p < 0.05 between different symbols Tukey-Kramer test

INDUSTRIAL APPLICABILITY

According to the present invention, a novel solid compound, which is completely free of a pungent taste even at a high concentration use, shows excellent stability even in various use conditions, and shows a remarkable GLP-1 secretion enhancing effect, can be provided. Moreover, it is highly significant that a pharmaceutical composition, a food composition and a cosmetic composition, each containing the compound can now be provided.

The compound represented by the formula (XV-1) or (XVII-1) is a novel compound, and is useful as an intermediate for the production of the glycoside compound of the present invention.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the is present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (I″):

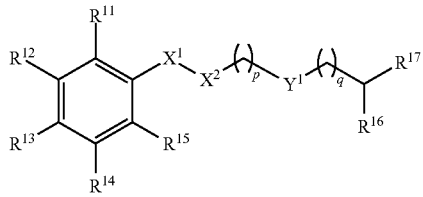

(I″)

wherein:
$R^{11}$, $R^{12}$, $R^{13}$, $R^{14}$ and $R^{15}$ are each independently a hydrogen atom, a hydroxyl group, a $C_{1-6}$ alkyl group, a $C_{1-6}$ alkoxy group, a $C_{1-6}$ alkyl-carbonyloxy group or a G-O— group, and at least one of $R^{11}$, $R^{12}$, $R^{13}$, $R^{14}$ and $R^{15}$ is a G-O— group, wherein G is a saccharide residue selected from the group consisting of a glucosyl group, a rhamnosyl group, a cellobiosyl group, a maltosyl group, and a maltotriosyl group;

$X^1$ is a methylene group, an ethylene group, a trimethylene group, a vinylene group or —CH=CH—CH$_2$—;

$X^2$ is —CO—O— or —O—CO—;

p and q are each an integer of 0 to 7, which satisfy a relationship of p+q=2 to 8;

$Y^1$ is an ethylene group or an alkenylene group having a carbon number of 2 to 15 and 1 to 3 double bonds, wherein the double bond may be any of cis and trans; and $R^{16}$ and $R^{17}$ are each independently a hydrogen atom, a methyl group or an ethyl group, or $R^{16}$ and $R^{17}$ together with the carbon atom to which they are bonded form a $C_{3-6}$ cycloalkane group.

2. The compound according to claim 1, which is represented by formula (I″-b):

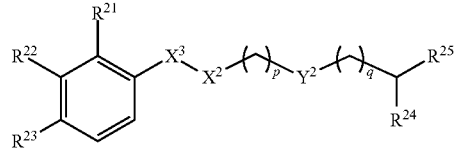

(I″-b)

wherein:
$R^{21}$ is a hydrogen atom, $R^{22}$ is a methoxy group, and $R^{23}$ is a G-O— group; or $R^{21}$ is a G-O— group, $R^{22}$ is a methoxy group, and $R^{23}$ is a hydrogen atom; or $R^{21}$ is a hydrogen atom, $R^{22}$ is a G-O— group, and $R^{23}$ is a methoxy group;

$X^3$ is a methylene group, an ethylene group or —CH=CH—CH$_2$—;

$X^2$ is —CO—O— or —O—CO—;

p and q are each an integer of 0 to 7, which satisfy a relationship of p+q=2 to 8;

$Y^2$ is an ethylene group or a vinylene group; and $R^{24}$ and $R^{25}$ are each independently a hydrogen atom or a methyl group, or $R^{24}$ and $R^{25}$ together with the carbon atom to which they are bonded form a $C_{3-6}$ cycloalkane group.

3. The compound according to claim 1, which is represented by formula (I'):

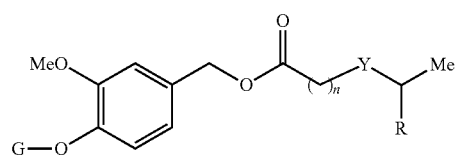

(I')

wherein:

Y is an ethylene group or a vinylene group;

R is a hydrogen atom or a methyl group; and n is an integer of 3 to 5.

4. The compound according to claim 3, which is represented by formula (I-1) or (I-2):

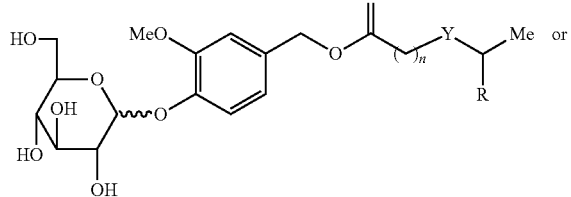

(I-1)

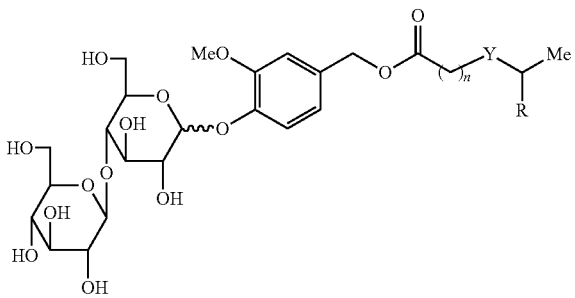

(I-2)

wherein:

Y is an ethylene group or a vinylene group;

R is a hydrogen atom or a methyl group; and n is an integer of 3 to 5.

5. The compound according to claim 1, which is represented by formula (I-a):

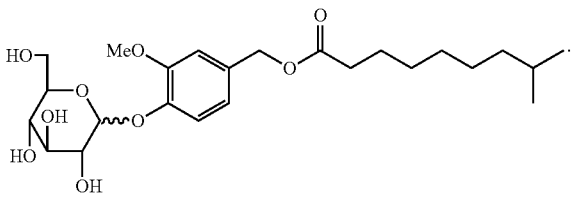

(I-a)

6. The compound according to claim 1, which is represented by formula (I-b):

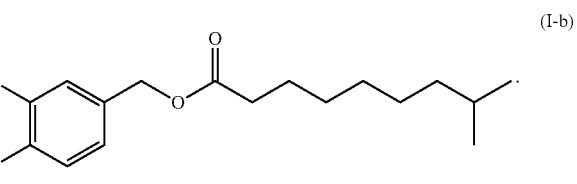

(I-b)

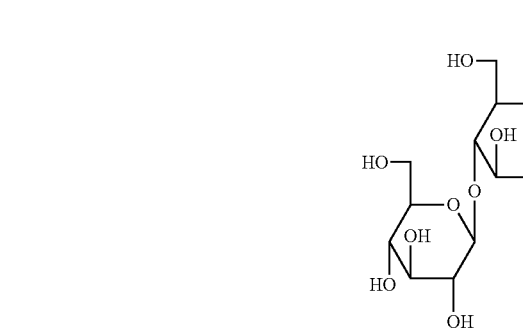

7. The compound according to claim 1, which is represented by formula (I-c):

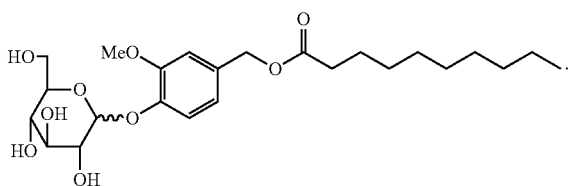

(I-c)

8. The compound according to claim 1, which is represented by formula (I-d):

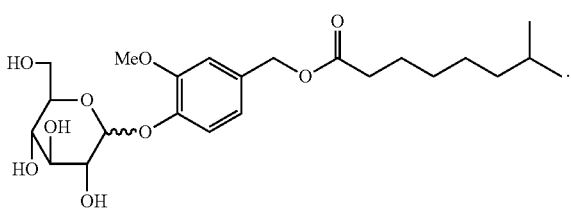

(I-d)

9. The compound according to claim 1, which is represented by formula (I-e):

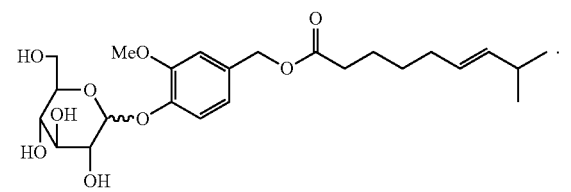

(I-e)

10. A pharmaceutical composition, comprising a compound according to claim 1 and at least one pharmaceutically acceptable carrier or excipient.

11. A food composition, comprising a compound according to claim 1.

12. A cosmetic composition, comprising a compound according to claim 1.

13. A method of producing a compound according to claim 1, comprising glycosidating a compound represented by formula (XIV):

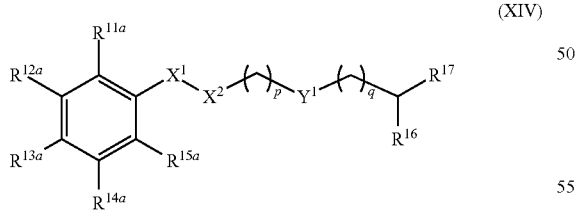

(XIV)

wherein $R^{11a}$, $R^{12a}$, $R^{13a}$, $R^{14a}$ and $R^{15a}$ are each independently a hydrogen atom, a hydroxyl group, a $C_{1-6}$ alkyl group, a $C_{1-6}$ alkoxy group or a $C_{1-6}$ alkyl-carbonyloxy group, and at least one of $R^{11a}$, $R^{12a}$, $R^{13a}$, $R^{14a}$ and $R^{15a}$ is a hydroxyl group;

$X^1$ is a methylene group, an ethylene group, a trimethylene group, a vinylene group or —CH=CH—CH$_2$—;

$X^2$ is —CO—O— or —O—CO—;

p and q are each an integer of 0 to 7, which satisfy a relationship of p+q=2 to 8;

$Y^1$ is an ethylene group or an alkenylene group having a carbon number of 2 to 15 and 1 to 3 double bonds, wherein the double bond may be any of cis and trans; and $R^{16}$ and $R^{17}$ are each independently a hydrogen atom, a methyl group or an ethyl group, or $R^{16}$ and $R^{17}$ together with the carbon atom to which they are bonded form a $C_{3-6}$ cycloalkane group;

with a saccharide residue selected from the group consisting of a glucosyl group, a rhamnosyl group, a cellobiosyl group, a maltosyl group, and a maltotriosyl group.

14. A method of producing a compound according to claim 3, comprising glycosidating a compound represented by formula (II):

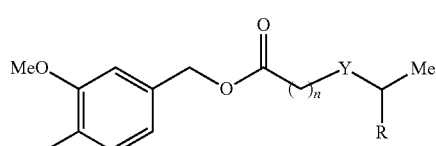

(II)

wherein:

Y is an ethylene group or a vinylene group;

R is a hydrogen atom or a methyl group; and n is an integer of 3 to 5, with a saccharide residue selected from the group consisting of a glucosyl group, a rhamnosyl group, a cellobiosyl group, a maltosyl group, and a maltotriosyl group.

15. A method of producing a compound represented by formula (I″-1):

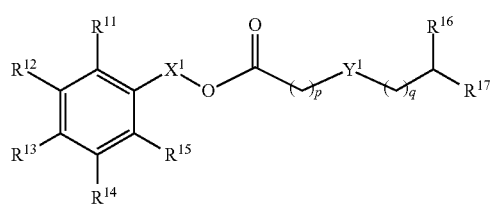

(I″-1)

wherein each symbol is as defined in claim 1, comprising reacting a compound represented by formula (XV):

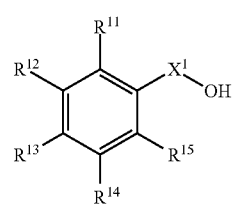

(XV)

wherein each symbol is as defined in claim 1, with a compound represented by formula (XVI):

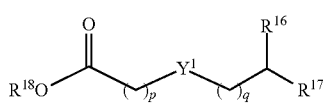

(XVI)

wherein $R^{18}$ is a hydrogen atom or a $C_{1-6}$ alkyl group, and other symbols are as defined in claim 1, or a salt thereof.

16. A method of producing a compound represented by formula (I″-2):

(I″-2)

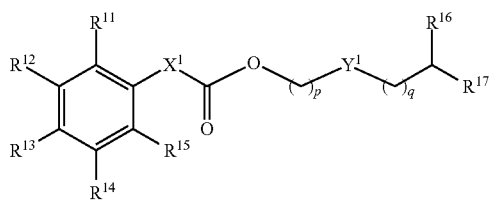

wherein each symbol is as defined in claim 1, comprising reacting a compound represented by formula (XVII):

(XVII)

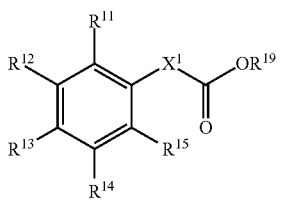

wherein $R^{19}$ is a hydrogen atom or a $C_{1-6}$ alkyl group, and other symbols are as defined in claim 1, or a salt thereof, with a compound represented by formula (XVIII):

(XVIII)

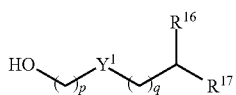

wherein each symbol is as defined in claim 1.

17. A method of producing a compound according to claim 3, comprising reacting a compound represented by formula (III):

(III)

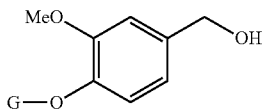

with a compound represented by the formula (IV):

(IV)

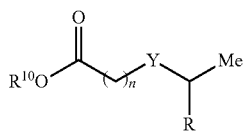

wherein:
  $R^{10}$ is a hydrogen atom or a $C_{1-6}$ alkyl group;
  Y is an ethylene group or a vinylene group;
  R is a hydrogen atom or a methyl group; and
  n is an integer of 3 to 5, or a salt thereof.

18. A method of producing a compound according to claim 4, comprising:

(a) reacting a compound represented by formula (II):

(II)

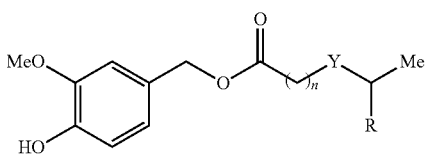

wherein:
  Y is an ethylene group or a vinylene group;
  R is a hydrogen atom or a methyl group; and
  n is an integer of 3 to 5, with a compound represented by formula (V) or (VI):

(V)

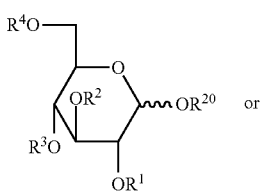

or (VI)

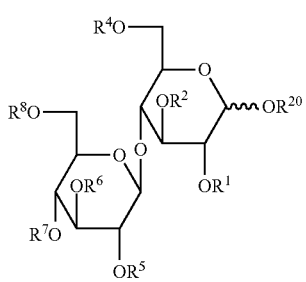

wherein:
  $R^1$, $R^2$, $R^3$, $R^4$, $R^5$, $R^6$, $R^7$ and $R^8$ are each independently a hydroxyl-protecting group; and
  $R°$ is a hydrogen atom or a hydroxyl-protecting group, to obtain a compound represented by formula (VII) or (VIII):

(VII)

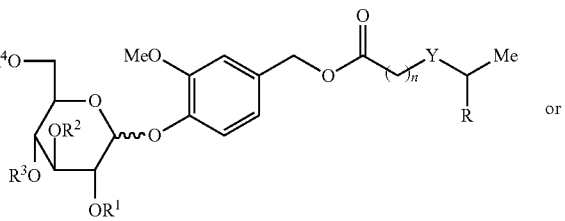

or (VIII)

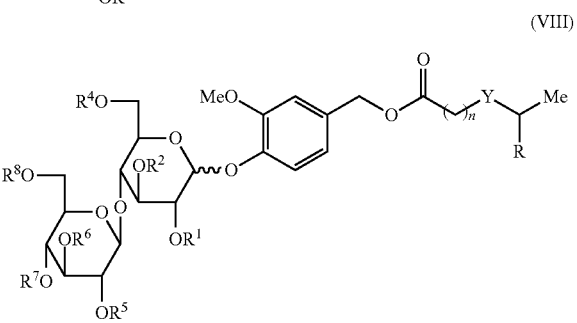

wherein:
  $R^1$, $R^2$, $R^3$, $R^4$, $R^5$, $R^6$, $R^7$ and $R^8$ are each independently a hydroxyl-protecting group;

Y is an ethylene group or a vinylene group;

R is a hydrogen atom or a methyl group; and n is an integer of 3 to 5; and (b) removing the hydroxyl-protecting groups of the compound represented by formula (VII) or (VIII).

19. The method according to claim 18, wherein said removing said hydroxyl-protecting groups is performed in the presence of a lipase.

20. A method of producing a compound according to claim 4, comprising reacting a compound represented by formula (XII) or (XIII):

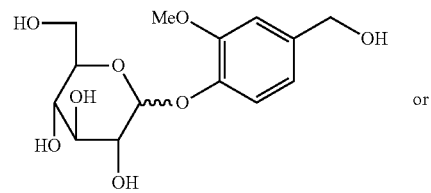
(XII)

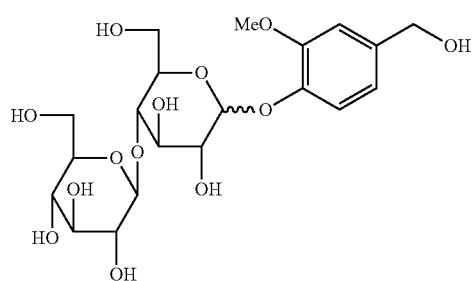
(XIII)

with a compound represented by formula (IV):

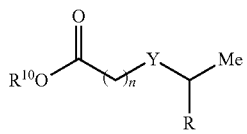
(IV)

wherein:

$R^{10}$ is a hydrogen atom or a $C_{1-6}$ alkyl group;

Y is an ethylene group or a vinylene group;

R is a hydrogen atom or a methyl group; and n is an integer of 3 to 5, or a salt thereof.

21. A method of producing a compound according to claim 4, comprising:

(a) reacting a compound represented by formula (IX):

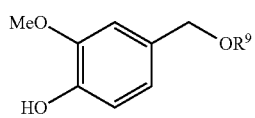
(IX)

wherein $R^9$ is a hydroxyl-protecting group, with a compound represented by formula (V) or (VI):

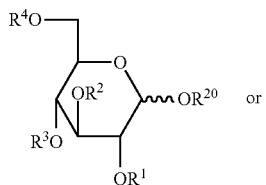
(V)

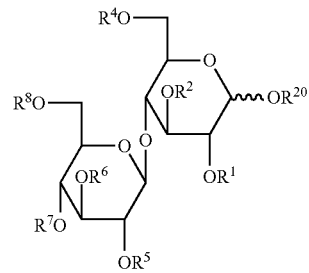
(VI)

wherein:

$R^1$, $R^2$, $R^3$, $R^4$, $R^5$, $R^6$, $R^7$ and $R^8$ are each independently a hydroxyl-protecting group; and $R^{20}$ is a hydrogen atom or a hydroxyl-protecting group, to obtain a compound represented by formula (X) or (XI):

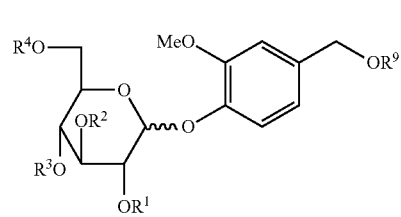
(X)

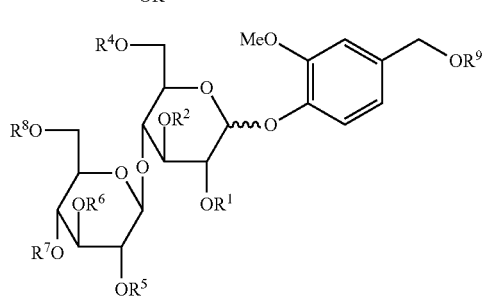
(XI)

wherein:

$R^1$, $R^2$, $R^3$, $R^4$, $R^5$, $R^6$, $R^7$, $R^8$ and $R^9$ are each independently a hydroxyl-protecting group;

(b) removing the hydroxyl-protecting groups of the compound represented by formula (X) or (XI), to obtain a compound represented by formula (XII) or (XIII):

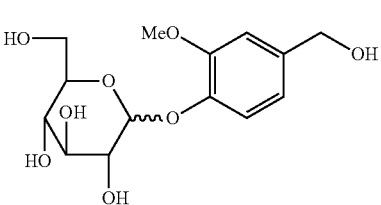
(XII)

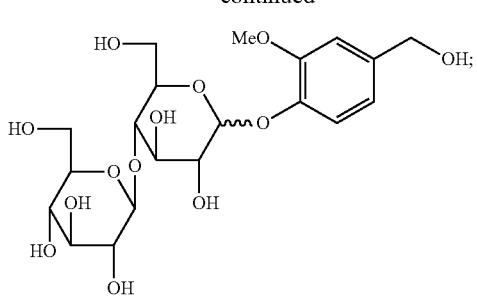

(XIII)

(c) reacting said compound represented by formula (XII) or (XIII) with a compound represented by formula (IV):

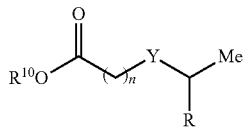

(IV)

wherein:
R$^{10}$ is a hydrogen atom or a C$_{1-6}$ alkyl group;
Y is an ethylene group or a vinylene group;
R is a hydrogen atom or a methyl group; and
n is an integer of 3 to 5, or a salt thereof.

22. A method of treating diabetes or suppressing appetite in a mammal, comprising administering an effective amount of a compound according to claim 1 to the mammal.

23. A compound represented by formula (XV-1):

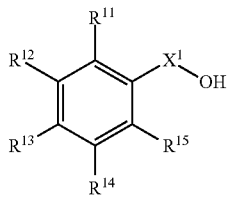

(XV-1)

wherein:
R$^{11}$, R$^{12}$, R$^{13}$, R$^{14}$, and R$^{15}$ are each independently a hydrogen atom, a hydroxyl group, a C$_{1-6}$ alkyl group, a C$_{1-6}$ alkoxy group, a C$_{1-6}$ alkyl-carbonyloxy group or a G-O— group, and at least one of R$^{11}$, R$^{12}$, R$^{13}$, R$^{14}$, and R$^{15}$ is a G-O— group, wherein G is a saccharide residue, including a saccharide residue having protecting group(s); and
X$^1$ is a single bond, or a methylene group, an ethylene group, or —CH=CH—CH$_2$—,
with the proviso that the following compounds are excluded:

(1) a compound wherein R$^{13}$ is a G-O— group, G is a glucosyl group, R$^{11}$, R$^{12}$, R$^{13}$, R$^{14}$ and R$^{15}$ are each a hydrogen atom, and X$^1$ is a methylene group or an ethylene group;

(2) a compound wherein R$^{13}$ is a G-O— group, G is a glucosyl group, R$^{12}$ is a hydroxyl group, R$^{11}$, R$^{14}$, and R$^{15}$ are each a hydrogen atom, and X$^1$ is a methylene group;

(3) a compound wherein R$^{13}$ is a G-O— group, G is a glucosyl group, R$^{12}$ is a methoxy group, R$^{11}$, R$^{14}$ and R$^{15}$ are each a hydrogen atom, and X$^1$ is a methylene group or an ethylene group;

(4) a compound wherein R$^{13}$ is a G-O— group, G is a glucosyl group, R$^{12}$ and R$^{14}$ are each a methoxy group, R$^{11}$ and R$^{15}$ are each a hydrogen atom, and X$^1$ is a methylene group or an ethylene group;

(5) a compound wherein R$^{13}$ is a G-O— group, G is a maltosyl group, R$^{11}$, R$^{12}$ R$^{14}$ and R$^{15}$ are each a hydrogen atom, and X$^1$ is a methylene group;

(6) a compound wherein R$^{11}$ is a G-O— group, G is a glucosyl group or a maltosyl group, R$^{12}$, R$^{13}$, R$^{14}$ and R$^{15}$ are each a hydrogen atom, and X$^1$ is a methylene group; and (7) a compound wherein R$^{11}$ is a G-O— group, G is a glucosyl group, R$^{12}$ is a hydroxyl group or a methoxy group, R$^{13}$, R$^{14}$ and R$^{15}$ are each a hydrogen atom, and X$^1$ is a methylene group.

24. A compound represented by formula (XVII-1), or a salt thereof:

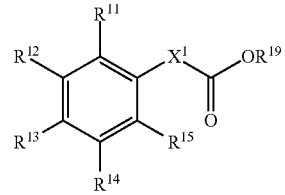

(XVII-1)

wherein:
R$^{11}$, R$^{12}$, R$^{13}$, R$^{14}$ and R$^{15}$ are each independently a hydrogen atom, a hydroxyl group, a C$_{1-6}$ alkyl group, a C$_{1-6}$ alkoxy group, a C$_{1-6}$ alkyl-carbonyloxy group or a G-O— group, and at least one of R$^{11}$, R$^{12}$, R$^{13}$, R$^{14}$ and R$^{15}$ is a group, wherein G is a saccharide residue, including a saccharide residue having protecting group(s);
X$^1$ is a methylene group or —CH=CH—CH$_2$—; and
R$^{19}$ is a hydrogen atom or a C$_{1-6}$ alkyl group,
with the proviso that the following compounds are excluded:

(1) a compound wherein R$^{13}$ is a G-O— group, G is a glucosyl group or a mannosyl group, R$^{11}$, R$^{12}$, R$^{14}$ and R$^{15}$ are each a hydrogen atom, X$^1$ is a methylene group, and R$^{19}$ is a hydrogen atom;

(2) a compound wherein R$^{13}$ is a G-O— group, G is a glucosyl group, R$^{11}$ is a hydroxyl group, R$^{11}$, R$^{12}$, R$^{14}$ and R$^{15}$ are each a hydrogen atom, X$^1$ is a methylene group, and R$^{19}$ is a hydrogen atom; and (3) a compound wherein R$^{13}$ is a G-O— group, G is a glucosyl group, R$^{12}$ is a methoxy group, R$^{11}$, R$^{14}$ and R$^{15}$ are each a hydrogen atom, X$^1$ is a methylene group or an ethylene group, and R$^{19}$ is a hydrogen atom.

25. A method of treating diabetes in a mammal, comprising administering an effective amount of a compound according to claim 1 to the mammal.

26. A method suppressing appetite in a mammal, comprising administering an effective amount of a compound according to claim 1 to the mammal.

* * * * *